United States Patent
Griffith

(10) Patent No.: US 7,176,210 B2
(45) Date of Patent: Feb. 13, 2007

(54) CANNABINOID RECEPTOR LIGANDS AND USES THEREOF

(75) Inventor: David A. Griffith, Old Saybrook, CT (US)

(73) Assignee: Pfizer Inc., New York, NY (US)

( * ) Notice: Subject to any disclaimer, the term of this patent is extended or adjusted under 35 U.S.C. 154(b) by 396 days.

(21) Appl. No.: 10/762,959

(22) Filed: Jan. 21, 2004

(65) Prior Publication Data

US 2004/0157838 A1 Aug. 12, 2004

Related U.S. Application Data

(60) Provisional application No. 60/446,450, filed on Feb. 10, 2003.

(51) Int. Cl.
| | | |
|---|---|---|
| A61K 31/519 | (2006.01) | |
| C07D 239/70 | (2006.01) | |
| C07D 487/04 | (2006.01) | |
| A61P 3/04 | (2006.01) | |
| C07D 231/38 | (2006.01) | |
| C07D 211/98 | (2006.01) | |
| C07D 204/04 | (2006.01) | |
| C07D 295/04 | (2006.01) | |

(52) U.S. Cl. .................. 514/259.31; 544/230; 544/281; 544/117; 548/371.7; 548/357.5; 548/953; 546/223

(58) Field of Classification Search ........... 514/252.16, 514/259.3, 259.31; 544/281, 230
See application file for complete search history.

(56) References Cited

U.S. PATENT DOCUMENTS

| | | | |
|---|---|---|---|
| 3,155,670 A | 11/1964 | Janssen | |
| 3,161,644 A | 12/1964 | Janssen | |
| 4,925,846 A | 5/1990 | Deacon et al. | |
| 4,944,790 A | 7/1990 | Moser et al. | |
| 4,992,442 A * | 2/1991 | Tsujitani et al. | 514/267 |
| 5,086,057 A | 2/1992 | Takiguchi et al. | |
| 5,134,142 A | 7/1992 | Matsuo et al. | |
| 5,462,960 A | 10/1995 | Barth et al. | |
| 5,571,813 A | 11/1996 | Buhter et al. | |
| 5,596,106 A | 1/1997 | Cullinan et al. | |
| 5,624,941 A | 4/1997 | Barth et al. | |
| 5,744,491 A | 4/1998 | Boigegrain et al. | |
| 5,744,493 A | 4/1998 | Boigegrain et al. | |
| 5,747,524 A | 5/1998 | Cullinan et al. | |
| 5,843,951 A * | 12/1998 | Inoue et al. | 514/259.3 |
| 5,925,768 A | 7/1999 | Barth et al. | |
| 6,028,084 A | 2/2000 | Barth et al. | |
| 6,060,478 A | 5/2000 | Gilligan et al. | |
| 6,100,259 A | 8/2000 | Xiang et al. | |
| 6,344,474 B1 | 2/2002 | Maruani et al. | |
| 6,355,631 B1 | 3/2002 | Bouchard et al. | |
| 6,372,743 B1 | 4/2002 | Darrow et al. | |
| 6,432,984 B1 | 8/2002 | Barth et al. | |
| 6,476,038 B1 | 11/2002 | Darrow et al. | |
| 6,476,060 B2 | 11/2002 | Lange et al. | |
| 6,479,479 B2 | 11/2002 | Achard et al. | |
| 6,509,367 B1 | 1/2003 | Martin et al. | |
| 6,518,264 B2 | 2/2003 | Achard et al. | |
| 6,566,356 B2 | 5/2003 | Achard et al. | |
| 2001/0027193 A1 | 10/2001 | Achard et al. | |
| 2001/0053788 A1 | 12/2001 | Lange et al. | |
| 2002/0019383 A1 | 2/2002 | Achard et al. | |
| 2002/0019421 A1 | 2/2002 | Biberman et al. | |
| 2002/0035102 A1 | 3/2002 | Achard et al. | |
| 2002/0091114 A1 | 7/2002 | Plot-Grosjean et al. | |
| 2002/0119972 A1 | 8/2002 | Leftheris et al. | |
| 2002/0128302 A1 | 9/2002 | Maruani et al. | |
| 2002/0188007 A1 | 12/2002 | Barth et al. | |
| 2003/0003145 A1 | 1/2003 | Abramovici et al. | |
| 2003/0055033 A1 | 3/2003 | Achard et al. | |
| 2003/0114495 A1 | 6/2003 | Finke et al. | |
| 2003/0125330 A1 | 7/2003 | Gilligan | |

(Continued)

FOREIGN PATENT DOCUMENTS

EP          293220 B1     8/1994

(Continued)

OTHER PUBLICATIONS

West, Anthony R., Solid State Chemistry and its Applications, Wiley, New York, 1988, pp. 358 & 365.*

(Continued)

*Primary Examiner*—Mark Berch
*Assistant Examiner*—Susanna Moore
(74) *Attorney, Agent, or Firm*—Gregg C. Benson; Arlene K. Musser

(57) ABSTRACT

Compounds of Formula (I) that act as cannabinoid receptor ligands and their uses in the treatment of diseases linked to the mediation of the cannabinoid receptors in animals are described herein (I)

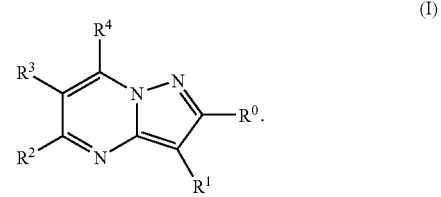

121 Claims, No Drawings

U.S. PATENT DOCUMENTS

| | | |
|---|---|---|
| 2003/0139386 A1 | 7/2003 | Cote et al. |
| 2003/0199536 A1 | 10/2003 | Thomas et al. |
| 2004/0072833 A1 | 4/2004 | Nakai et al. |
| 2004/0077650 A1 | 4/2004 | Dow |
| 2004/0092520 A1 | 5/2004 | Griffith |
| 2004/0122074 A1 | 6/2004 | Dow |
| 2004/0157839 A1 | 8/2004 | Griffith |
| 2005/0203106 A1* | 9/2005 | Gudmundsson et al. . 514/259.3 |

FOREIGN PATENT DOCUMENTS

| | | |
|---|---|---|
| EP | 1354884 | 10/2003 |
| JP | JP 05125079 A2 * | 5/1993 |
| WO | WO 96/02248 A1 | 2/1996 |
| WO | WO 01/15609 A1 | 5/2000 |
| WO | WO 01/24798 A1 | 4/2001 |
| WO | WO 01/028557 A1 | 4/2001 |
| WO | WO 01/029007 A1 | 4/2001 |
| WO | WO 01/032629 A1 | 5/2001 |
| WO | WO 01/032663 A2 | 5/2001 |
| WO | WO 01/58450 A2 | 8/2001 |
| WO | WO 01/85092 A2 | 11/2001 |
| WO | WO 02053565 | 7/2002 |
| WO | WO 02/076949 A1 | 10/2002 |
| WO | WO 03/006007 A1 | 1/2003 |
| WO | WO 03/007887 A2 | 1/2003 |
| WO | WO 03/018060 A1 | 3/2003 |
| WO | WO 03/020217 A2 | 3/2003 |
| WO | WO 03/020314 A1 | 3/2003 |
| WO | WO 03/026647 A1 | 4/2003 |
| WO | WO 03/026648 A1 | 4/2003 |
| WO | WO 03/027069 A1 | 4/2003 |
| WO | WO 03/027076 A2 | 4/2003 |
| WO | WO 03/027114 A1 | 4/2003 |
| WO | WO 03/040107 A1 | 5/2003 |
| WO | WO 03/051850 A1 | 6/2003 |
| WO | WO 03/051851 A1 | 6/2003 |
| WO | WO 03/075660 A1 | 9/2003 |
| WO | WO 03/077847 A2 | 9/2003 |
| WO | WO 03/078413 A1 | 9/2003 |
| WO | WO 03/082190 A2 | 10/2003 |
| WO | WO 03/082191 A2 | 10/2003 |
| WO | WO 03/082256 A2 | 10/2003 |
| WO | WO 03/082833 A1 | 10/2003 |
| WO | WO 03/084943 A2 | 10/2003 |
| WO | WO 03/086288 A2 | 10/2003 |
| WO | WO 03/087037 A1 | 10/2003 |
| WO | WO 03095455 | 11/2003 |
| WO | WO 04/012617 A2 | 2/2004 |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Huestis, M.A. et al, Arch Gen Psychiatry. Apr. 2001;58(4):322-8.*
Pertwee, R.G., Forsch Komplementarmed. Oct. 1999; 6 Suppl. 3:12-5.*
Giuffrida, A. et al, J Pharmacol Exp Ther. Jul. 2001;298(1):7-14.*
Barth F, Rinaldi-Carmona M., Curr Med Chem. Aug. 1999;6(8):745-55. Abstract only PMID: 10469889.*
Brotchie JM., Curr Opin Pharmacol. Feb. 2003;3(1):54-61, Abstract only PMID:12550742.*
Ruiu S, Pinna GA, Marchese G, Mussinu JM, Saba P, Tambaro S, Casti P, Vargiu R, Pani L.J Pharmacol Exp Ther. Jul. 2003;306(1):363-70.*
Tzavara ET, Davis RJ, Perry KW, Li X, Salhoff C, Bymaster FP, Witkin JM, Nomikos GG, Br J Pharmacol. Feb. 2003;138(4): 53.*
Anonymous, "Developments in the Treatment of Parkinson's Disease", Drug Therap. Bull., 37, 1999, 36-40.*
Burke, J.R. et al, Postgraduate Medicine, 1999, pp. 85, 86, 89, 90, 93, 94, & 96.*
Shoulson, I., Science, 282, 1998, 1072-1074.*
Poncelet, M.; Psychopharmacology; 1999; 144; 144-150.*
Mas-Nieto, M.; British Journal of Pharmacology; 2001; 132; 1809-1816.*
Chaperon, F.; Psychopharmacology; 1998; 135; 324-332.*
Sanudo-Pena; M.C.; Neuroscience Letters; 1997; 223; 125-128.*
Mansbach, R.S.; Psychopharmacology; 1996; 124; 315-322.*
Mechoulam, R.; TRENDS in Pharmacological Science; 2003; 24(6); 266-268.*
Cohen, C.; Behavioural Pharmacology; 2002; 13; 451-463.*
Wolff, M.C.; European Jouranl of Pharmacology; 2003; 477; 213-217.*
Di Marzo, V.; FASEB Journal; 2000; 14; 1432-1438.*
Ferrer, B.; European Journal of Neuroscience; 2003; 18; 1607-1614.*
Croci, T.; British Journal of Pharmacology; 2003; 140; 115-122.*
Senga, K., et al., "Synthesis and Antischistosomal Activity of Certain Pyrazolo[1,5-a]pyrimidines," *J Med Chem*, 24, 610-613 (1981).
Sugimoto, O., et al., "A facile halgenation of some hydroxyheterocycles using triphenylphosphine and N-halosuccinimide," *Tetra Lett*, 40, 7477-7478 (1990).
Almansa, C., et al., "Synthesis and SAR of a New Series of COX-2 Selective Inhibitors: Pyrazolo[1,5-a]pyrimidines," *J. Med. Chem*, 44, 350-361, (2001).
Tzavara, E.T., et al., "The CB1 Receptor Antagonist SR141716A selectively increases monoaminergic neurotransmission in the medial prefrontal cortex: Implications for Therapeutic Actions," *J Pharmacol*, 138, 544-553 (2003).
Racz, I., et al., "A Critical Role for the Cannabinoid CB1 Receptors in Alcohol Dependence and Stress-Stimulated Ethanol Drinking," *J Neurosci*, 23(6), 2453-2458 (2003).
Croci, T., et al., "Role of Cannabinoid CB1 Receptors and Tumor Necrosis Factor-α in the gut and systemic anti-inflammatory activity of SR 141716 (Rimonabant) in rodents," *Brit J Pharmacol*, 140, 115-122 (2003).
DaSilva, G.E., et al., "Potentiation of Penile Erection and Yawning Responses to Apomorphine by Cannabinoid Receptor Antagonists in Rats," *Neurosci Let*, 349, 49-52 (2003).
Wang, L., et al., "Endocannabinoid Signaling via Cannabinoid Receptor 1 is Involved in Ethanol Preference and its Age-Dependent Decline in Mice," *PNAS*, 100(3), 1393-1398 (2003).
Ruiu, S., et al., "Synthesis and Characterization of NESS 0327: A Novel Putative Antagonist of the CB1 Cannabinoid Receptor," *J Pharmacol Exp Therap*, 306, 363-370 (2003).
Howlett, A.C., et al., "International Union of Pharmacology. XXVII. Classification of Cannabinoid Receptors," *Pharmacol Rev*, 54, 161-202 (2002).
Gomez, R., et al., "A Peripheral Mechanism for CB1 Cannabinoid Receptor-Dependent Modulation of Feeding," *J. Neurosci*, 22(21), 9612-9617 (2002).
Wiley, J.L., et al., "Novel Pyrazole Cannabinoids: Insights into CB1 Receptor Recognition and Activation," *J Pharmacol Exp Therap*, 296(3), 1013-1022 (2001).
Lellemand, F., et al., "Effects of CB1 Cannabinoid Receptor Blockade on Ethanol Preference After Chronic Ethanol Administration," *Alcohol Clin Exp Res*, 25(9), 1317-1323 (2001).
Pertwee, R.G., "Cannabinoids and the Gastronintestinal Tract," *Gut*, 48, 859-867 (2001).
Pertwee, R.G., "Cannabinoid Receptor Ligands: Clinical and Neuropharmacological Considerations, Relevant to Future Drug Discovery and Development," *Exp. Opin. Invest. Drugs*, 9(7), 1573-1571 (2000).
Hungund, B.L and B.S. Basavarajappa, "Are Anadamide and Cannabinoid Receptors involved in Ethanol Tolerance? A Review of the Evidence," *Alcohol & Alcoholism*. 35(2) 126-133, (2000).
Freedland, C.S., et al., "Effects of SR141716A, a Central Cannabinoid Receptor Antagonist, on Food-maintained Responding," *Pharmacol Biochem Behav*, 67, 265-270 (2000).

Lan, R., et al., "Structure-Activity Relationships of Pyrazole Derivatives as Cannabinoid Receptor Antagonists" *J. Med. Che.m*, 42, 769-776 (1999).

Pertwee, R.G., "Pharmacology of Cannabinoid Receptor Ligands" *Curr Med Chem*, 6, 635-664 (1999).

Basavarajappa, B.S., et al., "Chronic Ethanol Administration Down-regulates Cannabinoid Receptors in Mouse Brain Synaptic Plasma Membrane," *Brain Res*, 793, 212-218 (1998).

Thomas, B.F., et al., "Comparative Receptor Binding Analyses of Cannabinoid Agonists and Antagonists," *J Pharmacol Exp Therap*, 285, 285-292 (1998).

Colombo, G., et al., "Appetite Suppression and Weight Loss after the Cannabinoid Antagonist SR141716," *Life Sci.*, 63, PL113-PL117 (1998).

Simiand, J., et al., "SR141716, a CB1 Cannabinoid Receptor Antagonist, Selectively Reduces Sweet Food Intake in Marmose," *Behav. Pharmacol.*, 9, 179-181 (1998).

Chaperon, F., et al., "Involvement of Central Cannabinoid (CB1) Receptors in the Establishment of Place Conditioning in Rats," *Psychopharmacology*, 135, 324-332 (1998).

Arnone, M., et al., "Selective Inhibition of Sucrose and Ethanol Intake by SR141716, an Antagonist of Central Cannabinoid (CB1) Receptors," *Psychopharmacol*, 132, 104-106 (1997).

Savontaus, E., et al., "Anti-Obesity Effect of MPV-1743 A III, a Novel Imidazoline Derivative, in Genetic Obesity," *Eur J Pharmacol*, 328, 207-215 (1997).

Sanudo-Pena, M.C., et al., "Endogenous Cannabinoids as an Aversive or Counter-rewarding System in the Rat," *Neurosci Let*, 223, 125-128 (1997).

Gifford, A.N., et al., "Electrically Evoked Acetylcholine Relase from Hippocampal Silices is Inhibited by the Cannabinoid Receptor Agonist, WIN 55212-2 and is Potentiated by the Cannabinoid Antagonist, SR 141716A," *J Pharmacol Exp Ther*, 277, 1431-1436 (1996).

Compton, D.R., et al., "In Vivo Characterization of a Specific Cannabinoid Receptor Antagonist (SR141716A); Inhibition of Delta-9-Tetrahydrocannabinol-Induced Responses and Apparent Agonist Activity," *J Pharmacol Exp Ther*, 277, 586-594 (1996).

Mansbach, R.S., et al., "Effects of the Cannabinoid CB1 Receptor Antagonist SR141716A on the Behavior of Pigeons and Rats," *Psychopharmacology*, 124, 315-322 (1996).

Lichtman, A.H., et al., "Delta-9-Tetrahydrocannabinol Impairs Spatial Memory through a Cannabinoid Receptor Mechanism," *Psychopharmacology*, 126, 125-131 (1996).

Perio, A., et al., "Central Mediation of the Cannabinoid Cue: Activity of a Selective CB1 Antagonist, SR141716A," *Behavioral Pharmacology*, 7, 65-71 (1996).

Rinaldi-Carmona, M., et al., "Biochemical and Pharmacological Characteriszation of SR141716A, The First Potent and Selective Brain Cannabinoid Receptor Antagonist," *Life Sci*, 56, 1941-1947 (1995).

Pertwee, R., et al., "AM630, A Competititve Cannabinoid Receptor Antagonist," *Life Sci*, 56, 1949-1955 (1995).

Rinaldi-Carmona, M., et al., "SR141716A, a Patent and Selective Antagonist of the Brain Cannabinoid Receptor," *FEBS Letters*, 350, 240-244 (1994).

Dutta, A., et al., "The Synthesis and Pharmacological Evaluation of the Cannabinoid Antagonist SR 141716A", *Med. Chem. Rev.* 5, 54-62 (1994).

Drummond, J., et al., "Evaluation and Synthesis of Aminohydroxyisoxazoles and Pyrazoles as Potential Glycine Agonists," *J. Med. Chem*, 32, 2116-2128 (1989).

Murray, W., et al., "A Simple Regioselective Synthesis of Ethyl 1,5-Diarylpyrazole-3-carboxylates" *J. Heterocyclic Chem*, 26, 1389 (1989).

Dewey, W.L. "Cannabinoid Pharmacology," *Pharmacological Reviews*, 38(2)m 151-178 (1986).

Tewari, R.S., et al., "1,3-Dipolar Cycloaddition and Nucleophylic Substitution Reactions of C-Acetyl and C-Ethoxycarbonyl Derivative of Hydrazidoyl Bromides" *Tetrahedron*, 39(1) 129-136 (1983).

Birkofer, L. and K. Richtzenhain, "Silyl-Derivate von Pyrazol, Isoxazol und 1,2,3-Triazol" *Chem. Ber.* 112, 2829-2836 (1979).

Franke, H. et al., "Polare Cycloadditionen von elektronenreichen Mehrfach-bindungssystemen an 1,3,4-oxadiazolium-Salze: Synthese von 3aH-[1,3,4]Oxadiazolo[3,2-a]chinolinen" *Chem. Ber.* 112, 3623-3636 (1979).

Sucrow, W., et al., "Bimolekulare Cyclisierung von 2-(1-Methylhydrazino)maleinsaure-dimethylester" *Chem. Ber.* 112, 1712-1718 (1979).

Beardsley, P.M., et al., *Behavioural Pharmacology*, "Current Evidence Supporting a Role of Cannabinoid CB1 Receptor (CB1R) Antagonists as Potential Pharmacotherapies for Drug Abuse Disorders", vol. 16, pp. 275-296 (2005).

Bermudez-Siva, F., et al., *Journal of Pharmacology*, "Activation of Cannabinoid CB1 Receptors Induces Glucose Intolerance in Rats", vol. 531, pp. 282-284 (2006).

Brittain, H.G., *Drugs and the Pharmaceutical Sciences*, "Polymorphism in Pharmaceutical Solids", vol. 95, pp. 202-207 (1999).

Brodie, B.B., *Life Sciences*, "Rimonabant: The First Therapeutically Relevant Cannabinoid Antagonist", vol. 77, pp. 2339-2350 (2005).

Cao, X., et al., A Selective Cannabinoid CB1 Antagonist Increases Levodopa Responses in Parkinsonian Monkeys.

Chambers, A.P., et al., *Physiology & Behavior*, "Cannabinoid (CB1) Receptor Antagonist, AM 251, causes a Sustained Reduction of Daily Food Intake in the Rat", vol. 82, pp. 863-869 (2004).

Chaperon, F., et al., *Psychopharmacology*, "Involvement of Central Cannabinoid (CB1) Receptors in the Establishment of Place Conditioning in Rats", vol. 135, pp. 324-332 (198).

Cohen, C., et al., *Behavioural Pharmacology*, "SR141716, A Central Cannabinoid (CB!) Receptor Antagonist, Blocks the Motivational and Dopamine-Releasing Effects of Nicotine in Rats", vol. 13, pp. 451-463 (2002).

Croci, T., et al., *British Journal of Pharmacology*, "Role of Cannabinoid CB1 Receptors and Tumor Necrosis Factor—d in the Gut and Systemic Anti-Inflammatory Activity of SR 141716 (Rimonabant) in Rodents", vol. 140, pp. 115-122 (2003).

De Vries, T.J., et al., *TRENDS in Pharmacological Sciences*, "Cannabinoid CB1 Receptors Control Conditioned Drug Seeking", vol. 26 No. 8, pp. 420-426 (2005).

Di Marzo, V., *TRENDS in Pharmacological Sceinces*, "A Brief History of Cannabinoid and Endocannabinoid Pharmacology as Inspired by the Work of British Scientists", vol. 20 No. 20 pp. 1-7 (2006).

Di Marzo, V., et al., *The FASEB Journal*, "Enhanced Levels of Endogenous Cannabinoids in the Globus Pallidus are Associated with a Reduction in Movement in an Animal Model of Parkinson's Disease", vol. 14, pp. 1432-1438 (2000).

Fernandez, J.R., et al., *Current Opinion in Investigational Drugs*, "Rimonabant Sanofi-Synthelabo", vol. 5, No. 4, pp. 430-435 (2004).

Ferrer, B., et al., *European Journal of Neuroscience*, "Effects of Levodopa on Endocannabinoid Levels in Rat Basal Ganglia": Implications for the Treatment of Levodopa-Induced Dyskinesias, vol. 18, pp. 1607-1614 (2003).

Griebel, G., et al., *Biol. Psychiatry*, "Effects of the Cannabinoid CB1 Receptor antagonist Rimonabant in Models of Emotional Reactivity In Rodents", vol. 57, pp. 281-287 (2005).

Lange, J., et al., *Drug Discovery Today* "Medicinal Chemistry Strategies to CB1 Cannabinoid Receptor Antagonists", vol. 10, No. 10, pp. 693-702 (2005).

Le Foll, B., et al., *NeuroReport*, "Reimonabant, a CB1 Antagonist, Blocks Nicotine-Conditioned Place Preferences", vol. 15, No. 13, pp. 2139-2143 (2004).

Mansbach, R.S., et al., *Psychopharmacology*, "Effects of the Cannabinoid CB1 Receptor Antagonist SR141716A on the Behaviour of Pigeons and Rats", vol. 124, pp. 315-322 (1996).

Mas-Nieto, M., et al., *British Journal of Pharmacology*, "Reduction of Opiold Dependence by the CB1 antagonist SR141716A in Mice: Evaluation of the Interest in Pharmacology of Opiold Addiction", vol. 132, pp. 1809-1816 (2001).

Mechoulam, R., et al., *TRENDS in Pharmacological Sciences*, "Cannabis and Alcohol—A Close Friendship", vol. 24, No. 6, pp. 266-268 (2003).

Muccioli, G.G., et al., *Current Medicinal Chemistry*, "Current Knowledge on the Antagonists and Inverse Agonists of Cannabinoid Receptors", vol. 12, pp. 1361-1394 (2005).

Pagotto, U., et al., *Endocrine Reviews*, "The Emerging Role of the Endocannabinoid System in Endocrine Regulation and Energy Balance", vol. 27, No. 1, pp. 73-100 (2006).

Pagotto, U., et al., *Current Opinion in Endocrinology & Diabetes*, "the Role of the Endocannabinoid Pathway in Metabolism and Diabetes", vol. 13, pp. 171-178 (2006).

Poncelet, M., et al., *Psychopharmacology*, "Blockade of Cannabinoid (CB1) Receptors By SR 141716 Selectively Antagonizes Drug-Induced Reinstatement of Exploratory Behaviour in Gerbils", vol. 144, pp. 144-150 (1999).

Sanudo-Pena, M., et al, *Neuroscience Letters*, "Endogenous Cannabinoids As an Aversive or Counter-Rewarding System in the Rat", vol. 223, pp. 125-128 (1997).

Smith, R.A., et al., *IDrugs*, "Recent Advances in the Research and Development of CB1 Antagonists", vol. 8, No. 1, pp. 53-66 (2005).

Thakur, G.A., et al., *Mini-Reviews in Medicinal Chemistry*, "CB1 Cannabinoid Receptor Ligands", vol. 5, pp. 631-640 (2005).

Van Der Stelt, M., et al., *The FASEB Journal*, "A Role For Endocannabinoids in the Generation of Parkinsonism and Levodopa-Induced Dyskinesia in MPTP-Lesioned Non-Human Primate Models of Parkinson's Disease", vol. 19, pp. 1140-1142 (2005).

Van Gaal, L., et al., *Lancet*, "Effects of the Cannabinoid-1 Receptor Blocker Rimonabant on Weight Reduction and Cardiovascular Risk Factors in Overweight Patients: 1-year Experience from the RIO-Europe Study", vol. 365, pp. 1389-1397 (2005).

Witkin, J.M., et al., *TRENDS in Pharmacological Sciences*, "A Therapeutic Role for Cannabinoid CB1 Receptor Antagonists in Major Depressive Disorders", vol. 26, No. 12, pp. 609-617 (2005).

Wolff, M., et al., *European Journal of Pharmacology*, "SR141716A, A Cannabinoid CB1 Receptor Antagonist, Improves Memory in a Delayed Radial Maze Task", vol. 477, pp. 213-217 (2003).

Louis, C., et al., *Psychopharmacology*, "Surinabant, a New CB1 Receptor Antagonist, Displays Efficacy in Animal Models of Attention Deficit/Hyperactivity Disorder", vol. 30, S173, Abstract 77 (2005).

\* cited by examiner

CANNABINOID RECEPTOR LIGANDS AND USES THEREOF

FIELD OF THE INVENTION

The present invention relates to pyrazolo[1,5-a]pyrimidine compounds as cannabinoid receptor ligands, in particular CB1 receptor antagonists, and uses thereof for treating diseases, conditions and/or disorders modulated by cannabinoid receptor antagonists.

BACKGROUND

Obesity is a major public health concern because of its increasing prevalence and associated health risks. Obesity and overweight are generally defined by body mass index (BMI), which is correlated with total body fat and estimates the relative risk of disease. BMI is calculated by weight in kilograms divided by height in meters squared (kg/m$^2$). Overweight is typically defined as a BMI of 25–29.9 kg/m$^2$, and obesity is typically defined as a BMI of 30 kg/m$^2$. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

The increase in obesity is of concern because of the excessive health risks associated with obesity, including coronary heart disease, strokes, hypertension, type 2 diabetes mellitus, dyslipidemia, sleep apnea, osteoarthritis, gall bladder disease, depression, and certain forms of cancer (e.g., endometrial, breast, prostate, and colon). The negative health consequences of obesity make it the second leading cause of preventable death in the United States and impart a significant economic and psychosocial effect on society. See, McGinnis M, Foege W H., "Actual Causes of Death in the United States," *JAMA*, 270, 2207–12 (1993).

Obesity is now recognized as a chronic disease that requires treatment to reduce its associated health risks. Although weight loss is an important treatment outcome, one of the main goals of obesity management is to improve cardiovascular and metabolic values to reduce obesity-related morbidity and mortality. It has been shown that 5–10% loss of body weight can substantially improve metabolic values, such as blood glucose, blood pressure, and lipid concentrations. Hence, it is believed that a 5–10% intentional reduction in body weight may reduce morbidity and mortality.

Currently available prescription drugs for managing obesity generally reduce weight by inducing satiety or decreasing dietary fat absorption. Satiety is achieved by increasing synaptic levels of norepinephrine, serotonin, or both. For example, stimulation of serotonin receptor subtypes 1B, 1D, and 2C and 1- and 2-adrenergic receptors decreases food intake by regulating satiety. See, Bray G A, "The New Era of Drug Treatment. Pharmacologic Treatment of Obesity: Symposium Overview," *Obes Res.*, 3(suppl 4), 415s–7s (1995). Adrenergic agents (e.g., diethylpropion, benzphetamine, phendimetrazine, mazindol, and phentermine) act by modulating central norepinephrine and dopamine receptors through the promotion of catecholamine release. Older adrenergic weight-loss drugs (e.g., amphetamine, methamphetamine, and phenmetrazine), which strongly engage in dopamine pathways, are no longer recommended because of the risk of their abuse. Fenfluramine and dexfenfluramine, both serotonergic agents used to regulate appetite, are no longer available for use.

More recently, CB1 cannabinoid receptor antagonists/inverse agonists have been suggested as potential appetite suppressants. See, e.g., Arnone, M., et al., "Selective Inhibition of Sucrose and Ethanol Intake by SR141716, an Antagonist of Central Cannabinoid (CB1) Receptors," *Psychopharmacol*, 132, 104–106 (1997); Colombo, G., et al., "Appetite Suppression and Weight Loss after the Cannabinoid Antagonist SR141716," *Life Sci.*, 63, PL113–PL117 (1998); Simiand, J., et al., "SR141716, a CB1 Cannabinoid Receptor Antagonist, Selectively Reduces Sweet Food Intake in Marmose," *Behav. Pharmacol.*, 9, 179–181 (1998); and Chaperon, F., et al., "Involvement of Central Cannabinoid (CB1) Receptors in the Establishment of Place Conditioning in Rats," *Psychopharmacology*, 135, 324–332 (1998). For a review of cannabinoid CB1 and CB2 receptor modulators, see Pertwee, R. G., "Cannabinoid Receptor Ligands: Clinical and Neuropharmacological Considerations, Relevant to Future Drug Discovery and Development," *Exp. Opin. Invest. Drugs*, 9(7), 1553–1571 (2000).

Although investigations are on-going, there still exists a need for a more effective and safe therapeutic treatment for reducing or preventing weight-gain.

In addition to obesity, there also exists an unmet need for treatment of alcohol abuse. Alcoholism affects approximately 10.9 million men and 4.4 million women in the United States. Approximately 100,000 deaths per year have been attributed to alcohol abuse or dependence. Health risks associated with alcoholism include impaired motor control and decision making, cancer, liver disease, birth defects, heart disease, drug/drug interactions, pancreatitis and interpersonal problems. Studies have suggested that endogenous cannabinoid tone plays a critical role in the control of ethanol intake. The endogenous CB1 receptor antagonist SR-141716A has been shown to block voluntary ethanol intake in rats and mice. See, Arnone, M., et al., "Selective Inhibition of Sucrose and Ethanol Intake by SR141716, an Antagonist of Central Cannabinoid (CB1) Receptors," *Psychopharmacol*, 132, 104–106 (1997). For a review, see Hungund, B. L and B. S. Basavarajappa, "Are Anadamide and Cannabinoid Receptors involved in Ethanol Tolerance? A Review of the Evidence," *Alcohol & Alcoholism*. 35(2) 126–133, 2000.

Current treatments for alcohol abuse or dependence generally suffer from non-compliance or potential hepatotoxicity; therefore, there is a high unmet need for more effective treatment of alcohol abuse/dependence.

SUMMARY

The present invention provides compounds of Formula (I) that act as cannabinoid receptor ligands (in particular, CB1 receptor antagonists)

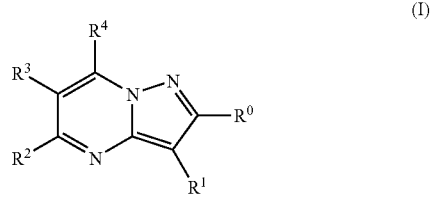

(I)

wherein $R^0$ is an optionally substituted heteroaryl or a substituted aryl (preferably, $R^0$ is a substituted phenyl, more preferably a phenyl substituted with one to three substituents independently selected from the group consisting of halo (preferably, chloro or fluoro), $(C_1–C_4)$alkoxy, $(C_1–C_4)$alkyl, halo-substituted $(C_1–C_4)$alkyl (preferably fluoro-substituted alkyl), and cyano, most preferably, $R^0$ is 2-chlorophenyl, 2-fluorophenyl, 2,4-dichlorophenyl, 2-fluoro-4-chlorophenyl, 2-chloro-4-fluorophenyl, or 2,4-difluorophenyl);

$R^1$ is an optionally substituted heteroaryl or a substituted aryl (preferably, $R^1$ is a substituted phenyl, more preferably a phenyl substituted with one to three substituents independently selected from the group consisting of halo (preferably, chloro or fluoro), $(C_1–C_4)$alkoxy, $(C_1–C_4)$alkyl, halo-substituted $(C_1–C_4)$alkyl (preferably fluoro-substituted alkyl), and cyano, most preferably, $R^1$ is 4-chlorophenyl or 4-fluorophenyl);

$R^2$ and $R^3$ are each independently hydrogen, halo, $(C_1–C_4)$alkyl, halo-substituted $(C_1–C_4)$alkyl, or $(C_1–C_4)$alkoxy;

$R^4$ is
(i) a group having Formula (IA) or Formula (IB)

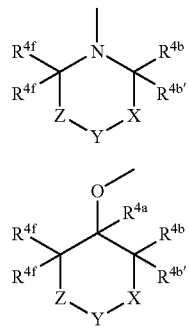

where $R^{4a}$ is hydrogen or $(C_1–C_3)$alkyl;

$R^{4b}$ and $R^{4b'}$ are each independently hydrogen, cyano, hydroxy, amino, $H_2NC(O)$—, or a chemical moiety selected from the group consisting of $(C_1–C_6)$alkyl, $(C_1–C_6)$alkoxy, acyloxy, acyl, $(C_1–C_3)$alkyl-O—C(O)—, $(C_1–C_4)$alkyl-NH—C(O)—, $(C_1–C_4)$alkyl)$_2$N—C(O)—, $(C_1–C_6)$alkylamino-, $((C_1–C_4)$alkyl)$_2$amino-, $(C_3–C_6)$cycloalkylamino-, acylamino-, aryl$(C_1–C_4)$alkylamino-, heteroaryl$(C_1–C_4)$alkylamino-, aryl, heteroaryl, a partially or fully saturated 3–6 membered heterocycle, and a partially or fully saturated carbocyclic ring, where the moiety is optionally substituted with one or more substituents, or either $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —$CH_2CH_2$— or —$C(R^{4c})(R^{4c'})$—, where $R^{4c}$ and $R^{4c'}$ are each independently hydrogen, cyano, hydroxy, amino, $H_2NC(O)$—, or a chemical moiety selected from the group consisting of $(C_1–C_6)$alkyl, $(C_1–C_6)$alkoxy, acyloxy, acyl, $(C_1–C_3)$alkyl-O—C(O)—, $(C_1–C_4)$alkyl-NH—C(O)—, $((C_1–C_4)$alkyl)$_2$N—C(O)—, $(C_1–C_6)$alkylamino-, di$(C_1–C_4)$alkylamino-, $(C_3–C_6)$cycloalkylamino-, acylamino-, aryl$(C_1–C_4)$alkylamino-, heteroaryl$(C_1–C_4)$alkylamino-, aryl, heteroaryl, a partially or fully saturated 3–6 membered heterocycle, and a partially or fully saturated 3–6 membered carbocyclic ring, where the moiety is optionally substituted with one or more substituents, or either $R^{4c}$ or $R^{4c'}$ taken together with $R^{4e}$, $R^{4e'}$, $R^{4f}$, or $R^{4f'}$ forms a bond, a methylene bridge or an ethylene bridge;

Y is oxygen, sulfur, —C(O)—, or —$C(R^{4d})(R^{4d'})$—, where $R^{4d}$ and $R^{4d'}$ are each independently hydrogen, cyano, hydroxy, amino, $H_2NC(O)$—, or a chemical moiety selected from the group consisting of $(C_1–C_6)$alkyl, $(C_1–C_6)$alkoxy, acyloxy, acyl, $(C_1–C_3)$alkyl-O—C(O)—, $(C_1–C_4)$alkyl-NH—C(O)—, $((C_1–C_4)$alkyl)$_2$N—C(O)—, $(C_1–C_6)$alkylamino-, di$(C_1–C_4)$alkylamino-, $(C_3–C_6)$cycloalkylamino-, acylamino-, aryl$(C_1–C_4)$alkylamino-, heteroaryl$(C_1–C_4)$alkylamino-, aryl, heteroaryl, a partially or fully saturated 3–6 membered heterocycle, and a partially or fully saturated 3–6 membered carbocyclic ring, where the moiety is optionally substituted with one or more substituents, or $R^{4d}$ and $R^{4d'}$ taken together form a partially or fully saturated, 3–6 membered heterocyclic ring, a 5–6 membered lactone ring, or a 4–6 membered lactam ring, where the heterocyclic ring, the lactone ring and the lactam ring are optionally substituted with one or more substituents and the lactone ring and the lactam ring optionally contain an additional heteroatom selected from oxygen, nitrogen or sulfur, or Y is —$NR^{4d''}$—, where $R^{4d''}$ is a hydrogen or a chemical moiety selected from the group consisting of $(C_1–C_6)$alkyl, $(C_3–C_6)$cycloalkyl, $(C_1–C_3)$alkylsulfonyl-, $(C_1–C_3)$alkylaminosulfonyl-, di$(C_1–C_3)$alkylaminosulfonyl-, acyl, $(C_1–C_6)$alkyl-O—C(O)—, aryl, and heteroaryl, where the moiety is optionally substituted with one or more substituents;

Z is a bond, —$CH_2CH_2$—, or —$C(R^{4e})(R^{4e'})$—, where $R^{4e}$ and $R^{4e'}$ are each independently hydrogen, cyano, hydroxy, amino, $H_2NC(O)$—, or a chemical moiety selected from the group consisting of $(C_1–C_6)$alkyl, $(C_1–C_6)$alkoxy, acyloxy, acyl, $(C_1–C_3)$alkyl-O—C(O)—, $(C_1–C_4)$alkyl-NH—C(O)—, $((C_1–C_4)$alkyl)$_2$N—C(O)—, $(C_1–C_6)$alkylamino-, di$(C_1–C_4)$alkylamino-, $(C_3–C_6)$cycloalkylamino-, acylamino-, aryl$(C_1–C_4)$alkylamino-, heteroaryl$(C_1–C_4)$alkylamino-, aryl, heteroaryl, a partially or fully saturated 3–6 membered heterocycle, and a partially or fully saturated 3–6 membered carbocyclic ring, where the moiety is optionally substituted with one or more substituents, or either $R^{4e}$ or $R^{4e'}$ taken together with $R^{4b}$, $R^{4b'}$, $R^{4c}$, or $R^{4c'}$ forms a bond, a methylene bridge or an ethylene bridge; and $R^{4f}$ and $R^{4f'}$ are each independently hydrogen, cyano, hydroxy, amino, $H_2NC(O)$—, or a chemical moiety selected from the group consisting of $(C_1–C_6)$alkyl, $(C_1–C_6)$alkoxy, acyloxy, acyl, $(C_1–C_3)$alkyl-O—C(O)—, $(C_1–C_4)$alkyl-NH—C(O)—, $((C_1–C_4)$alkyl)$_2$N—C(O)—, $(C_1–C_6)$alkylamino-, di$(C_1–C_4)$alkylamino-, $(C_3–C_6)$cycloalkylamino-, acylamino-, aryl$(C_1–C_4)$alkylamino-, heteroaryl$(C_1–C_4)$alkylamino-, aryl, heteroaryl, a partially or fully saturated 3–6 membered heterocycle, and a partially or fully saturated 3–6 membered carbocyclic ring, where the moiety is optionally substituted with one or more substituents, or either $R^{4f}$ or $R^{4f'}$ taken together with $R^{4b}$, $R^{4b'}$, $R^{4c}$, or $R^{4c'}$ forms a bond, a methylene bridge or an ethylene bridge;

(ii) —O—$R^5$, where $R^5$ taken together with $R^3$ forms a 5- to 6-membered partially saturated heterocyclic ring optionally containing an additional oxygen, or a 5-membered heteroaryl, the heterocyclic ring and the heteroaryl being optionally substituted with one or more substituents;

a pharmaceutically acceptable salt thereof, a prodrug of the compound or the salt, or a solvate or hydrate of the compound, the salt or the prodrug.

In a preferred embodiment of the present invention, a compound of Formula (II) is provided.

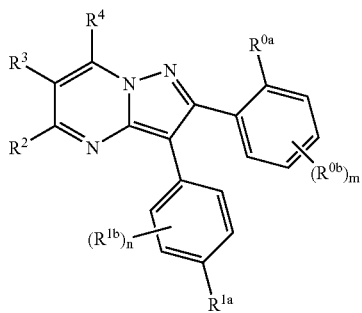

(II)

wherein $R^{0a}$, $R^{0b}$, $R^{1a}$, and $R^{1b}$ are each independently halo, $(C_1-C_4)$alkoxy, $(C_1-C_4)$alkyl, halo-substituted $(C_1-C_4)$alkyl, or cyano;

n and m are each independently 0, 1 or 2;

$R^2$ and $R^3$ are each independently hydrogen, halo, $(C_1-C_4)$alkyl, halo-substituted $(C_1-C_4)$alkyl, or $(C_1-C_4)$alkoxy;

$R^4$ is (i) a group having Formula (IA) or Formula (IB)

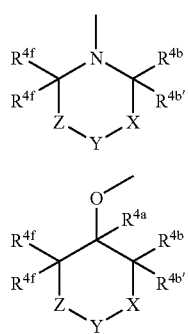

IA

IB where $R^{4a}$ is hydrogen or $(C_1-C_3)$alkyl;

$R^{4b}$ and $R^{4b'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3–6 membered partially or fully saturated heterocycle, and a partially or fully saturated carbocyclic ring, where the moiety is optionally substituted with one or more substituents, or either $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —$CH_2CH_2$— or —$C(R^{4c})(R^{4c'})$—, where $R^{4c}$ and $R^{4c'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl)$_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a 3–6 membered partially or fully saturated heterocycle, and a 3–6 membered partially or fully saturated carbocyclic ring, where the moiety is optionally substituted with one or more substituents, or either $R^{4c}$ or $R^{4c'}$ taken together with $R^{4e}$, $R^{e'}$, $R^{4f}$, or $R^{4f'}$ forms a bond, a methylene bridge or an ethylene bridge;

Y is oxygen, sulfur, —C(O)—, or —$C(R^{4d})(R^{4d'})$—, where $R^{4d}$ and $R^{4d'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl)$_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a 3–6 membered partially or fully saturated heterocycle, and a 3–6 membered partially or fully saturated carbocyclic ring, where the moiety is optionally substituted with one or more substituents, or $R^{4d}$ and $R^{4d'}$ taken together form a 3–6 membered partially or fully saturated carbocyclic ring, a 3–6 membered partially or fully saturated heterocyclic ring, a 5–6 membered lactone ring, or a 4–6 membered lactam ring, where said carbocyclic ring, said heterocyclic ring, said lactone ring and said lactam ring are optionally substituted with one or more substituents and said lactone ring and said lactam ring optionally contain an additional heteroatom selected from oxygen, nitrogen or sulfur, or Y is —$NR^{4d''}$—, where $R^{4d''}$ is a hydrogen or a chemical moiety selected from the group consisting of $(C_1-C_6)$alkyl, $(C_3-C_6)$cycloalkyl, $(C_1-C_3)$alkylsulfonyl-, $(C_1-C_3)$alkylaminosulfonyl-, di$(C_1-C_3)$alkylaminosulfonyl-, acyl, $(C_1-C_6)$alkyl-O—C(O)—, aryl, and heteroaryl, where the moiety is optionally substituted with one or more substituents;

Z is a bond, —$CH_2CH_2$—, or —$C(R^{4e})(R^{4e'})$—, where $R^{4e}$ and $R^{4e'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl)$_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a 3–6 membered partially or fully saturated heterocyclic ring, and a 3–6 membered partially or fully saturated carbocyclic ring, where the moiety is optionally substituted with one or more substituents, or either $R^{4e}$ or $R^{4e'}$ taken together with $R^{4b}$, $R^{4b'}$, $R^{4c}$, or $R^{4c'}$ forms a bond, a methylene bridge or an ethylene bridge; and $R^{4f}$ and $R^{4f'}$ are each independently hydrogen, cyano, hydroxy, amino, $H_2NC(O)$—, or a chemical moiety selected from the group consisting of $(C_1-C_6)$alkyl, ($C_1$–$C_6$)alkoxy, acyloxy, acyl, ($C_1$–$C_3$)alkyl-O—C(O)—, ($C_1$–$C_4$)alkyl-NH—C(O)—, (($C_1$–$C_4$)alkyl)$_2$N—C(O)—, ($C_1$–$C_6$)alkylamino-, di($C_1$–$C_4$)alkylamino-, ($C_3$–$C_6$)cycloalkylamino-, acylamino-, aryl($C_1$–$C_4$)alkylamino-, heteroaryl($C_1$–$C_4$)alkylamino-, aryl, heteroaryl, a 3–6 membered partially or fully saturated heterocycle, and a 3–6 membered partially or fully saturated carbocyclic ring, where the moiety is optionally substituted with one or more substituents, or either $R^{4f}$ or $R^{4f'}$ taken together with $R^{4b}$, $R^{4b'}$, $R^{4c}$, or $R^{4c'}$ forms a bond, a methylene bridge or an ethylene bridge;

(ii) a group having Formula (IC)

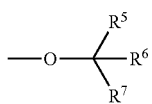

IC where $R^5$ and $R^6$ are each independently hydrogen or ($C_1$–$C_4$)alkyl, and $R^7$ is an optionally substituted ($C_1$–$C_4$)alkyl-, or an optionally substituted 4–6 membered partially or fully saturated heterocylic ring containing 1 to 2 heteroatoms independently selected from oxygen, sulfur or nitrogen, or $R^5$ and $R^6$ or $R^5$ and $R^7$ taken together form a 5–6 membered lactone, 4–6 membered lactam, or a 4–6 membered partially or fully saturated heterocycle containing 1 to 2 heteroatoms independently selected from oxygen, sulfur or nitrogen, where said lactone, said lactam and said heterocycle are optionally substituted with one or more substituents, or $R^5$, $R^6$ or $R^7$ taken together with $R^3$ forms a 5- to 6-membered partially saturated heterocyclic ring or a 5- to 6-membered heteroaryl, where said heterocyclic ring and said heteroaryl optionally contain an additional oxygen and are optionally substituted with one or more substituents;

(iii) an amino group having attached thereto at least one chemical moiety selected from the group consisting of ($C_1$–$C_8$)alkyl, aryl($C_1$–$C_4$)alkyl, a 3–8 membered partially or fully saturated carbocyclic ring, hydroxy($C_1$–$C_6$)alkyl, ($C_1$–$C_3$)alkoxy($C_1$–$C_6$)alkyl, heteroaryl($C_1$–$C_3$)alkyl, and a fully or partially saturated heterocycle, where said chemical moiety is optionally substituted with one or more substituents;

(iv) an ($C_1$–$C_6$)alkyl group having attached thereto at least one chemical moiety selected from the group consisting of hydroxy, ($C_1$–$C_6$)alkoxy, amino, ($C_1$–$C_6$)alkylamino, di(($C_1$–$C_6$)alkyl)amino ($C_1$–$C_3$)alkylsulfonyl, ($C_1$–$C_3$)alkylsulfamyl, di(($C_1$–$C_3$)alkyl)sulfamyl, acyloxy, a fully or partially saturated heterocycle, and a fully or partially saturated carbocyclic ring, where said chemical moiety is optionally substituted with one or more substituents; or (v) an optionally substituted aryl or optionally substituted heteroaryl;

a pharmaceutically acceptable salt thereof, or a solvate or hydrate of the compound or the salt.

A preferred compound of the present invention is a compound of Formula (I) or (II) where $R^4$ is a group of Formula (IA). Preferably, $R^{4b}$ and $R^{4b'}$ are each independently hydrogen, $H_2NC(O)$—, or a chemical moiety selected from the group consisting of ($C_1$–$C_6$)alkyl, acyl, ($C_1$–$C_3$)alkyl-O—C(O)—, ($C_1$–$C_4$)alkyl-NH—C(O)—, ($C_1$–$C_4$)alkyl)$_2$N—C(O)—, aryl, heteroaryl, a partially or fully saturated 3–6 membered heterocycle, and a partially or fully saturated carbocyclic ring, where the moiety is optionally substituted, or $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —$CH_2CH_2$— or —$C(R^{4c})(R^{4c'})$—, where $R^{4c}$ is hydrogen, cyano, hydroxy, amino, $H_2NC(O)$—, or a chemical moiety selected from the group consisting of ($C_1$–$C_6$)alkyl, ($C_1$–$C_6$)alkoxy, acyloxy, acyl, ($C_1$–$C_3$)alkyl-C(O)—, ($C_1$–$C_4$)alkyl-NH—C(O)—, ($C_1$–$C_4$)alkyl)$_2$N—C(O)—, ($C_1$–$C_6$)alkylamino-, (($C_1$–$C_4$)alkyl)$_2$amino-, ($C_3$–$C_6$)cycloalkylamino-, acylamino-, aryl($C_1$–$C_4$)alkylamino-, heteroaryl($C_1$–$C_4$)alkylamino-, aryl, heteroaryl, a partially or fully saturated 3–6 membered heterocycle, and a partially or fully saturated carbocyclic ring, where the moiety is optionally substituted, or $R^{4c}$ taken together with $R^{4e}$, $R^{4e'}$, $R^{4f}$, or $R^{4f'}$ forms a bond, a methylene bridge, or an ethylene bridge, and $R^{4c'}$ is hydrogen, $H_2NC(O)$—, or a chemical moiety selected from the group consisting of ($C_1$–$C_6$)alkyl, acyl, ($C_1$–$C_3$)alkyl-O—C(O)—, ($C_1$–$C_4$)alkyl-NH—C(O)—, ($C_1$–$C_4$)alkyl)$_2$N—C(O)—, aryl, heteroaryl, a partially or fully saturated 3–6 membered heterocycle, and a partially or fully saturated carbocyclic ring, where the moiety is optionally substituted, or $R^{4c'}$ taken together with $R^{4e}$, $R^{4e'}$, $R^{4f}$ or $R^{4f'}$ forms a bond, a methylene bridge, or an ethylene bridge;

Y is oxygen, sulfur, —C(O)—, or —$C(R^{4d})(R^{4d'})$—, where $R^{4d}$ is hydrogen, cyano, hydroxy, amino, $H_2NC(O)$—, or a chemical moiety selected from the group consisting of ($C_1$–$C_6$)alkyl, ($C_1$–$C_6$)alkoxy, acyloxy, acyl, ($C_1$–$C_3$)alkyl-O—C(O)—, ($C_1$–$C_4$)alkyl-NH—C(O)—, ($C_1$–$C_4$)alkyl)$_2$N—C(O)—, ($C_1$–$C_6$)alkylamino-, (($C_1$–$C_4$)alkyl)$_2$amino-, ($C_3$–$C_6$)cycloalkylamino-, acylamino-, aryl($C_1$–$C_4$)alkylamino-, heteroaryl($C_1$–$C_4$)alkylamino-, aryl, heteroaryl, a partially or fully saturated 3–6 membered heterocycle, and a partially or fully saturated carbocyclic ring, where the moiety is optionally substituted, and $R^{4d'}$ is hydrogen, $H_2NC(O)$—, or a chemical moiety selected from the group consisting of ($C_1$–$C_6$)alkyl, acyl, ($C_1$–$C_3$)alkyl-O—C(O)—, ($C_1$–$C_4$)alkyl-NH—C(O)—, ($C_1$–$C_4$)alkyl)$_2$N—C(O)—, aryl, heteroaryl, a partially or fully saturated 3–6 membered heterocycle, and a partially or fully saturated carbocyclic ring, where the moiety is optionally substituted, or $R^{4d}$ and $R^{4d'}$ taken together form a partially or fully saturated, 3–6 membered heterocyclic ring, a 5–6 membered lactone ring, or a 4–6 membered lactam ring, where the heterocyclic ring, the lactone ring and the lactam ring are optionally substituted and the lactone ring and the lactam ring optionally contain an additional heteroatom selected from oxygen, nitrogen or sulfur, or Y is —$NR^{4d''}$—, where $R^{4d''}$ is a hydrogen or a chemical moiety selected from the group consisting of ($C_1$–$C_6$)alkyl, ($C_3$–$C_6$)cycloalkyl, ($C_1$–$C_3$)alkylsulfonyl-, ($C_1$–$C_3$)alkylaminosulfonyl-, di($C_1$–$C_3$)alkylaminosulfonyl-, acyl, ($C_1$–$C_6$)alkyl-O—C(O)—, aryl, and heteroaryl, where the moiety is optionally substituted;

Z is a bond, —$CH_2CH_2$—, or —$C(R^{4e})(R^{4e'})$—, where $R^{4e}$ is hydrogen, cyano, hydroxy, amino, $H_2NC(O)$—, or a chemical moiety selected from the group consisting of ($C_1$–$C_6$)alkyl, ($C_1$–$C_6$)alkoxy, acyloxy, acyl, ($C_1$–$C_3$)alkyl-O—C(O)—, ($C_1$–$C_4$)alkyl-NH—C(O)—, ($C_1$–$C_4$)alkyl)$_2$N—C(O)—, ($C_1$–$C_6$)alkylamino-, (($C_1$–$C_4$)alkyl)$_2$amino-, ($C_3$–$C_6$)cycloalkylamino-, acylamino-, aryl($C_1$–$C_4$)alkylamino-, heteroaryl($C_1$–$C_4$)alkylamino-, aryl, heteroaryl, a partially or fully saturated 3–6 membered heterocycle, and a partially or fully saturated carbocyclic ring, where the moiety is optionally substituted, or $R^{4e}$ taken together with $R^{4b}$, $R^{4b'}$, $R^{4c}$, or $R^{4c'}$ forms a bond, a methylene bridge, or an ethylene bridge, and $R^{4e'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a partially or fully saturated 3–6 membered heterocycle, and a partially or fully saturated carbocyclic ring, where the moiety is optionally substituted, or $R^{4e'}$ taken together with $R^{4b}$, $R^{4b'}$, $R^{4c}$, or $R^{4c'}$ forms a bond, a methylene bridge, or an ethylene bridge; and $R^{4f}$ and $R^{4f'}$ are each independently hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a partially or fully saturated 3–6 membered heterocycle, and a partially or fully saturated carbocyclic ring, where the moiety is optionally substituted, or $R^f$ or $R^{f'}$ taken together with $R^{4b}$, $R^{4b'}$, $R^{4c}$, or $R^{4c'}$ forms a bond, a methylene bridge, or an ethylene bridge;

a pharmaceutically acceptable salt thereof, a prodrug of the compound or the salt, or a solvate or hydrate of the compound, the salt or the prodrug.

Preferably, $R^{4b}$ is hydrogen, an optionally substituted $(C_1-C_3)$alkyl, or taken together with $R^{4e}$, $R^{4e'}$, $R^{4f}$, or $R^{4f'}$ forms a bond, a methylene bridge, or an ethylene bridge; $R^{4b'}$ is hydrogen, an optionally substituted $(C_1-C_3)$alkyl, or taken together with $R^{4e}$, $R^{4e'}$, $R^{4f}$, or $R^{f'}$ forms a bond, a methylene bridge, or an ethylene bridge; $R^{4f}$ is hydrogen, an optionally substituted $(C_1-C_3)$alkyl, or taken together with $R^{4b}$, $R^{4b'}$, $R^{4c}$, or $R^{4c'}$ forms a bond, a methylene bridge, or an ethylene bridge; and $R^{f'}$ is hydrogen, an optionally substituted $(C_1-C_3)$alkyl, or taken together with $R^{4b}$, $R^{4b'}$, $R^{4c}$, or $R^{4c'}$ forms a bond, a methylene bridge, or an ethylene bridge, and even more preferably, $R^{4b}$, $R^{4b'}$, $R^{4f}$, and $R^{4f'}$ are all hydrogen.

When Y is —$NR^{4d''}$—, then $R^{4d''}$ is preferably a hydrogen or a chemical moiety selected from the group consisting of $(C_1-C_6)$alkyl, $(C_3-C_6)$cycloalkyl, $(C_1-C_3)$alkylsulfonyl, $(C_1-C_3)$alkylaminosulfonyl, di$(C_1-C_3)$alkylaminosulfonyl, acyl, $(C_1-C_6)$alkyl-O—C(O)—, aryl, and heteroaryl, where the moiety is optionally substituted (more preferably, $R^{4d''}$ is a hydrogen or a chemical moiety selected from the group consisting of $(C_1-C_3)$alkylsulfonyl, $(C_1-C_3)$alkylaminosulfonyl, di$(C_1-C_3)$alkylaminosulfonyl, acyl, $(C_1-C_6)$alkyl-O—C(O)—, and heteroaryl, where the moiety is optionally substituted (preferably the $(C_1-C_3)$alkylsulfonyl, $(C_1-C_3)$alkylaminosulfonyl, di$(C_1-C_3)$alkylaminosulfonyl, acyl, and $(C_1-C_6)$alkyl-O—C(O)— are optionally substituted with 1–3 fluorines, and the heteroaryl is optionally substituted with 1 to 2 substituents independently selected from the group consisting of chloro, fluoro, $(C_1-C_3)$alkoxy, $(C_1-C_3)$alkyl, and fluoro-substituted $(C_1-C_3)$alkyl);

X is —$C(R^{4c})(R^{4c'})$—, where $R^{4c}$ and $R^{4c'}$ are each independently hydrogen, $H_2NC(O)$—, an optionally substituted $(C_1-C_6)$alkyl, $(C_1-C_4)$alkyl-NH—C(O)—, or $((C_1-C_4)$alkyl)$_2$N—C(O)—, or either $R^{4c}$ or $R^{4c'}$ taken together with $R^{4e}$, $R^{4e'}$, $R^{4f}$, or $R^{f'}$ forms a bond, a methylene bridge or an ethylene bridge; and Z is —$C(R^{4e})(R^{4e'})$—, where $R^{4e}$ and $R^{4e'}$ are each independently hydrogen, $H_2NC(O)$—, an optionally substituted $(C_1-C_6)$alkyl, $(C_1-C_4)$alkyl-NH—C(O)—, or $((C_1-C_4)$alkyl)$_2$N—C(O)—, or either $R^{4e}$ or $R^{4e'}$ taken together with $R^{4b}$, $R^{4b'}$, $R^{4c}$, or $R^{4c'}$ forms a bond, a methylene bridge or an ethylene bridge.

Preferred compounds include: 3-(4-chlorophenyl)-2-(2-chlorophenyl)-5-methyl-7-(4-methylpiperazin-1-yl)-pyrazolo[1,5-a]pyrimidine; 3-(4-chlorophenyl)-2-(2-chlorophenyl)-5-methyl-7-(4-pyrimidin-2-yl-piperazin-1-yl)-pyrazolo[1,5-a]pyrimidine; 3-(4-chloro-phenyl)-2-(2-chlorophenyl)-7-[(1S,4S)-5-methanesulfonyl-2,5-diazabicyclo[2.2.1]hept-2-yl]-5-methylpyrazolo[1,5-a]pyrimidine; 3-(4-chlorophenyl)-2-(2-chlorophenyl)-5-methyl-7-[4-(propane-2-sulfonyl)-piperazin-1-yl]-pyrazolo[1,5-a]pyrimidine; 3-(4-chlorophenyl)-2-(2-chlorophenyl)-7-(4-ethanesulfonyl-piperazin-1-yl)-5-methylpyrazolo[1,5-a]pyrimidine; 3-(4-chlorophenyl)-2-(2-chlorophenyl)-7-(4-methanesulfonylpiperazin-1-yl)-5-methylpyrazolo[1,5-a]pyrimidine; 1-{4-[3-(4-chlorophenyl)-2-(2-chlorophenyl)-5-methylpyrazolo[1,5-a]pyrimidin-7-yl]-piperazin-1-yl}-ethanone; 4-[3-(4-chlorophenyl)-2-(2-chlorophenyl)-5-methylpyrazolo[1,5-a]pyrimidin-7-yl]-piperazine-1-carboxylic acid tert-butyl ester; 3-(4-chlorophenyl)-2-(2-chlorophenyl)-5-methyl-7-[(1S,4S)-5-(propane-2-sulfonyl)-2,5-diazabicyclo[2.2.1]hept-2-yl]-pyrazolo[1,5-a]pyrimidine; 1-{(1S,4S)-5-[3-(4-chlorophenyl)-2-(2-chlorophenyl)-5-methylpyrazolo[1,5-a]pyrimidin-7-yl]-2,5-diazabicyclo[2.2.1]hept-2-yl}-ethanone; and (1S,4S)-5-[3-(4-chlorophenyl)-2-(2-chlorophenyl)-5-methylpyrazolo[1,5-a]pyrimidin-7-yl]-2,5-diazabicyclo[2.2.1]heptane-2-carboxylic acid tert-butyl ester; a pharmaceutically acceptable salt thereof, or a solvate or hydrate of said compound or said salt.

When Y is —$C(R^{4d})(R^{4d'})$—, then $R^{4d}$ is preferably hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3–6 membered heterocycle, and a partially or fully saturated carbocyclic ring, where the moiety is optionally substituted (preferably, $R^{4d}$ is amino, $(C_1-C_6)$alkylamino, di$(C_1-C_4)$alkylamino, $(C_3-C_6)$cycloalkylamino, acylamino, aryl$(C_1-C_4)$alkylamino-, or heteroaryl$(C_1-C_4)$alkylamino, more preferably, $R^{4d}$ is amino, $(C_1-C_6)$alkylamino, di$(C_1-C_4)$alkylamino, $(C_3-C_6)$cycloalkylamino), and $R^{4d'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a partially or fully saturated 3–6 membered heterocycle, and a partially or fully saturated carbocyclic ring, where the moiety is optionally substituted (preferably, $R^{4d'}$ is $(C_1-C_6)$alkyl, $H_2NC(O)$—, $(C_1-C_4)$alkyl-NH—C(O)—, or $((C_1-C_4)$alkyl)$_2$N—C(O)—, or aryl, more preferably, $R^{4d'}$ is $H_2NC(O)$—, $(C_1-C_4)$alkyl-NH—C(O)—, or $((C_1-C_4)$alkyl)$_2$N—C(O)—), or $R^{4d}$ and $R^{4d'}$ taken together form a partially or fully saturated, 3–6 membered heterocyclic ring, a 5–6 membered lactone ring, or a 4–6 membered lactam ring, where the heterocyclic ring, the lactone ring and the lactam ring are optionally substituted and the lactone ring and the lactam ring optionally contain an additional heteroatom selected from oxygen, nitrogen or sulfur;

X is a bond or —$C(R^{4c})(R^{4c'})$—, where $R^{4c}$ and $R^{4c'}$ are each hydrogen; and Z is a bond or —$C(R^{4e})(R^{4e'})$—, where $R^{4e}$ and $R^{4e'}$ are each hydrogen.

Preferred compounds include: 1-[3-(4-chlorophenyl)-2-(2-chlorophenyl)-pyrazolo[1,5-a]pyrimidin-7-yl]-4-ethylaminopiperidine-4-carboxylic acid amide; 1-[3-(4-chlorophenyl)-2-(2-chlorophenyl)-pyrazolo[1,5-a]pyrimidin-7-yl]-4-isopropylaminopiperidine-4-carboxylic acid amide;

1-[3-(4-chlorophenyl)-2-(2-chlorophenyl)-pyrazolo[1,5-a]pyrimidin-7-yl]-3-ethylaminoazetidine-3-carboxylic acid amide; 1-[3-(4-chlorophenyl)-2-(2-chlorophenyl)-6-methylpyrazolo[1,5-a]pyrimidin-7-yl]-3-ethylaminoazetidine-3-carboxylic acid amide; 1-[3-(4-chlorophenyl)-2-(2-chlorophenyl)-5,6-dimethylpyrazolo[1,5-a]pyrimidin-7-yl]-3-ethylaminoazetidine-3-carboxylic acid amide; 1-[3-(4-chlorophenyl)-2-(2-chlorophenyl)-pyrazolo[1,5-a]pyrimidin-7-yl]-3-methylaminoazetidine-3-carboxylic acid amide; 1-[3-(4-chlorophenyl)-2-(2-chlorophenyl)-5-methylpyrazolo[1,5-a]pyrimidin-7-yl]-3-ethylaminoazetidine-3-carboxylic acid amide; 1-[3-(4-chlorophenyl)-2-(2-chlorophenyl)-6-methylpyrazolo[1,5-a]pyrimidin-7-yl]-3-methylaminoazetidine-3-carboxylic acid amide; and 1-[3-(4-chlorophenyl)-2-(2-chlorophenyl)-6-methylpyrazolo[1,5-a]pyrimidin-7-yl]-4-ethylaminopiperidine-4-carboxylic acid amide; a pharmaceutically acceptable salt thereof or a solvate or hydrate of said compound or said salt.

More preferred compounds include: 1-[3-(4-chlorophenyl)-2-(2-chlorophenyl)-pyrazolo[1,5-a]pyrimidin-7-yl]-4-isopropylaminopiperidine-4-carboxylic acid amide; 1-[3-(4-chlorophenyl)-2-(2-chlorophenyl)-pyrazolo[1,5-a]pyrimidin-7-yl]-3-ethylaminoazetidine-3-carboxylic acid amide; 1-[3-(4-chlorophenyl)-2-(2-chlorophenyl)-pyrazolo[1,5-a]pyrimidin-7-yl]-3-ethylaminoazetidine-3-carboxylic acid amide; and 1-[3-(4-chlorophenyl)-2-(2-chlorophenyl)-pyrazolo[1,5-a]pyrimidin-7-yl]-3-methylaminoazetidine-3-carboxylic acid amide; a pharmaceutically acceptable salt thereof or a solvate or hydrate of said compound or said salt.

In another preferred embodiment, a compound of Formula (I) or (II) is provided where Y is —C($R^{4d}$)($R^{4d'}$)—, $R^{4b}$, $R^{4b'}$, $R^{4f}$, and $R^{4f'}$ are all hydrogen; $R^{4d}$ is hydrogen, hydroxy, amino, or a chemical moiety selected from the group consisting of ($C_1$–$C_6$)alkyl, ($C_1$–$C_6$)alkoxy, acyloxy, acyl, ($C_1$–$C_3$)alkyl-O—C(O)—, ($C_1$–$C_6$)alkylamino-, and di($C_1$–$C_4$)alkylamino-, where the moiety is optionally substituted (preferably, $R^{4d}$ is hydrogen, hydroxy, amino, or a chemical moiety selected from the group consisting of ($C_1$–$C_6$)alkoxy, acyl, ($C_1$–$C_6$)alkylamino-, and di($C_1$–$C_4$)alkylamino-); and $R^{4d'}$ is hydrogen, or a chemical moiety selected from the group consisting of ($C_1$–$C_6$)alkyl, aryl and heteroaryl, where the moiety is optionally substituted (preferably, $R^{4d'}$ is hydrogen, or a chemical moiety selected from the group consisting of ($C_1$–$C_6$)alkyl and aryl, where the moiety is optionally substituted). In this embodiment, X is preferably —C($R^{4c}$)($R^{4c'}$)—, where $R^{4c}$ and $R^{4c'}$ are each independently hydrogen or an optionally substituted ($C_1$–$C_6$)alkyl, or either $R^{4c}$ or $R^{4c'}$ taken together with $R^{4e}$ or $R^{4e'}$ forms a bond, a methylene bridge or an ethylene bridge (preferably, $R^{4c}$ and $R^{4c'}$ are each hydrogen or either $R^{4c}$ or $R^{4c'}$ taken together with $R^{4e}$ or $R^{4e'}$, forms a bond); and Z is preferably —C($R^{4e}$)($R^{4e'}$)—, where $R^{4e}$ and $R^{4e'}$ are each independently hydrogen or an optionally substituted ($C_1$–$C_6$)alkyl, or either $R^{4e}$ or $R^{4e'}$ taken together with $R^{4c}$ or $R^{4c'}$ forms a bond, a methylene bridge or an ethylene bridge (preferably, $R^{4e}$ and $R^{4e'}$ are each hydrogen or either $R^{4e}$ or $R^{4e'}$ taken together with $R^{4c}$ or $R^{4c'}$ forms a bond).

Preferred compounds include: 1-{1-[3-(4-chlorophenyl)-2-(2-chlorophenyl)-5-methyl pyrazolo[1,5-a]pyrimidin-7-yl]-4-phenylpiperidin-4-yl}-ethanone; 3-[3-(4-chlorophenyl)-2-(2-chlorophenyl)-5-methylpyrazolo[1,5-a]pyrimidin-7-yl]-3-(1α,5α,6α)-azabicyclo[3.1.0]hex-6-ylamine; 1-[3-(4-chlorophenyl)-2-(2-chlorophenyl)-5-methylpyrazolo[1,5-a]pyrimidin-7-yl]-4-(4-fluorophenyl)-piperidin-4-ol; and 4-benzyl-1-[3-(4-chlorophenyl)-2-(2-chlorophenyl)-5-methylpyrazolo[1,5-a]pyrimidin-7-yl]-piperidin-4-ol; a pharmaceutically acceptable salt thereof, or a solvate or hydrate of said compound or said salt.

In yet another preferred embodiment, a compound of Formula (I) or (II) is provided where Y is —C($R^{4d}$)($R^{4d'}$)—, $R^{4b}$, $R^{4b'}$, $R^{4f}$, and $R^{4f'}$ are all hydrogen; and $R^{4d}$ and $R^{4d'}$ taken together form a partially or fully saturated 3–6 membered heterocyclic ring, a 5–6 membered lactone ring, or a 4–6 membered lactam ring, where the heterocyclic ring, the lactone ring and the lactam ring are optionally substituted and the lactone ring or the lactam ring optionally contains an additional heteroatom selected from oxygen, nitrogen or sulfur (preferably, $R^{4d}$ and $R^{4d'}$ taken together form a 5–6 membered lactam ring, where the lactam ring is optionally substituted and optionally contains an additional heteroatom selected from nitrogen or oxygen). In this embodiment, X is preferably a bond, —CH$_2$CH$_2$— or —C($R^{4c}$)($R^{4c'}$)—, where $R^{4c}$ and $R^{4c'}$ are each independently hydrogen or an optionally substituted ($C_1$–$C_6$)alkyl, or either $R^{4c}$ or $R^{4c'}$ taken together with $R^{4e}$ or $R^{4e'}$ forms a bond, a methylene bridge or an ethylene bridge (more preferably, X is a bond or —C($R^{4c}$)($R^{4c'}$)—, where $R^{4c}$ and $R^{4c'}$ are each hydrogen); and Z is preferably a bond, —CH$_2$CH$_2$— or —C($R^{4e}$)($R^{4e'}$)—, where $R^{4e}$ and $R^{4e'}$ are each independently hydrogen or an optionally substituted ($C_1$–$C_6$)alkyl, or either $R^{4e}$ or $R^{4e'}$ taken together with $R^{4c}$ or $R^{4c'}$ forms a bond, a methylene bridge or an ethylene bridge (more preferably, Z is a bond or —C($R^{4e}$)($R^{4e'}$)—, where $R^{4e}$ and $R^{4e'}$ are each hydrogen).

Preferred compounds include: 8-[3-(4-chlorophenyl)-2-(2-chlorophenyl)-5-methylpyrazolo[1,5-a]pyrimidin-7-yl]-1-isopropyl-1,3,8-triazaspiro[4.5]decan-4-one; and 2-[3-(4-chlorophenyl)-2-(2-chlorophenyl)-5-methylpyrazolo[1,5-a]pyrimidin-7-yl]-5-methyl-2,5,7-triazaspiro[3.4]octan-8-one; a pharmaceutically acceptable salt thereof or a solvate or hydrate of said compound or said salt. Even more preferred is 8-[3-(4-chlorophenyl)-2-(2-chlorophenyl)-pyrazolo[1,5-a]pyrimidin-7-yl]-1-isopropyl-1,3,8-triazaspiro[4.5]decan-4-one.

Another preferred compound of the present invention is a compound of Formula (I) or (II) where $R^4$ is a group of Formula (IB) where where $R^{4a}$ is as defined above, $R^{4b}$ is hydrogen, cyano, hydroxy, amino, H$_2$NC(O)—, or a chemical moiety selected from the group consisting of ($C_1$–$C_6$)alkyl, ($C_1$–$C_6$)alkoxy, acyloxy, acyl, ($C_1$–$C_3$)alkyl-O—C(O)—, ($C_1$–$C_4$)alkyl-NH—C(O)—, ($C_1$–$C_4$)alkyl)$_2$N—C(O)—, ($C_1$–$C_6$)alkylamino-, (($C_1$–$C_4$)alkyl)$_2$amino-, ($C_3$–$C_6$)cycloalkylamino-, acylamino-, aryl($C_1$–$C_4$)alkylamino-, heteroaryl($C_1$–$C_4$)alkylamino-, aryl, heteroaryl, a partially or fully saturated 3–6 membered heterocycle, and a partially or fully saturated carbocyclic ring, where the moiety is optionally substituted, $R^{4b'}$ is hydrogen, H$_2$NC(O)—, or a chemical moiety selected from the group consisting of ($C_1$–$C_6$)alkyl, acyl, ($C_1$–$C_3$)alkyl-O—C(O)—, ($C_1$–$C_4$)alkyl-NH—C(O)—, ($C_1$–$C_4$)alkyl)$_2$N—C(O)—, aryl, heteroaryl, a partially or fully saturated 3–6 membered heterocycle, and a partially or fully saturated carbocyclic ring, where the moiety is optionally substituted, or $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —CH$_2$CH$_2$— or —C($R^{4c}$)($R^{4c'}$)—, where $R^{4c}$ is hydrogen, cyano, hydroxy, amino, H$_2$NC(O)—, or a chemical moiety selected from the group consisting of ($C_1$–$C_6$)alkyl, ($C_1$–$C_6$)alkoxy, acyloxy, acyl, ($C_1$–$C_3$)alkyl-O—C(O)—, ($C_1$–$C_4$)alkyl-NH—C(O)—, ($C_1$–$C_4$)alkyl)$_2$N—C(O)—, ($C_1$–$C_6$)alkylamino-, (($C_1$–$C_4$)alkyl)$_2$amino-, ($C_3$–$C_6$)cycloalkylamino-, acylamino-, aryl($C_1$–$C_4$)alkylamino-, heteroaryl($C_1$–$C_4$)alkylamino-, aryl, heteroaryl, a partially or fully saturated 3–6 membered heterocycle, and a partially or fully saturated carbocyclic ring, where the moiety is optionally substituted, or $R^{4c}$ taken together with $R^{4e}$, $R^{4e'}$, $R^{4f}$, or $R^{f'}$ forms a bond, a methylene bridge, or an ethylene bridge, and $R^{4c'}$ is hydrogen, $H_2NC(O)$—, or a chemical moiety selected from the group consisting of ($C_1$–$C_6$)alkyl, acyl, ($C_1$–$C_3$)alkyl-O—C(O)—, ($C_1$–$C_4$)alkyl-NH—C(O)—, ($C_1$–$C_4$)alkyl)$_2$N—C(O)—, aryl, heteroaryl, a partially or fully saturated 3–6 membered heterocycle, and a partially or fully saturated carbocyclic ring, where the moiety is optionally substituted, or $R^{4c'}$ taken together with $R^{4e}$, $R^{4e'}$, $R^{f}$, or $R^{f'}$ forms a bond, a methylene bridge, or an ethylene bridge (preferably, X is a bond, —$CH_2CH_2$— or —C($R^{4c}$)($R^{4c'}$)—, where $R^{4c}$ and $R^{4c'}$ are each independently hydrogen or ($C_1$–$C_6$)alkyl);

Y is oxygen, sulfur, —C(O)—, or —C($R^{4d}$)($R^{4d'}$)—, where $R^{4d}$ is hydrogen, cyano, hydroxy, amino, $H_2NC(O)$—, or a chemical moiety selected from the group consisting of ($C_1$–$C_6$)alkyl, ($C_1$–$C_6$)alkoxy, acyloxy, acyl, ($C_1$–$C_3$)alkyl-O—C(O)—, ($C_1$–$C_4$)alkyl-NH—C(O)—, ($C_1$–$C_4$)alkyl)$_2$N—C(O)—, ($C_1$–$C_6$)alkylamino-, (($C_1$–$C_4$)alkyl)$_2$amino-, ($C_3$–$C_6$)cycloalkylamino-, acylamino-, aryl($C_1$–$C_4$)alkylamino-, heteroaryl($C_1$–$C_4$)alkylamino-, aryl, heteroaryl, a partially or fully saturated 3–6 membered heterocycle, and a partially or fully saturated carbocyclic ring, where the moiety is optionally substituted, and $R^{4d'}$ is hydrogen, $H_2NC(O)$—, or a chemical moiety selected from the group consisting of ($C_1$–$C_6$)alkyl, acyl, ($C_1$–$C_3$)alkyl-O—C(O)—, ($C_1$–$C_4$)alkyl-NH—C(O)—, ($C_1$–$C_4$)alkyl)$_2$N—C(O)—, aryl, heteroaryl, a partially or fully saturated 3–6 membered heterocycle, and a partially or fully saturated carbocyclic ring, where the moiety is optionally substituted, or $R^{4d}$ and $R^{4d'}$ taken together form a partially or fully saturated, 3–6 membered heterocyclic ring, a 5–6 membered lactone ring, or a 4–6 membered lactam ring, where the heterocyclic ring, the lactone ring and the lactam ring are optionally substituted and the lactone ring and the lactam ring optionally contain an additional heteroatom selected from oxygen, nitrogen or sulfur, or Y is —$NR^{4d''}$, where $R^{4d''}$ is a hydrogen or a chemical moiety selected from the group consisting of ($C_1$–$C_6$)alkyl, ($C_3$–$C_6$)cycloalkyl, ($C_1$–$C_3$)alkylsulfonyl-, ($C_1$–$C_3$)alkylaminosulfonyl-, di($C_1$–$C_3$)alkylaminosulfonyl-, acyl, ($C_1$–$C_6$)alkyl-O—C(O)—, aryl, and heteroaryl, where the moiety is optionally substituted (preferably, Y is —$NR^{4d''}$—, where $R^{4d''}$ is a hydrogen or a chemical moiety selected from the group consisting of ($C_1$–$C_6$)alkyl, ($C_3$–$C_6$)cycloalkyl, ($C_1$–$C_3$)alkylsulfonyl-, ($C_1$–$C_3$)alkylaminosulfonyl-, di($C_1$–$C_3$)alkylaminosulfonyl-, acyl, ($C_1$–$C_6$)alkyl-O—C(O)—, aryl, and heteroaryl, where the moiety is optionally substituted);

Z is a bond, —$CH_2CH_2$—, or —C($R^{4e}$)($R^{4e'}$)—, where $R^{4e}$ is hydrogen, cyano, hydroxy, amino, $H_2NC(O)$—, or a chemical moiety selected from the group consisting of ($C_1$–$C_6$)alkyl, ($C_1$–$C_6$)alkoxy, acyloxy, acyl, ($C_1$–$C_3$)alkyl-O—C(O)—, ($C_1$–$C_4$)alkyl-NH—C(O)—, ($C_1$–$C_4$)alkyl)$_2$N—C(O)—, ($C_1$–$C_6$)alkylamino-, (($C_1$–$C_4$)alkyl)$_2$amino-, ($C_3$–$C_6$)cycloalkylamino-, acylamino-, aryl($C_1$–$C_4$)alkylamino-, heteroaryl($C_1$–$C_4$)alkylamino-, aryl, heteroaryl, a partially or fully saturated 3–6 membered heterocycle, and a partially or fully saturated carbocyclic ring, where the moiety is optionally substituted, or $R^{4e}$ taken together with $R^{4b}$, $R^{4b'}$, $R^{4c}$, or $R^{4c'}$ forms a bond, a methylene bridge, or an ethylene bridge, and $R^{4e'}$ is hydrogen, $H_2NC(O)$—, or a chemical moiety selected from the group consisting of ($C_1$–$C_6$)alkyl, acyl, ($C_1$–$C_3$)alkyl-O—C(O)—, ($C_1$–$C_4$)alkyl-NH—C(O)—, ($C_1$–$C_4$)alkyl)$_2$N—C(O)—, aryl, heteroaryl, a partially or fully saturated 3–6 membered heterocycle, and a partially or fully saturated carbocyclic ring, where the moiety is optionally substituted, or $R^{4e'}$ taken together with $R^{4b}$, $R^{4b'}$, $R^{4c}$, or $R^{4c'}$ forms a bond, a methylene bridge, or an ethylene bridge (preferably, Z is a bond, —$CH_2CH_2$— or —C($R^{4c}$)($R^{4c'}$)—, where $R^{4c}$ and $R^{4c'}$ are each independently hydrogen or ($C_1$–$C_6$)alkyl);

$R^{4f}$ is hydrogen, cyano, hydroxy, amino, $H_2NC(O)$—, or a chemical moiety selected from the group consisting of ($C_1$–$C_6$)alkyl, ($C_1$–$C_6$)alkoxy, acyloxy, acyl, ($C_1$–$C_3$)alkyl-O—C(O)—, ($C_1$–$C_4$)alkyl-NH—C(O)—, ($C_1$–$C_4$)alkyl)$_2$N—C(O)—, ($C_1$–$C_6$)alkylamino-, (($C_1$–$C_4$)alkyl)$_2$amino-, ($C_3$–$C_6$)cycloalkylamino-, acylamino-, aryl($C_1$–$C_4$)alkylamino-, heteroaryl($C_1$–$C_4$)alkylamino-, aryl, heteroaryl, a partially or fully saturated 3–6 membered heterocycle, and a partially or fully saturated carbocyclic ring, where the moiety is optionally substituted; and $R^{4f'}$ is hydrogen, $H_2NC(O)$—, or a chemical moiety selected from the group consisting of ($C_1$–$C_6$)alkyl, acyl, ($C_1$–$C_3$)alkyl-O—C(O)—, ($C_1$–$C_4$)alkyl-NH—C(O)—, ($C_1$–$C_4$)alkyl)$_2$N—C(O)—, aryl, heteroaryl, a partially or fully saturated 3–6 membered heterocycle, and a partially or fully saturated carbocyclic ring, where the moiety is optionally substituted, or $R^{f}$ or $R^{4f'}$ taken together with $R^{4b}$, $R^{4b'}$, $R^{4c}$, or $R^{4c'}$ forms a bond, a methylene bridge, or an ethylene bridge;

a pharmaceutically acceptable salt thereof, a prodrug of the compound or the salt, or a solvate or hydrate of the compound, the salt or the prodrug.

Preferred embodiments of compounds of Formula (I) and (II) where $R^4$ is a group of Formula (IB) are the same as those described above for the group of Formula (IA). Preferred compounds include: 7-(1-benzylpyrrolidin-3-yloxy)-3-(4-chlorophenyl)-2-(2-chlorophenyl)-5-methylpyrazolo[1,5-a]pyrimidine; 3-(4-chlorophenyl)-2-(2-chlorophenyl)-7-(1-cyclohexylazetidin-3-yloxy)-5-methylpyrazolo[1,5-a]pyrimidine; and 7-(1-tert-butylazetidin-3-yloxy)-3-(4-chlorophenyl)-2-(2-chlorophenyl)-5-methylpyrazolo[1,5-a]pyrimidine; a pharmaceutically acceptable salt thereof or a solvate or hydrate of said compound or said salt.

Yet another preferred compound of the present invention is a compound of Formula (II) where $R^4$ is a group of Formula (IC), where $R^5$ and $R^6$ are each independently hydrogen or ($C_1$–$C_4$)alkyl, and $R^7$ is ($C_1$–$C_4$)alkyl-, halo-substituted ($C_1$–$C_4$)alkyl-, ($C_1$–$C_4$)alkoxy($C_1$–$C_4$)alkyl-, ($C_1$–$C_4$)alkylamino($C_1$–$C_4$)alkyl-, di($C_1$–$C_4$)alkylamino ($C_1$–$C_4$)alkyl-, or a partially or fully saturated 4–6 membered heterocyclic ring containing 1 to 2 heteroatoms independently selected from oxygen, sulfur or nitrogen, or $R^5$ and $R^6$ or $R^5$ and $R^7$ taken together form a 5–6 membered lactone, 4–6 membered lactam, or a 4–6 membered partially or fully saturated heterocycle containing 1 to 2 heteroatoms independently selected from oxygen, sulfur or nitrogen, where the lactone, the lactam and the heterocycle are optionally substituted; a pharmaceutically acceptable salt thereof, a prodrug of the compound or the salt, or a solvate or hydrate of the compound, the salt or the prodrug. Preferably, $R^5$ and $R^6$ are each independently hydrogen or ($C_1$–$C_4$)alkyl, and $R^7$ is ($C_1$–$C_4$)alkyl. Preferred compounds include: 3-(4-chlorophenyl)-2-(2-chlorophenyl)-7-isopropoxy-5-methylpyrazolo[1,5-a]pyrimidine; 3-(4-chlorophenyl)-2-(2-chlorophenyl)-7-ethoxypyrazolo[1,5-a]pyrimidine; 3-(4-chlorophenyl)-2-(2-chlorophenyl)-7-(2,2,2-trifluoroethoxy)-pyrazolo[1,5-a]pyrimidine; and 7-allyloxy-3-(4-chlorophenyl)-2-(2-chlorophenyl)-pyrazolo[1,5-a]

pyrimidine; a pharmaceutically acceptable salt thereof or a solvate or hydrate of said compound or said salt.

A preferred compound of Formula (I) where $R^4$ is —O—$R^5$ is 3-(4-chlorophenyl)-2-(2-chlorophenyl)-7-iodomethyl-6,7-dihydro-8-oxa-1,4,8b-triaza-as-indacene.

Another preferred compound of the present invention is a compound of Formula (II) where $R^4$ is an amino group having attached thereto at least one chemical moiety selected from the group consisting of ($C_1$–$C_8$)alkyl, aryl ($C_1$–$C_4$)alkyl, a 3–8 membered partially or fully saturated carbocyclic ring, hydroxy($C_1$–$C_6$)alkyl, ($C_1$–$C_3$)alkoxy ($C_1$–$C_6$)alkyl, heteroaryl($C_1$–$C_3$)alkyl, and a partially or fully saturated heterocycle, where said chemical moiety is optionally substituted with one or more substituents; a pharmaceutically acceptable salt thereof, or a solvate or hydrate of said compound or said salt.

Preferred compounds include: butyl-[3-(4-chlorophenyl)-2-(2-chlorophenyl)-5-methylpyrazolo[1,5-a]pyrimidin-7-yl]-amine; [3-(4-chlorophenyl)-2-(2-chlorophenyl)-5-methylpyrazolo[1,5-a]pyrimidin-7-yl]-(2-morpholin-4-yl-ethyl)-amine; [3-(4-chlorophenyl)-2-(2-chlorophenyl)-5-methylpyrazolo[1,5-a]pyrimidin-7-yl]-(2-methoxyethyl)-amine; and [3-(4-chlorophenyl)-2-(2-chlorophenyl)-5-methylpyrazolo[1,5-a]pyrimidin-7-yl]-[2-(4-fluorophenyl)-ethyl]-amine; a pharmaceutically acceptable salt thereof or a solvate or hydrate of said compound or said salt.

Yet another preferred compound of the present invention is a compound of Formula (II) where $R^4$ is an ($C_1$–$C_6$)alkyl group having attached thereto at least one chemical moiety selected from the group consisting of hydroxy, ($C_1$–$C_6$) alkoxy, amino, ($C_1$–$C_6$)alkylamino, di(($C_1$–$C_6$)alkyl)amino ($C_1$–$C_3$)alkylsulfonyl, ($C_1$–$C_3$)alkylsulfamyl, di(($C_1$–$C_3$) alkyl)sulfamyl, acyloxy, a partially or fully saturated heterocycle, and a partially or fully saturated carbocyclic ring, where said chemical moiety is optionally substituted with one or more substituents; a pharmaceutically acceptable salt thereof, or a solvate or hydrate of said compound or said salt.

Finally, another preferred compound of the present invention is a compound of Formula (II) where $R^4$ is an optionally substituted aryl or optionally substituted heteroaryl; a pharmaceutically acceptable salt thereof, or a solvate or hydrate of said compound or said salt. A preferred compound of this embodiment is 3,7-bis-(4-chlorophenyl)-2-(2-chlorophenyl)-pyrazolo[1,5-a]pyrimidine.

Another aspect of the present invention includes the following compounds of Formula (Id), (Ie), (If), (4d) and (4e) which are useful intermediates in the synthesis of compounds of Formulae (I) and (II) above.

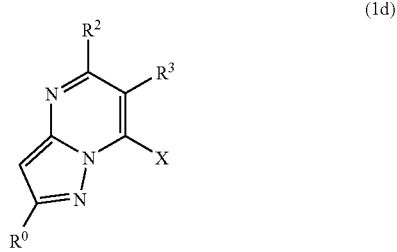

(1d)

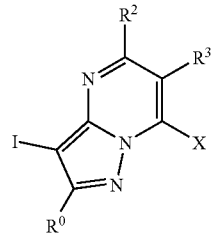

(1e)

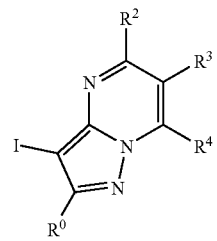

(1f)

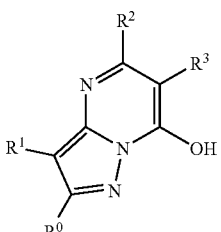

(4d)

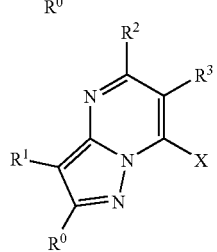

wherein X is chlorine or bromine (preferably, chloro), and $R^0$, $R^2$, $R^3$, and $R^4$ are as defined above (including preferred embodiments); provided that for the compound of Formula (1d), $R^0$ is not phenyl, 3-chlorophenyl, or 3,4,5-trimethoxyphenyl; and for the compounds of Formulae (4d) and (4e), $R^0$ is not 4-methylsulfonylphenyl, 4-aminosulfonylphenyl, or a 4-alkyl-substituted phenyl when $R^1$ is a 4-halo-substituted phenyl; and $R^0$ and $R^1$ are not both an unsubstituted phenyl.

Some of the compounds described herein contain at least one chiral center; consequently, those skilled in the art will appreciate that all stereoisomers (e.g., enantiomers and diastereoisomers) of the compounds illustrated and discussed herein are within the scope of the present invention. In addition, tautomeric forms of the compounds are also within the scope of the present invention. Those skilled in the art will recognize that chemical moieties such as an alpha-amino ether or an alpha-chloro amine may be too unstable to isolate; therefore, such moieties do not form a part of this invention.

Compounds of the present invention have been shown to be useful cannabinoid receptor ligands (in particular, CB1 receptor antagonists). Accordingly, another aspect of the present invention is a pharmaceutical composition that comprises (1) a compound of the present invention, and (2) a pharmaceutically acceptable excipient, diluent, or carrier. Preferably, the composition comprises a therapeutically effective amount of a compound of the present invention. The composition may also contain at least one additional pharmaceutical agent (described herein). Preferred agents include nicotine receptor partial agonists, opioid antagonists (e.g., naltrexone and nalmefene), dopaminergic agents (e.g., apomorphine), attention deficit disorder (ADD including attention deficit hyperactivity disorder (ADHD)) agents (e.g., Ritalin™, Strattera™, Concerta™ and Adderall™), and anti-obesity agents (described herein below).

In yet another embodiment of the present invention, a method for treating a disease, condition or disorder modulated by a cannabinoid receptor (preferably, a CB1 receptor) antagonists in animals that includes the step of administering to an animal in need of such treatment a therapeutically effective amount of a compound of the present invention (or a pharmaceutical composition thereof).

Diseases, conditions, and/or disorders modulated by cannabinoid receptor antagonists include eating disorders (e.g., binge eating disorder, anorexia, and bulimia), weight loss or control (e.g., reduction in calorie or food intake, and/or appetite suppression), obesity, depression, atypical depression, bipolar disorders, psychoses, schizophrenia, behavioral addictions, suppression of reward-related behaviors (e.g., conditioned place avoidance, such as suppression of cocaine- and morphine-induced conditioned place preference), substance abuse, addictive disorders, impulsivity, alcoholism (e.g., alcohol abuse, addiction and/or dependence including treatment for abstinence, craving reduction and relapse prevention of alcohol intake), tobacco abuse (e.g., smoking addiction, cessation and/or dependence including treatment for craving reduction and relapse prevention of tobacco smoking), dementia (including memory loss, Alzheimer's disease, dementia of aging, vascular dementia, mild cognitive impairment, age-related cognitive decline, and mild neurocognitive disorder), sexual dysfunction in males (e.g., erectile difficulty), seizure disorders, epilepsy, inflammation, gastrointestinal disorders (e.g., dysfunction of gastrointestinal motility or intestinal propulsion), attention deficit disorder (ADD/ADHD), Parkinson's disease, and type II diabetes. In a preferred embodiment, the method is used in the treatment of weight loss, obesity, bulimia, ADD/ADHD, Parkinson's disease, dementia, alcoholism, and/or tobacco abuse.

Compounds of the present invention may be administered in combination with other pharmaceutical agents. Preferred pharmaceutical agents include nicotine receptor partial agonists, opioid antagonists (e.g., naltrexone (including naltrexone depot), antabuse, and nalmefene), dopaminergic agents (e.g., apomorphine), ADD/ADHD agents (e.g., methylphenidate hydrochloride (e.g., Ritalin™ and Concerta™), atomoxetine (e.g., Strattera™), and amphetamines (e.g., Adderall™)) and anti-obesity agents, such as apo-B/MTP inhibitors, 11β-hydroxy steroid dehydrogenase-1 (11β-HSD type 1) inhibitors, peptide $YY_{3-36}$ or analogs thereof, MCR-4 agonists, CCK-A agonists, monoamine reuptake inhibitors, sympathomimetic agents, $β_3$ adrenergic receptor agonists, dopamine receptor agonists, melanocyte-stimulating hormone receptor analogs, 5-HT2c receptor agonists, melanin concentrating hormone receptor antagonists, leptin, leptin analogs, leptin receptor agonists, galanin receptor antagonists, lipase inhibitors, bombesin receptor agonists, neuropeptide-Y receptor antagonists (e.g., NPY Y5 antagonists such as those described hereinbelow), thyromimetic agents, dehydroepiandrosterone or analogs thereof, glucocorticoid receptor antagonists, orexin receptor antagonists, glucagon-like peptide-1 receptor agonists, ciliary neurotrophic factors, human agouti-related protein antagonists, ghrelin receptor antagonists, histamine 3 receptor antagonists or inverse agonists, and neuromedin U receptor agonists, and the like.

The combination therapy may be administered as (a) a single pharmaceutical composition which comprises a compound of the present invention, at least one additional pharmaceutical agent described herein and a pharmaceutically acceptable excipient, diluent, or carrier; or (b) two separate pharmaceutical compositions comprising (i) a first composition comprising a compound of the present invention and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions may be administered simultaneously or sequentially and in any order.

In yet another aspect of the present invention, a pharmaceutical kit is provided for use by a consumer to treat diseases, conditions or disorders modulated by cannabinoid receptor antagonists in an animal. The kit comprises a) a suitable dosage form comprising a compound of the present invention; and b) instructions describing a method of using the dosage form to treat diseases, conditions or disorders that are modulated by cannabinoid receptor (in particular, the CB1 receptor) antagonists.

In yet another embodiment of the present invention is a pharmaceutical kit comprising: a) a first dosage form comprising (i) a compound of the present invention and (ii) a pharmaceutically acceptable carrier, excipient or diluent; b) a second dosage form comprising (i) an additional pharmaceutical agent described herein, and (ii) a pharmaceutically acceptable carrier, excipient or diluent; and c) a container.

Definitions

As used herein, the term "alkyl" refers to a hydrocarbon radical of the general formula $C_nH_{2n+1}$. The alkane radical may be straight or branched. For example, the term "$(C_1–C_6)$alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion (i.e., alkyl moiety) of an alkoxy, acyl (e.g., alkanoyl), alkylamino, dialkylamino, and alkylthio group have the same definition as above. When indicated as being "optionally substituted", the alkane radical or alkyl moiety may be unsubstituted or substituted with one or more substituents (generally, one to three substituents except in the case of halogen substituents such as perchloro or perfluoroalkyls) independently selected from the group of substituents listed below in the definition for "substituted." "Halo-substituted alkyl" refers to an alkyl group substituted with one or more halogen atoms (e.g., fluoromethyl, difluoromethyl, trifluoromethyl, perfluoroethyl, and the like). When substituted, the alkane radicals or alkyl moieties are preferably substituted with 1 to 3 fluoro substituents, or 1 or 2 substituents independently selected from $(C_1–C_3)$alkyl, $(C_3–C_6)$cycloalkyl, $(C_2–C_3)$alkenyl, aryl, heteroaryl, 3- to 6-membered heterocycle, chloro, cyano, hydroxy, $(C_1–C_3)$ alkoxy, aryloxy, amino, $(C_1–C_6)$alkyl amino, di-$(C_1–C_4)$ alkyl amino, aminocarboxylate (i.e., $(C_1–C_3)$alkyl-O—C (O)—NH—), hydroxy$(C_2–C_3)$alkylamino, or keto (oxo), and more preferably, 1 to 3 fluoro groups, or 1 substituent selected from $(C_1–C_3)$alkyl, $(C_3–C_6)$cycloalkyl, $(C_6)$aryl, 6-membered-heteroaryl, 3- to 6-membered heterocycle, $(C_1-C_3)$alkoxy, $(C_1-C_4)$alkyl amino or di-$(C_1-C_2)$alkyl amino.

The terms "partially or fully saturated carbocyclic ring" (also referred to as "partially or fully saturated cycloalkyl") refers to nonaromatic rings that are either partially or fully hydrogenated and may exist as a single ring, bicyclic ring or a spiral ring. Unless specified otherwise, the carbocyclic ring is generally a 3- to 8-membered ring. For example, partially or fully saturated carbocyclic rings (or cycloalkyl) include groups such as cyclopropyl, cyclopropenyl, cyclobutyl, cyclobutenyl, cyclopentyl, cyclpentenyl, cyclopentadienyl, cyclohexyl, cyclohexenyl, cyclohexadienyl, norbornyl (bicyclo[2.2.1]heptyl), norbornenyl, bicyclo[2.2.2]octyl, and the like. When designated as being "optionally substituted", the partially saturated or fully saturated cycloalkyl group may be unsubstituted or substituted with one or more substituents (typically, one to three substituents) independently selected from the group of substituents listed below in the definition for "substituted." A substituted carbocyclic ring also includes groups wherein the carbocyclic ring is fused to a phenyl ring (e.g., indanyl). The carbocyclic group may be attached to the chemical entity or moiety by any one of the carbon atoms within the carbocyclic ring system. When substituted, the carbocyclic group is preferably substituted with 1 or 2 substituents independently selected from $(C_1-C_3)$alkyl, $(C_2-C_3)$alkenyl, $(C_1-C_6)$alkylidenyl, aryl, heteroaryl, 3- to 6-membered heterocycle, chloro, fluoro, cyano, hydroxy, $(C_1-C_3)$alkoxy, aryloxy, amino, $(C_1-C_6)$alkyl amino, di-$(C_1-C_4)$alkyl amino, aminocarboxylate (i.e., $(C_1-C_3)$alkyl-O—C(O)—NH—), hydroxy$(C_2-C_3)$alkylamino, or keto (oxo), and more preferably 1 or 2 from substituents independently selected from $(C_1-C_2)$alkyl, 3- to 6-membered heterocycle, fluoro, $(C_1-C_3)$alkoxy, $(C_1-C_4)$ alkyl amino or di-$(C_1-C_2)$alkyl amino. Similarly, any cycloalkyl portion of a group (e.g., cycloalkylalkyl, cycloalkylamino, etc.) has the same definition as above.

The term "partially saturated or fully saturated heterocyclic ring" (also referred to as "partially saturated or fully saturated heterocycle") refers to nonaromatic rings that are either partially or fully hydrogenated and may exist as a single ring, bicyclic ring or a spiral ring. Unless specified otherwise, the heterocyclic ring is generally a 3- to 6-membered ring containing 1 to 3 heteroatoms (preferably 1 or 2 heteroatoms) independently selected from sulfur, oxygen and/or nitrogen. Partially saturated or fully saturated heterocyclic rings include groups such as epoxy, aziridinyl, tetrahydrofuranyl, dihydrofuranyl, dihydropyridinyl, pyrrolidinyl, N-methylpyrrolidinyl, imidazolidinyl, imidazolinyl, piperidinyl, piperazinyl, pyrazolidinyl, 2H-pyranyl, 4H-pyranyl, 2H-chromenyl, oxazinyl, morpholino, thiomorpholino, tetrahydrothienyl, tetrahydrothienyl 1,1-dioxide, and the like. When indicated as being "optionally substituted", the partially saturated or fully saturated heterocycle group may be unsubstiuted or substituted with one or more substituents (typically, one to three substituents) independently selected from the group of substituents listed below in the definition for "substituted." A substituted heterocyclic ring includes groups wherein the heterocyclic ring is fused to an aryl or heteroaryl ring (e.g., 2,3-dihydrobenzofuranyl, 2,3-dihydroindolyl, 2,3-dihydrobenzothiophenyl, 2,3-dihydrobenzothiazolyl, etc.). When substituted, the heterocycle group is preferably substituted with 1 or 2 substituents independently selected from $(C_1-C_3)$alkyl, $(C_3-C_6)$cycloalkyl, $(C_2-C_4)$alkenyl, aryl, heteroaryl, 3- to 6-membered heterocycle, chloro, fluoro, cyano, hydroxy, $(C_1-C_3)$alkoxy, aryloxy, amino, $(C_1-C_6)$alkyl amino, di-$(C_1-C_3)$alkyl amino, aminocarboxylate (i.e., $(C_1-C_3)$alkyl-O—C(O)—NH—), or keto (oxo), and more preferably with 1 or 2 substituents independently selected from $(C_1-C_3)$alkyl, $(C_3-C_6)$cycloalkyl, $(C_6)$aryl, 6-membered-heteroaryl, 3- to 6-membered heterocycle, or fluoro. The heterocyclic group may be attached to the chemical entity or moiety by any one of the ring atoms within the heterocyclic ring system. Similarly, any heterocycle portion of a group (e.g., heterocycle-substituted alkyl, heterocycle carbonyl, etc.) has the same definition as above.

The term "aryl" or "aromatic carbocyclic ring" refers to aromatic moieties having a single (e.g., phenyl) or a fused ring system (e.g., naphthalene, anthracene, phenanthrene, etc.). A typical aryl group is a 6- to 10-membered aromatic carbocyclic ring(s). When indicated as being "optionally substituted", the aryl groups may be unsubstituted or substituted with one or more substituents (preferably no more than three substituents) independently selected from the group of substituents listed below in the definition for "substituted." Substituted aryl groups include a chain of aromatic moieties (e.g., biphenyl, terphenyl, phenylnaphthalyl, etc.). When substituted, the aromatic moieties are preferably substituted with 1 or 2 substituents independently selected from $(C_1-C_4)$alkyl, $(C_2-C_3)$alkenyl, aryl, heteroaryl, 3- to 6-membered heterocycle, bromo, chloro, fluoro, iodo, cyano, hydroxy, $(C_1-C_4)$alkoxy, aryloxy, amino, $(C_1-C_6)$alkyl amino, di-$(C_1-C_3)$alkyl amino, or aminocarboxylate (i.e., $(C_1-C_3)$alkyl-O—C(O)—NH—), and more preferably, 1 or 2 substituents independently selected from $(C_1-C_4)$alkyl, chloro, fluoro, cyano, hydroxy, or $(C_1-C_4)$alkoxy. The aryl group may be attached to the chemical entity or moiety by any one of the carbon atoms within the aromatic ring system. Similarly, the aryl portion (i.e., aromatic moiety) of an aroyl or aroyloxy (i.e., (aryl)-C(O)—) has the same definition as above.

The term "heteroaryl" or "heteroaromatic ring" refers to aromatic moieties containing at least one heteroatom (e.g., oxygen, sulfur, nitrogen or combinations thereof) within a 5- to 10-membered aromatic ring system (e.g., pyrrolyl, pyridyl, pyrazolyl, indolyl, indazolyl, thienyl, furanyl, benzofuranyl, oxazolyl, imidazolyl, tetrazolyl, triazinyl, pyrimidyl, pyrazinyl, thiazolyl, purinyl, benzimidazolyl, quinolinyl, isoquinolinyl, benzothiophenyl, benzoxazolyl, etc.). The heteroaromatic moiety may consist of a single or fused ring system. A typical single heteroaryl ring is a 5- to 6-membered ring containing one to three heteroatoms independently selected from oxygen, sulfur and nitrogen and a typical fused heteroaryl ring system is a 9- to 10-membered ring system containing one to four heteroatoms independently selected from oxygen, sulfur and nitrogen. When indicated as being "optionally substituted", the heteroaryl groups may be unsubstituted or substituted with one or more substituents (preferably no more than three substituents) independently selected from the group of substituents listed below in the definition for "substituted." When substituted, the heteroaromatic moieties are preferably substituted with 1 or 2 substituents independently selected from $(C_1-C_4)$ alkyl, $(C_2-C_3)$alkenyl, aryl, heteroaryl, 3- to 6-membered heterocycle, bromo, chloro, fluoro, iodo, cyano, hydroxy, $(C_1-C_4)$alkoxy, aryloxy, amino, $(C_1-C_6)$alkyl amino, di-$(C_1-C_3)$alkyl amino, or aminocarboxylate (i.e., $(C_1-C_3)$ alkyl-O—C(O)—NH—), and more preferably, 1 or 2 substituents independently selected from $(C_1-C_4)$alkyl, chloro, fluoro, cyano, hydroxy, $(C_1-C_4)$alkoxy, $(C_1-C_4)$alkyl amino or di-$(C_1-C_2)$alkyl amino. The heteroaryl group may be attached to the chemical entity or moiety by any one of the atoms within the aromatic ring system (e.g., imidazol-1-yl, imidazol-2-yl, imidazol-4-yl, imidazol-5-yl, pyrid-2-yl, pyrid-3-yl, pyrid-4-yl, pyrid-5-yl, or pyrid-6-yl). Similarly, the heteroaryl portion (i.e., heteroaromatic moiety) of a heteroaroyl or heteroaroyloxy (i.e., (heteroaryl)-C(O)—) has the same definition as above.

The term "acyl" refers to alkyl, partially saturated or fully saturated cycloalkyl, partially saturated or fully saturated heterocycle, aryl, and heteroaryl substituted carbonyl groups. For example, acyl includes groups such as ($C_1$–$C_6$) alkanoyl (e.g., formyl, acetyl, propionyl, butyryl, valeryl, caproyl, t-butylacetyl, etc.), ($C_3$–$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions above. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "substituted" specifically envisions and allows for one or more substitutions that are common in the art. However, it is generally understood by those skilled in the art that the substituents should be selected so as to not adversely affect the pharmacological characteristics of the compound or adversely interfere with the use of the medicament. Suitable substituents for any of the groups defined above include ($C_1$–$C_6$)alkyl, ($C_3$–$C_7$)cycloalkyl, ($C_2$–$C_6$) alkenyl, ($C_1$–$C_6$)alkylidenyl, aryl, heteroaryl, 3- to 6-membered heterocycle, halo (e.g., chloro, bromo, iodo and fluoro), cyano, hydroxy, ($C_1$–$C_6$)alkoxy, aryloxy, sulfhydryl (mercapto), ($C_1$–$C_6$)alkylthio, arylthio, amino, mono- or di-($C_1$–$C_6$)alkyl amino, quaternary ammonium salts, amino ($C_1$–$C_6$)alkoxy, aminocarboxylate (i.e., ($C_1$–$C_6$)alkyl-O—C (O)—NH—), hydroxy($C_2$–$C_6$)alkylamino, amino($C_1$–$C_6$) alkylthio, cyanoamino, nitro, ($C_1$–$C_6$)carbamyl, keto (oxo), acyl, ($C_1$–$C_6$)alkyl-$CO_2$—, glycolyl, glycyl, hydrazino, guanyl, sulfamyl, sulfonyl, sulfinyl, thio($C_1$–$C_6$)alkyl-C(O)—, thio($C_1$–$C_6$)alkyl-$CO_2$—, and combinations thereof. In the case of substituted combinations, such as "substituted aryl ($C_1$–$C_6$)alkyl", either the aryl or the alkyl group may be substituted, or both the aryl and the alkyl groups may be substituted with one or more substituents (typically, one to three substituents except in the case of perhalo substitutions). An aryl or heteroaryl substituted carbocyclic or heterocyclic group may be a fused ring (e.g., indanyl, dihydrobenzofuranyl, dihydroindolyl, etc.).

The term "solvate" refers to a molecular complex of a compound represented by Formula (I) or (II) (including prodrugs and pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The term "protecting group" or "Pg" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, *Protective Groups in Organic Synthesis*, John Wiley & Sons, New York, 1991.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The terms "modulated by a cannabinoid receptor" or "modulation of a cannabinoid receptor" refers to the activation or deactivation of a cannabinoid receptor. For example, a ligand may act as an agonist, partial agonist, inverse agonist, antagonist, or partial antagonist.

The term "antagonist" includes both full antagonists and partial antagonists, as well as inverse agonists.

The term "CB-1 receptor" refers to the G-protein coupled type 1 cannabinoid receptor.

The term "compounds of the present invention" (unless specifically identified otherwise) refer to compounds of Formula (I) and Formula (II), prodrugs thereof, pharmaceutically acceptable salts of the compounds, and/or prodrugs, and hydrates or solvates of the compounds, salts, and/or prodrugs, as well as, all stereoisomers (including diastereoisomers and enantiomers), tautomers and isotopically labeled compounds.

DETAILED DESCRIPTION

The present invention provides compounds and pharmaceutical formulations thereof that are useful in the treatment of diseases, conditions and/or disorders modulated by cannabinoid receptor antagonists.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1–19, Wiley, N.Y. (1967–1999 ed.), or *Beilsteins Handbuch der organischen Chemie*, 4, Aufl. ed. Springer-Verlag, Berlin, including supplements (also available via the *Beilstein* online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, *Protective Groups in Organic Synthesis*, John Wiley & Sons, New York, 1991.

Compounds of present invention may be prepared using procedures analogous to those described in Senga, K., et al, "Synthesis and Antischistosomal Activity of Certain Pyrazolo[1,5,a]pyrimidines," *J. Med. Chem.* 24, 610–615 (1981) and U.S. Pat. Nos. 6,060,478 and 5,688,949, each of which are incorporated herein by reference. Scheme I outlines the procedures one could use to provide compounds of the present invention via 7-chloropyrazolo[1,5,a]pyrimidine intermediate (1d).

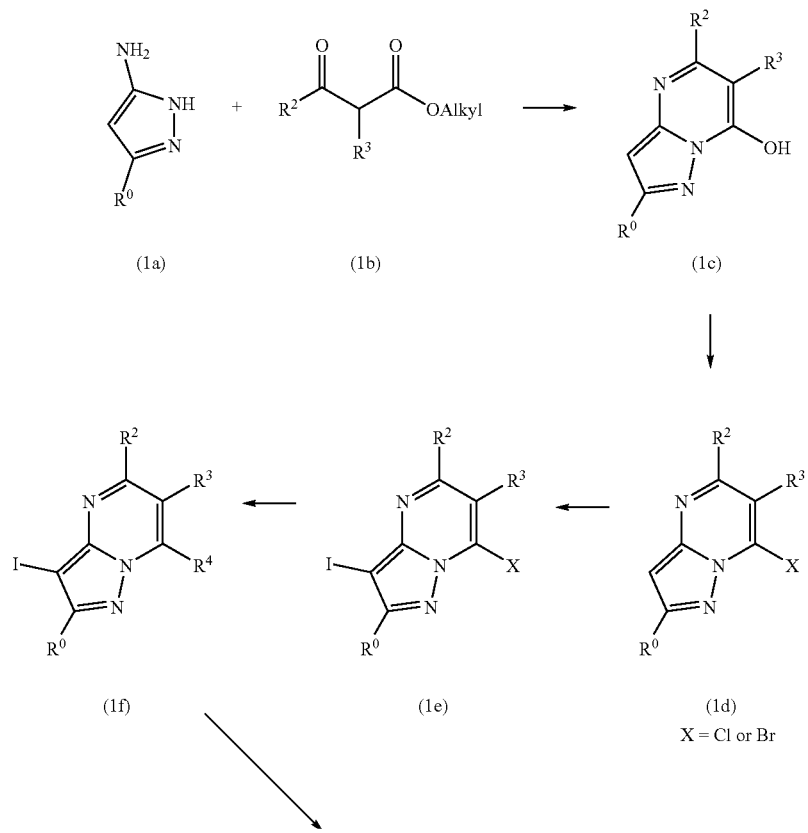

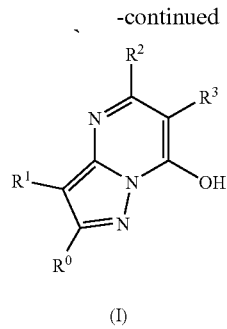

(I)

The 3-aminopyrazole (1a) may be purchased or prepared using procedures analogous to those described in Pakamigawa, A., *Yakugaku Zasski*, 84, 1113 (1964).

The pyrazolo[1,5,a]pyrimidin-7-ol (1c) may be formed from the condensation of 3-aminopyrazole (1a) with the desired alkyl acylacetate (1b) in an appropriate solvent (e.g., ethanol, benzene) in the presence or absence of an acid (e.g., acetic acid, p-toluenesulfonic acid) at a temperature of about 30° C. to reflux. Preferred alkyl acylacetates include ethyl acetoacetate, methyl acetoacetate, ethyl acetopropionate, methyl formylpropionate, and the sodium salt of ethyl formylacetate.

Conversion of the pyrazolo[1,5,a]pyrimidin-7-ol (1c) to the 7-halopyrazolopyrimidine ((1d), X=Cl, Br) may be accomplished by treatment with a halogenating agent (e.g., $SOCl_2$, $POCl_3$, $PCl_3$, $PCl_5$, $POBr_3$, $PBr_3$, $PBr_5$, or $PPh_3$/NBS) in the presence of absence of base (e.g., triethylamine, diisopropylethylamine, pyridine, N,N-diethylaniline) in the presence or absence of a reaction inert solvent (e.g., toluene, xylenes, dioxane) at temperatures ranging from about −40° C. to 200° C. (For analogous transformations, see: WO 02/072202 and O. Sugimoto et al., *Tetrahedron Left.*, 40, 7477–7478 (1999)). In a preferred example, pyrazolopyrimidin-7-ol (1c) is treated with phosphorus oxychloride in the presence of a trialkylamine base (e.g., triethylamine, diisopropylethylamine) in refluxing toluene to give the corresponding 7-chloropyrazolopyrimidine (1d). Alternatively, pyrazolopyrimidin-7-ol (1c) may be activated ((1d), X=leaving group) by treatment with reagents like methanesulfonic anhydride, methanesulfonyl chloride, trifluoromethanesulfonic anhydride, or p-toluenesulfonyl chloride in a reaction inert solvent (e.g., methylene chloride) in the presence of a suitable base (e.g., triethylamine, diisopropylethylamine, pyridine, collidine).

A bromine or iodine may be installed at the 3-position of pyrazolopyrimidine (1d) using procedures analogous to those described in Example 14 of WO 01/23388. For instance, position 3 may be iodinated to give iodopyrazolopyrimidine (1e) by treating the pyrazolopyrimidine (1d) with a reagent such as N-iodosuccinimide (NIS), iodine, or iodonium bis-symcollidine perchlorate (preferably NIS) in an aprotic solvent (e.g., carbon tetrachloride, methylene chloride, or chloroform). Suitable reaction temperatures range from about −78° C. to 60° C., and the reaction is preferably conducted at around 0–25° C.

Substituent $R^4$, where $R^4$ is an amino group of Formula (IA) or an amino group substituted with one or more substituents described above, may be introduced via a coupling reaction between intermediate (1e) and the corresponding amino compound ($R^4$—H) to produce intermediate (1f). For example, intermediate (1e) is generally stirred with the desired amine ($R^4$—H). The amine may act as the solvent (e.g., butylamine, morpholine, pyrrolidine) or a solvent (e.g., methylene chloride, N,N-dimethylformamide, THF, water, ethanol, methanol, dichloroethane, acetone) may be added to assist in solubilization of the reactants and/or provide a media having the appropriate refluxing temperature to complete the substitution. The reaction may be heated to accelerate the process. Suitable reaction temperatures range from about −40° C. to 100° C., and are preferably conducted at around 30° C. In addition, a suitable base (e.g., triethylamine, diisopropylethylamine) may be employed to quench the acid produced in the process. Suitable amino compounds can be either purchased commercially or easily prepared using standard procedures well-known to those skilled in the art. Preferred amino compounds ($R^4$—H) include 4-alkylaminopiperidine-4-carboxamides (Scheme III) and 3-alkylaminoazetidine-3-carboxamides that are described below.

Compounds of the present invention where $R^4$ is an alkoxy group (i.e., $R^4$=a group of Formula (1B) or (1C)), may be prepared by treating intermediate (1e) with the desired alcohol in the presence of a base (e.g., potassium t-butoxide, NaH, 1,4-diazabicyclo[2.2.2]octane, diisopropylethylamine). The alcohol may act as solvent, or an aprotic solvent may be added to assist in solubilization of the reactants and/or provide a media having the appropriate refluxing temperature to complete the substitution (e.g., THF, methylene chloride, DMF). Suitable alcohols can be either purchased commercially or easily prepared using standard procedures well known to those skilled in the art.

Compounds of formula (I) may be prepared using procedures analogous to those described for Scheme 9 of U.S. Pat. No. 6,372,743, incorporated herein by reference. For example, the second aryl or heteroaryl group ($R^2$) could be introduced via metal-mediated cross-coupling reactions such as the Suzuki reaction (See: A. Suzuki in *Metal-Catalyzed Cross-Coupling Reactions*; F. Diederich and P. J. Stang, Eds.; Wiley-VCH Verlag, Weinheim, Germany, Chapter 2 (1998) and N. Miyaura and A. Suzuki *Chem. Rev.*, 95, 2457–2483 (1995)) and the Stille reaction (T. N. Mitchell in *Metal-Catalyzed Cross-Coupling Reactions*; F. Diederich and P. J. Stang, Eds.; Wiley-VCH Verlag, Weinheim, Germany, Chapter 4 (1998)). In a preferred method, the compound of the Formula (I) may be produced by Suzuki reaction of intermediate (1f) with a compound of Formula $R^2$—$B(OH)_2$ in the presence of a complex or salt of palladium (e.g., $Pd(PPh_3)_4$, $Pd(OAc)_2$, $PdCl_2dppf$), a base (e.g., cesium carbonate, sodium carbonate, cesium fluoride, potassium phosphate), and a suitable solvent (e.g., toluene, water, dioxane, N,N-dimethylformamide, dimethoxyethane, THF) in the presence or absence of added ligand (e.g., dppf, dppb).

Preferred reaction temperatures range from about 0° C. to about 120° C. For a detailed description of a representative compound prepared using the procedures generally described in Scheme I above, see Examples 1A-1, 2A-1 and 11A-1 in the Examples section below.

Alternatively, intermediate (1d) may be prepared using the general procedures outlined in Scheme II below which may then be further modified to produce a compound of the present invention as described above in Scheme I.

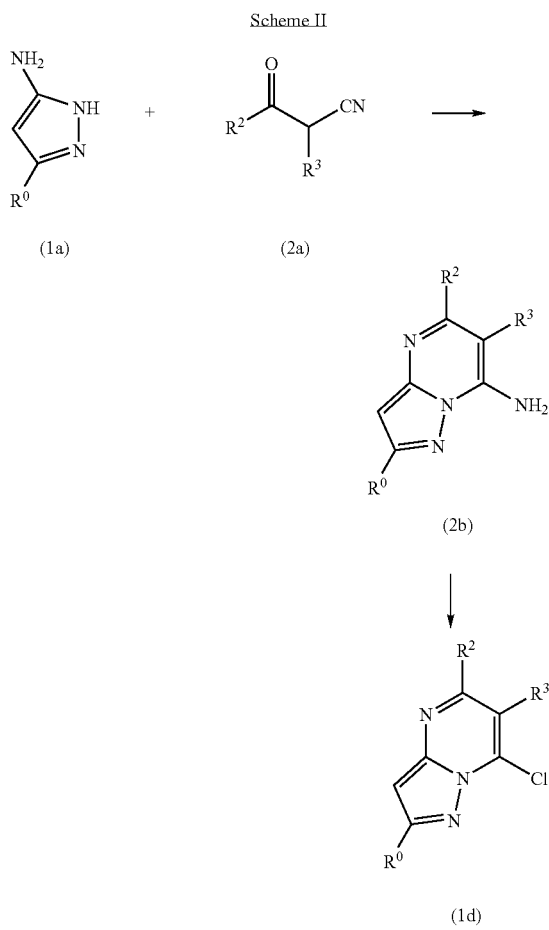

3-aminopyrazole (1a) may be condensed with α-cyanoketone (2a) in an inert solvent (e.g., ethanol) to produce aminopyrazoles of formula (2b). The condensation may be facilitated by the addition of base (see: U.S. Pat. No. 6,060,478) or acid (see: C. Bellec et al. in Can. J. Chem., 59, 2826–2832 (1981)). Aminopyrazole (2b) may then be converted to chloropyrazole (1d) upon treatment with a halogenating agent like phosphorous oxychloride (see: A. Takamizawa et al. in Chem. Pharm. Bull., 13, 1207–1220 (1965)).

Numerous amine compounds of Formula (IA) are available from commercial sources or prepared by known methods readily available to those skilled in the art. Representative preparations of amine compounds of Formula (IA) are illustrated in the Examples below. The preparation of 4-aminopiperidine-4-carboxamide groups of Formula (IA) and 4-amino-4-cyano piperidine groups of Formula (IA) and their benzyl protected precursors are described by P. A. J. Janssen in U.S. Pat. No. 3,161,644, C. van de Westeringh et al. in J. Med. Chem., 7, 619–623 (1964), and K. A. Metwally et al. in J. Med. Chem., 41, 5084–5093 (1998) where the above 4-amino groups are unsubstituted, monosubstituted, disubstituted, or part of a heterocyclic ring. Related bicyclic derivatives are described by K. Frohlich et al. in Tetrahedron, 54, 13115–13128 (1998) and references contained therein. Spiro-substituted piperidines of formula (IA) are described by P. A. J. Janssen in U.S. Pat. No. 3,155,670, K. A. Metwally et al. in J. Med Chem., 41, 5084–5093 (1998), T. Toda et al. in Bull. Chem. Soc. Japan, 44, 3445–3450 (1971), and W. Brandau and S. Samnick in WO 9522544. The preparation of 3-aminoazetidine-3-carboxamide is described by A. P. Kozikowski and A. H. Fauq in Synlett, 783–784 (1991). The preparation of preferred 4-alkylaminopiperidine-4-carboxamide groups of Formula (IA) are depicted in Scheme III below. The corresponding 3-alkylaminoazetidine-3-carboxamides and 3-alkylaminopyrolidine-3-carboxamides may be prepared in an analogous fashion. Spiro-substituted derivates are available by procedures analogous to those contained in the above references. A detailed description of a representative spiro-substituted amine may be found in the "Preparation of Key Intermediates" section of the Examples below (see, e.g., I-5A-10d).

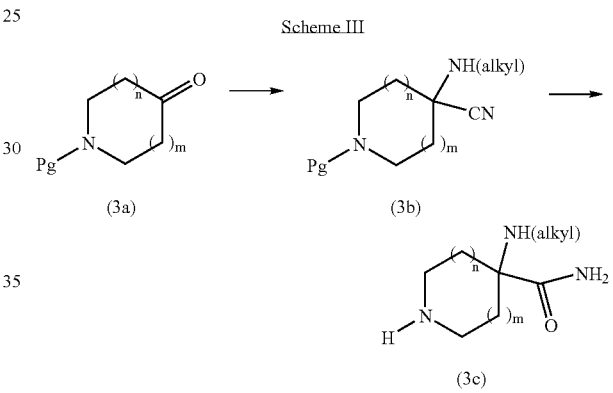

n, m = 0 or 1

The amino group of 4-piperidinone is first protected to provide intermediate (3a). A useful protection group is benzyl. 4-Piperidinone and derivatives thereof may be purchased commercially from a variety of sources (e.g., Interchem Corporation, Paramus, N.J. and Sigma-Aldrich Co., St. Louis, Mo.). Piperidinone (3a) may then be reacted with the desired alkylamine and potassium cyanide in an aqueous HCl/ethanol solvent mixture at about 0° C. to about 30° C. The cyano group is converted to the corresponding amide with acid and water, or with alkaline hydrogen peroxide in the presence of DMSO (see Y. Sawaki and Y. Ogata in Bull. Chem. Soc. Jpn. 54, 793–799 (1981)). The protecting group is then removed using conventional methods for the particular protecting group employed. For example, a benzyl-protecting group may be removed by hydrogenation in the presence of Pd/C. A detailed description of some representative amines having Formula (3c) above may be found in the "Preparation of Key Intermediates" section of the Examples below (see, e.g., I-1A-1g, I-1A-3e, and I-3A-1c).

In another approach, both of the aryl or heteroaryl groups ($R^0$ and $R^1$) are introduced earlier in the synthetic scheme such as by the route outlined below in Scheme IV. For example, $R^0$ and $R^1$ may be introduced into the compound of Formula (I) via the 3-aminopyrazole intermediate (4c).

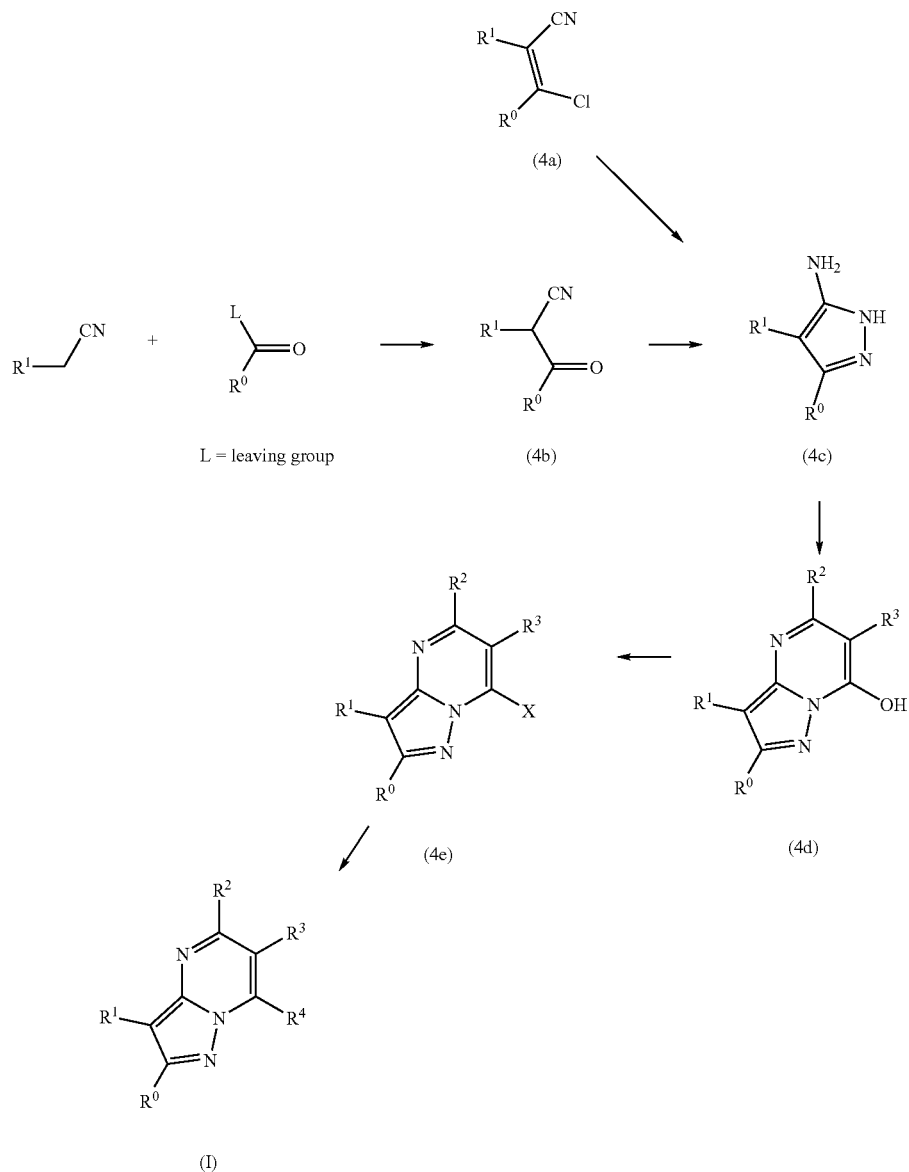

Scheme IV

The cyano intermediate (4a) may be converted to the 3-aminopyrazole (4c) using procedures analogous to those disclosed in C. Almansa, et al., *J. Med. Chem.*, 44, 350–361 (2001). For example, intermediate (4a) may be treated with hydrazine in ethanol at about 78° C. for about 18 hours. Alternatively, the 3-aminopyrazole (4c) may be prepared from the condensation of hydrazine with α-cyanoketone (4b). The latter (4b) is readily prepared by methods familiar to those skilled in the arts, such as by condensing the desired nitrile ($R^1$—$CH_2CN$) with the desired acid chloride, acid bromide, or ester ($R^0$—C(O)-L, where L is a leaving group). A detailed description of 3-aminopyrazole (3c) above may be found in the "Preparation of Key Intermediates" section of the Examples below (see, I-3A-1b). The disubstituted 3-aminopyrazole (4c) may then be converted to compounds of Formula (I) using transformations analogous to those described in Scheme I. For a detailed description of a representative compounds prepared using the procedures generally described in Scheme IV above, see Examples 3A-1, 4A-1, 5A-1, 6A-1, 8A-1, 9A-1, and 10A-1 in the Examples section below.

Compounds of Formula (I) above where $R^4$ is a primary or secondary amine can be alkylated, sulfonated and/or acylated to provide additional derivatives (e.g., alkylamines, dialkylamines, sulfonamides, amides, carbamates, ureas, etc.) using standard procedures well-known to those skilled in the art. In some cases, the Compounds of Formula (I) above where $R^4$ is a protected primary or secondary amine needs to be deprotected by methods well-known to those skilled in the art to unmask the primary or secondary amine prior to further functionalization. For a more detailed description of representative compounds prepared using these procedures, see Examples 6A-1 and 7A-1 in the Examples section below.

An alternative route to compounds where $R^4$ is an ether group involves O-alkylation of pyrazolopyrimidin-7-ol (1c) or (4d). For a detailed description of a representative compound prepared using this procedure, see Example 12A-1 in the Examples section below.

For those compounds of Formula (I) where $R^4$ is an unsubstituted or substituted alkenyl, aryl, or heteroaryl group, intermediate (2b) may be functionalized using metal-mediated cross-coupling reactions as described above. For a detailed description of a representative compound prepared where $R^4$ is an aryl group, see Example 14A-1 in the Examples section below.

An alternate method for introducing an $R^3$ substituent is shown in Scheme V below.

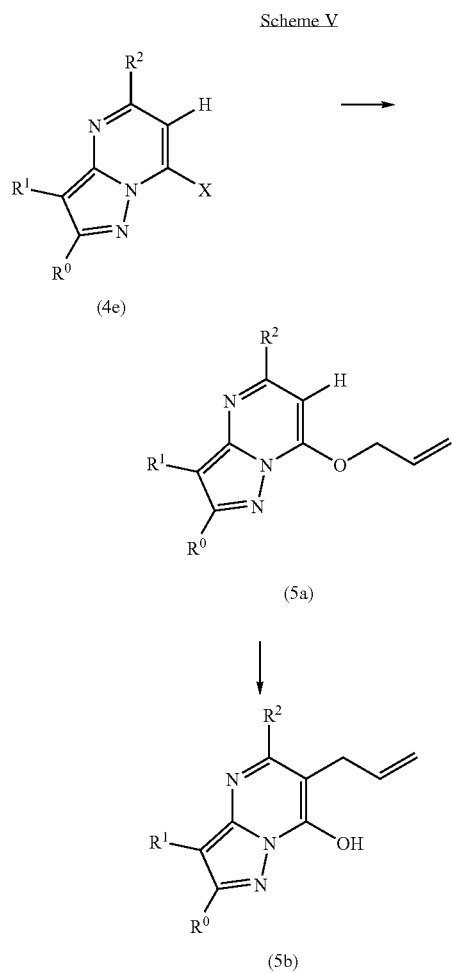

Scheme V (4e)

(5a)

(5b)

Compound (4e) may be coupled with an allyl alcohol as described above to give intermediate (5a). The allyl alcohol may be optionally substituted with one or more alkyl groups. Compound 5a can then be heated to facilitate a Claisen rearrangement to provide (5b), which can be further transformed as with (4b) to provide compounds of Formula (I). The olefin provides a handle for further manipulations well known to those skilled in the art. For instance, compound (5b) could be cyclized to provide a tricyclic compound upon treatment with N-iodosuccinimide. For a more detailed description of a representative compound prepared using the procedures generally described in Scheme V, see Example 15A-1 in the Examples section below.

Conventional methods and/or techniques of separation and purification known to one of ordinary skill in the art can be used to isolate the compounds of the present invention, as well as the various intermediates related thereto. Such techniques will be well-known to one of ordinary skill in the art and may include, for example, all types of chromatography (high pressure liquid chromatography (HPLC), column chromatography using common adsorbents such as silica gel, and thin-layer chromatography), recrystallization, and differential (i.e., liquid-liquid) extraction techniques.

The compounds of the present invention may be isolated and used per se or in the form of its pharmaceutically acceptable salt, solvate and/or hydrate. The term "salts" refers to inorganic and organic salts of a compound of the present invention. These salts can be prepared in situ during the final isolation and purification of a compound, or by separately reacting the compound, N-oxide, or prodrug with a suitable organic or inorganic acid or base and isolating the salt thus formed. Representative salts include the hydrobromide, hydrochloride, hydroiodide, sulfate, bisulfate, nitrate, acetate, trifluoroacetate, oxalate, besylate, palmitiate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate, and laurylsulfonate salts, and the like. A preferred salt of the compounds of the present invention is the hydrochloride salt. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, e.g., Berge, et al., *J. Pharm. Sci.*, 66, 1–19 (1977).

The term "prodrug" means a compound that is transformed in vivo to yield a compound of Formula (I) or a pharmaceutically acceptable salt, hydrate or solvate of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the present invention contains a carboxylic acid functional group, a prodrug can comprise an ester formed by the replacement of the hydrogen atom of the acid group with a group such as $(C_1-C_8)$ alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino $(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

Similarly, if a compound of the present invention contains an alcohol functional group, a prodrug can be formed by the replacement of the hydrogen atom of the alcohol group with a group such as $(C_1-C_6)$alkanoyloxymethyl, 1-$((C_1-C_6)$ alkanoyloxy)ethyl, 1-methyl-1-$((C_1-C_6)$alkanoyloxy)ethyl, ($C_1$–$C_6$)alkoxycarbonyloxymethyl, N-($C_1$–$C_6$)alkoxycarbonylaminomethyl, succinoyl, ($C_1$–$C_6$)alkanoyl, α-amino ($C_1$–$C_4$)alkanoyl, arylacyl and α-aminoacyl, or α-aminoacyl-α-aminoacyl, where each α-aminoacyl group is independently selected from the naturally occurring L-amino acids, P(O)(OH)$_2$, P(O)(O($C_1$–$C_6$)alkyl)$_2$ or glycosyl (the radical resulting from the removal of a hydroxyl group of the hemiacetal form of a carbohydrate).

If a compound of the present invention incorporates an amine functional group, a prodrug can be formed by the replacement of a hydrogen atom in the amine group with a group such as R-carbonyl, RO-carbonyl, NRR'-carbonyl where R and R' are each independently ($C_1$–$C_{10}$)alkyl, ($C_3$–$C_7$)cycloalkyl, benzyl, or R-carbonyl is a natural α-aminoacyl or natural α-aminoacyl-natural α-aminoacyl, —C(OH)C(O)OY' wherein Y' is H, ($C_1$–$C_6$)alkyl or benzyl, —C(OY$_0$)Y$_1$ wherein Y$_0$ is ($C_1$–$C_4$)alkyl and Y$_1$ is ($C_1$–$C_6$) alkyl, carboxy($C_1$–$C_6$)alkyl, amino($C_1$–$C_4$)alkyl or mono-N- or di-N,N-($C_1$–$C_6$)alkylaminoalkyl, —C(Y$_2$)Y$_3$ wherein Y$_2$ is H or methyl and Y$_3$ is mono-N- or di-N,N-($C_1$–$C_6$) alkylamino, morpholino, piperidin-1-yl or pyrrolidin-1-yl.

The compounds of the present invention may contain asymmetric or chiral centers, and, therefore, exist in different stereoisomeric forms. It is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention. Both the single positional isomers and mixture of positional isomers resulting from the N-oxidation of the pyrimidine and pyrazine rings are also within the scope of the present invention.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

The compounds of the present invention may exist in unsolvated as well as solvated forms with pharmaceutically acceptable solvents such as water, ethanol, and the like, and it is intended that the invention embrace both solvated and unsolvated forms.

It is also possible that the compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine, iodine, and chlorine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{123}$I, $^{125}$I and $^{36}$Cl, respectively.

Certain isotopically-labeled compounds of the present invention (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Compounds of the present invention are useful for treating diseases, conditions and/or disorders modulated by cannabinoid receptor antagonists; therefore, another embodiment of the present invention is a pharmaceutical composition comprising a therapeutically effective amount of a compound of the present invention and a pharmaceutically acceptable excipient, diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides a method of treating diseases, conditions and/or disorders modulated by cannabinoid receptor antagonists in an animal that includes administering to an animal in need of such treatment a therapeutically effective amount of a compound of the present invention or a pharmaceutical composition comprising an effective amount of a compound of the present invention and a pharmaceutically acceptable excipient, diluent, or carrier. The method is particularly useful for treating diseases, conditions and/or disorders modulated by cannabinoid receptor (in particular, CB1 receptor) antagonists.

Preliminary investigations have indicated that the following diseases, conditions, and/or disorders are modulated by cannabinoid receptor antagonists: eating disorders (e.g., binge eating disorder, anorexia, and bulimia), weight loss or control (e.g., reduction in calorie or food intake, and/or appetite suppression), obesity, depression, atypical depression, bipolar disorders, psychoses, schizophrenia, behavioral addictions, suppression of reward-related behaviors (e.g., conditioned place avoidance, such as suppression of cocaine- and morphine-induced conditioned place preference), substance abuse, addictive disorders, impulsivity, alcoholism (e.g., alcohol abuse, addiction and/or dependence including treatment for abstinence, craving reduction and relapse prevention of alcohol intake), tobacco abuse (e.g., smoking addiction, cessation and/or dependence including treatment for craving reduction and relapse prevention of tobacco smoking), dementia (including memory loss, Alzheimer's disease, dementia of aging, vascular dementia, mild cognitive impairment, age-related cognitive decline, and mild neurocognitive disorder), sexual dysfunction in males (e.g., erectile difficulty), seizure disorders, epilepsy, inflammation, gastrointestinal disorders (e.g., dysfunction of gastrointestinal motility or intestinal propulsion), attention deficit disorder (ADD including attention deficit hyperactivity disorder (ADHD)), Parkinson's disease, and type II diabetes.

Accordingly, the compounds of the present invention described herein are useful in treating diseases, conditions, or disorders that are modulated by cannabinoid receptor antagonists. Consequently, the compounds of the present invention (including the compositions and processes used therein) may be used in the manufacture of a medicament for the therapeutic applications described herein.

Other diseases, conditions and/or disorders for which cannabinoid receptor antagonists may be effective include: premenstrual syndrome or late luteal phase syndrome, migraines, panic disorder, anxiety, post-traumatic syndrome, social phobia, cognitive impairment in non-demented individuals, non-amnestic mild cognitive impairment, post operative cognitive decline, disorders associated with impulsive behaviours (such as, disruptive behaviour disorders (e.g., anxiety/depression, executive function improvement, tic disorders, conduct disorder and/or oppositional defiant disorder), adult personality disorders (e.g., borderline personality disorder and antisocial personality disorder), diseases associated with impulsive behaviours (e.g., substance abuse, paraphilias and self-mutilation), and impulse control disorders (e.g., intermittene explosive disorder, kleptomania, pyromania, pathological gambling, and trichotillomania)), obsessive compulsive disorder, chronic fatigue syndrome, sexual dysfunction in males (e.g., premature ejaculation), sexual dysfunction in females, disorders of sleep (e.g., sleep apnea), autism, mutism, neurodengenerative movement disorders, spinal cord injury, damage of the central nervous system (e.g., trauma), stroke, neurodegenerative diseases or toxic or infective CNS diseases (e.g., encephalitis or meningitis), cardiovascular disorders (e.g., thrombosis), and diabetes.

The compounds of the present invention can be administered to a patient at dosage levels in the range of from about 0.7 mg to about 7,000 mg per day. For a normal adult human having a body weight of about 70 kg, a dosage in the range of from about 0.01 mg to about 100 mg per kilogram body weight is typically sufficient. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include anti-obesity agents such as apolipoprotein-B secretion/microsomal triglyceride transfer protein (apo-B/MTP) inhibitors, 11β-hydroxy steroid dehydrogenase-1 (11β-HSD type 1) inhibitors, peptide $YY_{3-36}$ or analogs thereof, MCR-4 agonists, cholecystokinin-A (CCK-A) agonists, monoamine reuptake inhibitors (such as sibutramine), sympathomimetic agents, $β_3$ adrenergic receptor agonists, dopamine agonists (such as bromocriptine), melanocyte-stimulating hormone receptor analogs, 5HT2c agonists, melanin concentrating hormone antagonists, leptin (the OB protein), leptin analogs, leptin receptor agonists, galanin antagonists, lipase inhibitors (such as tetrahydrolipstatin, i.e. orlistat), anorectic agents (such as a bombesin agonist), Neuropeptide-Y antagonists (e.g., NPY Y5 receptor antagonists, such as the spiro compounds described in U.S. Pat. Nos. 6,566,367; 6,649,624; 6,638,942; 6,605,720; 6,495,559; 6,462,053; 6,388,077; 6,335,345; and 6,326,375; US Publication Nos. 2002/0151456 and 2003/036652; and PCT Publication Nos. WO 03/010175, WO 03/082190 and WO 02/048152), thyromimetic agents, dehydroepiandrosterone or an analog thereof, glucocorticoid receptor agonists or antagonists, orexin receptor antagonists, glucagon-like peptide-1 receptor agonists, ciliary neurotrophic factors (such as Axokine™ available from Regeneron Pharmaceuticals, Inc., Tarrytown, N.Y. and Procter & Gamble Company, Cincinnati, Ohio), human agouti-related proteins (AGRP), ghrelin receptor antagonists, histamine 3 receptor antagonists or inverse agonists, neuromedin U receptor agonists and the like. Other anti-obesity agents, including the preferred agents set forth hereinbelow, are well known, or will be readily apparent in light of the instant disclosure, to one of ordinary skill in the art.

Especially preferred are anti-obesity agents selected from the group consisting of orlistat, sibutramine, bromocriptine, ephedrine, leptin, pseudoephedrine, peptide $YY_{3-36}$ or an analog thereof, and 2-oxo-N-(5-phenylpyrazinyl)spiro-[isobenzofuran-1(3H),4'-piperidine]-1'-carboxamide. Preferably, compounds of the present invention and combination therapies are administered in conjunction with exercise and a sensible diet.

Representative anti-obesity agents for use in the combinations, pharmaceutical compositions, and methods of the invention can be prepared using methods known to one of ordinary skill in the art, for example, sibutramine can be prepared as described in U.S. Pat. No. 4,929,629; bromocriptine can be prepared as described in U.S. Pat. Nos. 3,752,814 and 3,752,888; orlistat can be prepared as described in U.S. Pat. Nos. 5,274,143; 5,420,305; 5,540,917; and 5,643,874; $PYY_{3-36}$ (including analogs) can be prepared as described in US Publication No. 2002/0141985 and WO 03/027637; and the NPY Y5 receptor antagonist 2-oxo-N-(5-phenylpyrazinyl)spiro[isobenzofuran-1(3H),4'-piperidine]-1'-carboxamide can be prepared as described in US Publication No. 2002/0151456. Other useful NPY Y5 receptor antagonists include those described in PCT Publication No. 03/082190, such as 3-oxo-N-(5-phenyl-2-pyrazinyl)-spiro[isobenzofuran-1(3H),4'-piperidine]-1'-carboxamide; 3-oxo-N-(7-trifluoromethylpyrido[3,2-b]pyridin-2-yl)-spiro-[isobenzofuran-1(3H),4'-piperidine]-1'-carboxamide; N-[5-(3-fluorophenyl)-2-pyrimidinyl]-3-oxospiro-[isobenzofuran-1(3H), [4'-piperidine]-1'-carboxamide; trans-3'-oxo-N-(5-phenyl-2-pyrimidinyl)]spiro[cyclohexane-1,1' (3'H)-isobenzofuran]-4-carboxamide; trans-3'-oxo-N-[1-(3-quinolyl)-4-imidazolyl]spiro[cyclohexane-1,1'(3'H)-isobenzofuran]-4-carboxamide; trans-3-oxo-N-(5-phenyl-2-pyrazinyl)spiro[4-azaiso-benzofuran-1(3H),1'-cyclohexane]-4'-carboxamide; trans-N-[5-(3-fluorophenyl)-2-pyrimidinyl]-3-oxospiro[5-azaisobenzofuran-1(3H), 1'-cyclohexane]-4'-carboxamide; trans-N-[5-(2-fluorophenyl)-2-pyrimidinyl]-3-oxospiro[5-azaisobenzofuran-1(3H), 1'-cyclohexane]-4'-carboxamide; trans-N-[1-(3,5-difluorophenyl)-4-imidazolyl]-3-oxospiro[7-azaisobenzofuran-1 (3H),1'-cyclohexane]-4'-carboxamide; trans-3-oxo-N-(1-phenyl-4-pyrazolyl)spiro[4-azaisobenzofuran-1(3H),1'-cyclohexane]-4'-carboxamide; trans-N-[1-(2-fluorophenyl)-3-pyrazolyl]-3-oxospiro[6-azaisobenzofuran-1(3H),1'-cyclohexane]-4'-carboxamide; trans-3-oxo-N-(1-phenyl-3-pyrazolyl)spiro[6-azaisobenzofuran-1(3H),1'-cyclohexane]-4'-carboxamide; trans-3-oxo-N-(2-phenyl-1,2,3-triazol-4-yl)spiro[6-azaisobenzofuran-1(3H),1'-cyclohexane]-4'-carboxamide; and pharmaceutically acceptable salts and esters thereof. All of the above recited U.S. patents and publications are incorporated herein by reference.

Other suitable pharmaceutical agents that may be administered in combination with the compounds of the present invention include agents designed to treat tobacco abuse (e.g., nicotine receptor partial agonists, bupropion hypochloride (also known under the tradename Zyban™) and nicotine replacement therapies), agents to treat erectile dysfunction (e.g., dopaminergic agents, such as apomorphine), ADD/ADHD agents (e.g., Ritalin™, Strattera™, Concerta™ and Adderall™), and agents to treat alcoholism, such as opioid antagonists (e.g., naltrexone (also known under the tradename ReVia™) and nalmefene), disulfiram (also known under the tradename Antabuse™), and acamprosate (also known under the tradename Campral™)). In addition, agents for reducing alcohol withdrawal symptoms may also be co-administered, such as benzodiazepines, beta-blockers, clonidine, carbamazepine, pregabalin, and gabapentin (Neurontin™). Treatment for alcoholism is preferably administered in combination with behavioral therapy including such components as motivational enhancement therapy, cognitive behavioral therapy, and referral to self-help groups, including Alcohol Anonymous (AA).

Other pharmaceutical agents that may also be useful include antihypertensive agents; anti-inflammatory agents (e.g., COX-2 inhibitors); antidepressants (e.g., fluoxetine hydrochloride (Prozac™)); cognitive improvement agents (e.g., donepezil hydrochloride (Aircept™) and other acetylcholinesterase inhibitors); neuroprotective agents (e.g., memantine); antipsychotic medications (e.g., ziprasidone (Geodon™), risperidone (Risperdal™), and olanzapine (Zyprexa™)); insulin and insulin analogs (e.g., LysPro insulin); GLP-1 (7–37) (insulinotropin) and GLP-1 (7–36)-$NH_2$; sulfonylureas and analogs thereof: chlorpropamide, glibenclamide, tolbutamide, tolazamide, acetohexamide, Glypizide®, glimepiride, repaglinide, meglitinide; biguanides: metformin, phenformin, buformin; $\alpha$2-antagonists and imidazolines: midaglizole, isaglidole, deriglidole, idazoxan, efaroxan, fluparoxan; other insulin secretagogues: linogliride, A-4166; glitazones: ciglitazone, Actos® (pioglitazone), englitazone, troglitazone, darglitazone, Avandia® (BRL49653); fatty acid oxidation inhibitors: clomoxir, etomoxir; $\alpha$-glucosidase inhibitors: acarbose, miglitol, emiglitate, voglibose, MDL-25,637, camiglibose, MDL-73,945; $\beta$-agonists: BRL 35135, BRL 37344, RO 16–8714, ICI D7114, CL 316,243; phosphodiesterase inhibitors: L-386, 398; lipid-lowering agents: benfluorex: fenfluramine; vanadate and vanadium complexes (e.g., Naglivan®) and peroxovanadium complexes; amylin antagonists; glucagon antagonists; gluconeogenesis inhibitors; somatostatin analogs; antilipolytic agents: nicotinic acid, acipimox, WAG 994, pramlintide (Symlin™), AC 2993, nateglinide, aldose reductase inhibitors (e.g., zopolrestat), glycogen phosphorylase inhibitors, sorbitol dehydrogenase inhibitors, sodium-hydrogen exchanger type 1 (NHE-1) inhibitors and/or cholesterol biosynthesis inhibitors or cholesterol absorption inhibitors, especially a HMG-CoA reductase inhibitor (e.g., atorvastatin or the hemicalcium salt thereof), or a HMG-CoA synthase inhibitor, or a HMG-CoA reductase or synthase gene expression inhibitor, a CETP inhibitor, a bile acid sequesterant, a fibrate, an ACAT inhibitor, a squalene synthetase inhibitor, an anti-oxidant or niacin. The compounds of the present invention may also be administered in combination with a naturally occurring compound that acts to lower plasma cholesterol levels. Such naturally occurring compounds are commonly called nutraceuticals and include, for example, garlic extract, Hoodia plant extracts, and niacin.

The dosage of the additional pharmaceutical agent is generally dependent upon a number of factors including the health of the subject being treated, the extent of treatment desired, the nature and kind of concurrent therapy, if any, and the frequency of treatment and the nature of the effect desired. In general, the dosage range of the additional pharmaceutical agent is in the range of from about 0.001 mg to about 100 mg per kilogram body weight of the individual per day, preferably from about 0.1 mg to about 10 mg per kilogram body weight of the individual per day. However, some variability in the general dosage range may also be required depending upon the age and weight of the subject being treated, the intended route of administration, the particular anti-obesity agent being administered and the like. The determination of dosage ranges and optimal dosages for a particular patient is also well within the ability of one of ordinary skill in the art having the benefit of the instant disclosure.

According to the methods of the invention, a compound of the present invention or a combination of a compound of the present invention and at least one additional pharmaceutical agent is administered to a subject in need of such treatment, preferably in the form of a pharmaceutical composition. In the combination aspect of the invention, the compound of the present invention and at least one other pharmaceutical agent (e.g., anti-obesity agent, nicotine receptor partial agonist, ADHD agent, dopaminergic agent, or opioid antagonist) may be administered either separately or in the pharmaceutical composition comprising both. It is generally preferred that such administration be oral. However, if the subject being treated is unable to swallow, or oral administration is otherwise impaired or undesirable, parenteral or transdermal administration may be appropriate.

According to the methods of the invention, when a combination of a compound of the present invention and at least one other pharmaceutical agent are administered together, such administration can be sequential in time or simultaneous with the simultaneous method being generally preferred. For sequential administration, a compound of the present invention and the additional pharmaceutical agent can be administered in any order. It is generally preferred that such administration be oral. It is especially preferred that such administration be oral and simultaneous. When a compound of the present invention and the additional pharmaceutical agent are administered sequentially, the administration of each can be by the same or by different methods.

According to the methods of the invention, a compound of the present invention or a combination of a compound of the present invention and at least one additional pharmaceutical agent (referred to herein as a "combination") is preferably administered in the form of a pharmaceutical composition. Accordingly, a compound of the present invention or a combination can be administered to a patient separately or together in any conventional oral, rectal, transdermal, parenteral, (for example, intravenous, intramuscular, or subcutaneous) intracisternal, intravaginal, intraperitoneal, intravesical, local (for example, powder, ointment or drop), or buccal, or nasal, dosage form.

Compositions suitable for parenteral injection generally include pharmaceutically acceptable sterile aqueous or nonaqueous solutions, dispersions, suspensions, or emulsions, and sterile powders for reconstitution into sterile injectable solutions or dispersions. Suitable aqueous and nonaqueous carriers or diluents (including solvents and vehicles) include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain excipients such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, powders, and granules. In such solid dosage forms, a compound of the present invention or a combination is admixed with at least one inert excipient, diluent or carrier. Suitable excipients, diluents or carriers include materials such as sodium citrate or dicalcium phosphate or (a) fillers or extenders (e.g., starches, lactose, sucrose, mannitol, silicic acid and the like); (b) binders (e.g., carboxymethylcellulose, alginates, gelatin, polyvinylpyrrolidone, sucrose, acacia and the like); (c) humectants (e.g., glycerol and the like); (d) disintegrating agents (e.g., agar-agar, calcium carbonate, potato or tapioca starch, alginic acid, certain complex silicates, sodium carbonate and the like); (e) solution retarders (e.g., paraffin and the like); (f) absorption accelerators (e.g., quaternary ammonium compounds and the like); (g) wetting agents (e.g., cetyl alcohol, glycerol monostearate and the like); (h) adsorbents (e.g., kaolin, bentonite and the like); and/or (i) lubricants (e.g., talc, calcium stearate, magnesium stearate, solid polyethylene glycols, sodium lauryl sulfate and the like). In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well known in the art. They may also contain opacifying agents, and can also be of such composition that they release the compound of the present invention and/or the additional pharmaceutical agent in a delayed manner. Examples of embedding compositions that can be used are polymeric substances and waxes. The drug can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the compound of the present invention or the combination, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed oil, groundnut oil, corn germ oil, olive oil, castor oil, sesame seed oil and the like), glycerol, tetrahydrofurfuryl alcohol, polyethylene glycols and fatty acid esters of sorbitan, or mixtures of these substances, and the like.

Besides such inert diluents, the composition can also include excipients, such as wetting agents, emulsifying and suspending agents, sweetening, flavoring, and perfuming agents.

Suspensions, in addition to the compound of the present invention or the combination, may further comprise carriers such as suspending agents, e.g., ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing a compound of the present invention or a combination with suitable non-irritating excipients or carriers, such as cocoa butter, polyethylene glycol or a suppository wax which are solid at ordinary room temperature but liquid at body temperature and therefore melt in the rectum or vaginal cavity thereby releasing the active component(s).

Dosage forms for topical administration of the compounds of the present invention and combinations of the compounds of the present invention with anti-obesity agents may comprise ointments, powders, sprays and inhalants. The drugs are admixed under sterile conditions with a pharmaceutically acceptable excipient, diluent or carrier, and any preservatives, buffers, or propellants that may be required. Ophthalmic formulations, eye ointments, powders, and solutions are also intended to be included within the scope of the present invention.

The following paragraphs describe exemplary formulations, dosages, etc. useful for non-human animals. The administration of the compounds of the present invention and combinations of the compounds of the present invention with anti-obesity agents can be effected orally or non-orally (e.g., by injection).

An amount of a compound of the present invention or combination of a compound of the present invention with an anti-obesity agent is administered such that an effective dose is received. Generally, a daily dose that is administered orally to an animal is between about 0.01 and about 1,000 mg/kg of body weight, preferably between about 0.01 and about 300 mg/kg of body weight.

Conveniently, a compound of the present invention (or combination) can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

Conveniently, a compound of the present invention (or combination) can also be added directly to the feed, as such, or in the form of an animal feed supplement, also referred to as a premix or concentrate. A premix or concentrate of the compound in an excipient, diluent or carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the compound in the finished feed with which the premix is blended. Preferably, the compound is thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of the compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Drinking water and feed effective for increasing lean meat deposition and for improving lean meat to fat ratio are generally prepared by mixing a compound of the present invention with a sufficient amount of animal feed to provide from about $10^{-3}$ to about 500 ppm of the compound in the feed or water.

The preferred medicated swine, cattle, sheep and goat feed generally contain from about 1 to about 400 grams of a compound of the present invention (or combination) per ton of feed, the optimum amount for these animals usually being about 50 to about 300 grams per ton of feed.

The preferred poultry and domestic pet feeds usually contain about 1 to about 400 grams and preferably about 10 to about 400 grams of a compound of the present invention (or combination) per ton of feed.

For parenteral administration in animals, the compounds of the present invention (or combination) may be prepared in the form of a paste or a pellet and administered as an implant, usually under the skin of the head or ear of the animal in which increase in lean meat deposition and improvement in lean meat to fat ratio is sought.

In general, parenteral administration involves injection of a sufficient amount of a compound of the present invention (or combination) to provide the animal with about 0.01 to about 20 mg/kg/day of body weight of the drug. The preferred dosage for poultry, swine, cattle, sheep, goats and domestic pets is in the range of from about 0.05 to about 10 mg/kg/day of body weight of drug.

Paste formulations can be prepared by dispersing the drug in a pharmaceutically acceptable oil such as peanut oil, sesame oil, corn oil or the like.

Pellets containing an effective amount of a compound of the present invention, pharmaceutical composition, or combination can be prepared by admixing a compound of the present invention or combination with a diluent such as carbowax, carnuba wax, and the like, and a lubricant, such as magnesium or calcium stearate, can be added to improve the pelleting process.

It is, of course, recognized that more than one pellet may be administered to an animal to achieve the desired dose level which will provide the increase in lean meat deposition and improvement in lean meat to fat ratio desired. Moreover, implants may also be made periodically during the animal treatment period in order to maintain the proper drug level in the animal's body.

The present invention has several advantageous veterinary features. For the pet owner or veterinarian who wishes to increase leanness and/or trim unwanted fat from pet animals, the instant invention provides the means by which this may be accomplished. For poultry, beef and swine breeders, utilization of the method of the present invention yields leaner animals that command higher sale prices from the meat industry.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), and AstraZeneca Pharmaceuticals (London, England).

General Experimental Procedures

NMR spectra were recorded on a Varian Unity™ 400 or 500 (available from Varian Inc., Palo Alto, Calif.) at room temperature at 400 and 500 MHz $^1$H, respectively. Chemical shifts are expressed in parts per million (δ) relative to residual solvent as an internal reference. The peak shapes are denoted as follows: s, singlet; d, doublet; t, triplet; q, quartet; m, multiplet; br s, broad singlet; v br s, very broad singlet; br m, broad multiplet; 2s, two singlets. In some cases only representative $^1$H NMR peaks are given.

Mass spectra were recorded by direct flow analysis using positive and negative atmospheric pressure chemical ionization (APcI) scan modes. A Waters APcI/MS model ZMD mass spectrometer equipped with Gilson 215 liquid handling system was used to carry out the experiments Mass spectrometry analysis was also obtained by RP-HPLC gradient method for chromatographic separation. Molecular weight identification was recorded by positive and negative electrospray ionization (ESI) scan modes. A Waters/Micromass ESI/MS model ZMD or LCZ mass spectrometer equipped with Gilson 215 liquid handling system and HP 1100 DAD was used to carry out the experiments.

Where the intensity of chlorine or bromine-containing ions are described, the expected intensity ratio was observed (approximately 3:1 for $^{35}$Cl/$^{37}$Cl-containing ions and 1:1 for $^{79}$Br/$^{81}$Br-containing ions) and only the lower mass ion is given. MS peaks are reported for all examples.

Optical rotations were determined on a PerkinElmer™ 241 polarimeter (available from PerkinElmer Inc., Wellesley, Mass.) using the sodium D line (λ=589 nm) at the indicated temperature and are reported as follows [α]$_D^{temp}$, concentration (c=g/100 ml), and solvent.

Column chromatography was performed with either Baker™ silica gel (40 μm; J. T. Baker, Phillipsburg, N.J.) or Silica Gel 50 (EM Sciences™, Gibbstown, N.J.) in glass columns or in Biotage™ columns (ISC, Inc., Shelton, Conn.) under low nitrogen pressure. Radial chromatography was performed using a Chromatotron™ (Harrison Research).

Preparation of Key Intermediates

Preparation of Intermediate 5-(2-Chlorophenyl)-2H-Pyrazol-3-ylamine (I-1A-1a)

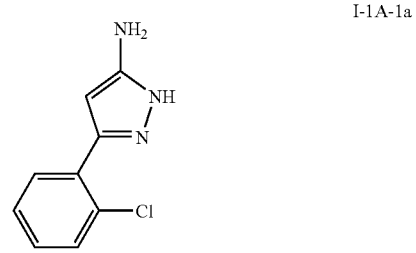

I-1A-1a

A solution of 2-chlorobenzoylacetonitrile (15.9 g, 89 mmol) and hydrazine hydrate (8.9 g, 0.18 mol) in ethanol (2 ml) was heated at reflux for 22 hr. After cooling to room temperature, the reaction was concentrated, in vacuo. The residue was dissolved in ethyl acetate, washed with water and brine, dried (MgSO$_4$), and concentrated, in vacuo, to a brown oil. Flash chromatography using 10% ethyl acetate in methylene chloride, changing to 5% methanol in methylene chloride as eluant afforded title product I-1A-1a (17.3 g, quantitative): +ESI MS (M+1) 194.2; $^1$H NMR (400 MHz, CD$_3$OD) δ 7.60–7.25 (m, 4H), 5.99 (br s, 1H).

Preparation of Intermediate 2-(2-Chlorophenyl)-4H-pyrazolo[1,5-a]pyrimidin-7-one (I-1A-1b)

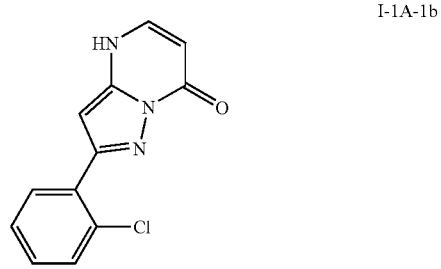

I-1A-1b

A solution of 5-(2-chlorophenyl)-2H-pyrazol-3-ylamine (I-1A-1a; 287 g, 1.48 mol) and ethyl formylacetate sodium salt (517 g, 3.74 mol) in ethanol (12 L) was heated at reflux for 6 hours. Additional ethyl formylacetate sodium salt (100 g, 0.72 mol) was added, and the reaction was heated at reflux for an additional 2 hours. After cooling to room temperature, the reaction was concentrated, in vacuo, to give an amber oil. The residue was redissolved in water (2 L) and then adjusted to pH 8 by dropwise addition of concentrated aqueous HCl. The solid precipitate that formed was isolated by vacuum filtration. This material was suspended in tetrahydrofuran (3 liters) and then stirred overnight. The solid was isolated by vacuum filtration and then dried, in vacuo, to afford I-1A-1b as an off-white solid (356 g, 98%): +APcI MS (M+1) 246.2; $^1$H NMR (400 MHz, DMSO-d$_6$) δ 7.89 (d, J=7.5 Hz, 1H), 7.85–7.82 (m, 1H), 7.58–7.53 (m, 1H), 7.46–7.41 (m, 2H), 6.58 (s, 1H), 5.71 (d, J=7.1 Hz, 1H).

Preparation of Intermediate 7-Chloro-2-(2-chlorophenyl)-pyrazolo[1,5-a]pyrimidine (I-1A-1c)

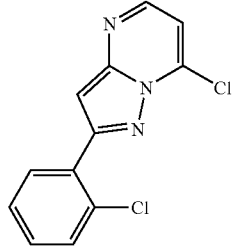

I-1A-1c

To a slurry of 2-(2-chlorophenyl)-4H-pyrazolo[1,5-a]pyrimidin-7-one (I-1A-1b; 30.0 g, 122 mmol) and triethylamine (25.5 ml, 183 mmol) in toluene (1.3 liters) at room temperature was added $POCl_3$ (58 ml, 0.62 mol), dropwise. The mixture was heated at 95° C. for 4 hours, cooled to room temperature, then slowly added to a stirred mixture of ice, sodium bicarbonate (300 g) and ethyl acetate (1 liter), keeping the temperature at 0° C. The aqueous layer was separated and extracted with additional ethyl acetate. The combined organic layers were dried ($MgSO_4$), and then concentrated, in vacuo, to afford an amber solid. This material was purified by silica gel chromatography using 2:1:0.1 methylene chloride/hexanes/methanol as eluant to afford I-1A-1c as a colorless solid (17.5 g, 54%): +APcI MS (M+1) 264.2; $^1$H NMR (400 MHz, $CD_2Cl_2$) δ 8.40 (d, J=4.6 Hz, 1H), 8.00–7.97 (m, 1H), 7.56–7.53 (m, 1H), 7.45–7.39 (m, 2H), 7.34 (s, 1), 7.03 (d, J=4.6 Hz, 1H).

Preparation of Intermediate 7-Chloro-2-(2-chlorophenyl)-3-iodopyrazolo[1,5-a]pyrimidine (I-1A-1d)

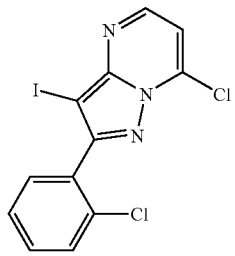

I-1A-1d

To a solution of 7-chloro-2-(2-chlorophenyl)-pyrazolo[1,5-a]pyrimidine (I-1A-1c; 6.00 g, 22.7 mmol) in chloroform (23 ml) and methylene chloride (207 ml) cooled in an ice bath was added N-iodosuccinimide (7.67 g, 34.1 mmol), portionwise. The ice bath was removed and the reaction was stirred overnight at room temperature. After concentrating the red-brown reaction, in vacuo, an ethyl acetate solution of the residue was washed with saturated aqueous $Na_2S_2O_4$ and brine. The solution was dried ($MgSO_4$), concentrated, in vacuo, and the resulting solids repulped at room temperature from ethyl acetate (30 ml) to give product I-1A-1d as a solid (6.8 g, 77%): +APcI MS (M+1) 390.1; $^1$H NMR (400 MHz, $CD_2Cl_2$) δ 8.52 (d, J=4.6 Hz, 1H), 7.59–7.56 (m, 1H), 7.53–7.42 (m, 3H), 7.14 (d, J=4.6 Hz, 1H).

Preparation of Intermediate 1-Benzyl-4-ethylaminopiperidine-4-carbonitrile (I-1A-1e)

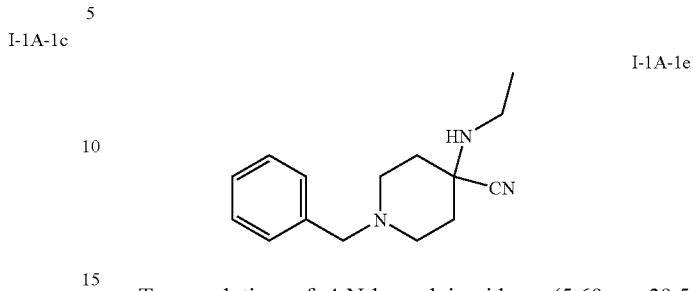

I-1A-1e

To a solution of 4-N-benzylpiperidone (5.69 g, 29.5 mmol) in ethanol (4.2 ml) cooled in an ice bath was added ethylamine hydrochloride (2.69 g, 32.3 mmol) in water (3 ml), keeping the internal temperature of the reaction below 10° C. A solution of KCN (2.04 g, 31.3 mmol) in water (7 ml) was added to the reaction solution over 10 minutes while keeping the internal temperature below 10° C. The reaction was then warmed to room temperature and stirred 18 hours. Isopropanol (10 ml) was added to the reaction mixture to give two distinct layers: lower colorless aqueous layer and an orange organic upper layer. The organic layer was separated and stirred with water (30 ml) for 30 minutes. The organic layer was separated (orange organic layer now the bottom layer), the solvent was removed in vacuo, and the resultant oil diluted in methylene chloride (30 ml). The organic layer was washed with brine, dried ($Na_2SO_4$), filtered and concentrated, in vacuo, to give I-1A-1e as an orange oil (6.05 g, 84%): +APcI MS (M+1) 244.2; 1H NMR (400 MHz, $CD_2Cl_2$) δ 7.32 (d, J=4.1 Hz, 4H), 7.29–7.23 (m, 1H), 3.54 (s, 2H), 2.81–2.76 (m, 2H), 2.75 (q, J=7.1 Hz, 2H), 2.35–2.29 (m, 2H), 2.01–1.98 (m, 2H), 1.74–1.68 (m, 2H), 1.14 (t, J=7.1 Hz, 3H).

Preparation of Intermediate 1-Benzyl-4-ethylaminopiperidine-4-carboxylic Acid Amide (I-1A-1f)

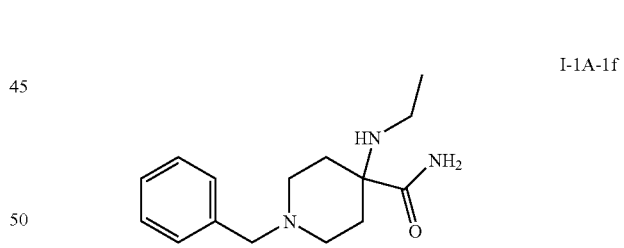

I-1A-1f

A solution of 1-benzyl-4-ethylaminopiperidine-4-carbonitrile I-1A-1e (0.58 g, 2.38 mmol) in methylene chloride (2 ml) cooled in an ice bath was treated with $H_2SO_4$ (1.8 ml, 33 mmol), dropwise, while keeping the internal temperature below 20° C. The reaction was then warmed to room temperature and stirred for 19 hours. After stirring was discontinued, the thick pale orange $H_2SO_4$ bottom layer was separated, cooled in an ice bath and then carefully quenched with concentrated $NH_4OH$ keeping internal temperature below 55° C. The aqueous layer was extracted with methylene chloride (2×10 ml), the combined organic layers were washed with brine (20 ml), dried ($Na_2SO_4$), and then concentrated, in vacuo, to afford I-1A-1f as a pale orange oil that solidified to a peach colored solid upon standing (0.54 g, 87%): +APcI MS (M+1) 262.2; $^1$H NMR (400 MHz, CD$_2$Cl$_2$) δ 7.34–7.30 (m, 4H), 7.29–7.21 (m, 1H), 7.16 (br s, 1H), 3.48 (s, 2H), 2.71–2.68 (m, 2H), 2.47 (q, J=7.0 Hz, 2H), 2.17–2.02 (m, 4H), 1.62–1.58 (m, 2H), 1.41 (br s, 1H), 1.09 (t, J=7.0 Hz, 3H).

Preparation of Intermediate
4-Ethylaminopiperidine-4-carboxylic Acid Amide
(I-1A-1g)

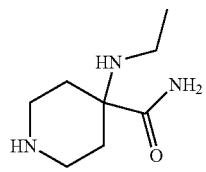

I-1A-1g

To a solution of 1-benzyl-4-ethylaminopiperidine-4-carboxylic acid amide (I-1A-1f; 7.39 g, 28.3 mmol) in methanol (100 ml) was added 20% Pd(OH)$_2$ on carbon (50% water; 1.48 g). The mixture was placed on a Parr® shaker and then reduced (50 psi H$_2$) at room temperature overnight. The mixture was filtered through a pad of Celite®, and then concentrated to give a colorless solid I-1A-1g (4.84 g, quantitative): +APcI MS (M+1) 172.2; $^1$H NMR (400 MHz, CD$_2$Cl$_2$) δ 2.89 (ddd, J=12.9, 8.7, 3.3 Hz, 2H), 2.75 (ddd, J=12.9, 6.6, 3.7 Hz, 2H), 2.45 (q, J=7.2 Hz, 2H), 1.95 (ddd, J=13.7, 8.3, 3.7 Hz, 2H), 1.55 (ddd, J=13.7, 6.6, 3.3 Hz, 2h), 1.08 (t, J=7.1 Hz, 3H).

Preparation of Intermediate
1-Benzhydryl-3-benzylaminoazetidine-3-carbonitrile
(I-1A-3a)

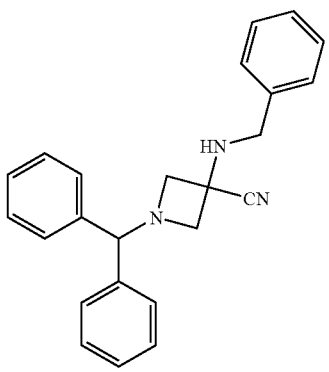

I-1A-3a

To a solution of 1-benzhydrylazetidin-3-one (3.3 g, 14 mmol) in methanol (35 ml) was added benzylamine (1.6 ml, 15 mmol) and then acetic acid (0.88 ml, 15 mmol) at room temperature. After stirring for 45 minutes, solid NaCN (0.76 g, 15 mmol) was added in portions over 2 minutes and the mixture was heated to reflux overnight. The reaction, which now contained a precipitate, was cooled and then stirred at room temperature. The solids were collected by vacuum filtration, rinsed with a small volume of cold methanol, and then dried, in vacuo, to give I-1A-3a as a solid (3.56 g, 72%): +APcI MS (M+1) 354.4; $^1$H NMR (400 MHz, CD$_3$OD) δ 7.40 (d, J=7.5 Hz, 4H), 7.35 (d, J=7.5 Hz, 2H), 7.31–7.20 (m, 7H), 7.16 (t, J=7.3 Hz, 2H), 4.44 (s, 1H), 3.76 (s, 2H), 3.48 (d, J=8.3 Hz, 2H), 3.05 (d, J=8.3 Hz, 2H).

Preparation of Intermediate
1-Benzhydryl-3-benzylaminoazetidine-3-carboxylic
Acid Amide (I-1A-3b)

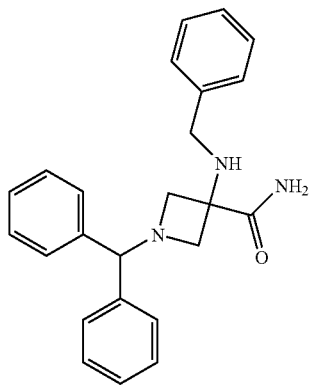

I-1A-3b

A solution of 1-benzhydryl-3-benzylaminoazetidine-3-carbonitrile I-1A-3a (3.45 g, 9.76 mmol) in methylene chloride (55 ml) cooled in an ice bath was treated with H$_2$SO$_4$ (8.1 ml, 0.15 mol), dropwise. After the reaction mixture was allowed to warm to room temperature and stir overnight, it was cooled in an ice bath and then carefully quenched with concentrated aqueous NH$_4$OH to pH 10. The mixture was extracted with methylene chloride; the combined organic layers were washed with brine, dried (Na$_2$SO$_4$) and then concentrated, in vacuo, to afford a brown solid. Trituration of this material from hexanes/diethyl ether afforded a light tan solid which was collected by vacuum filtration, washed with additional hexanes and dried, in vacuo, to give I-1A-3b (3.34 g, 92%): +ESI MS (M+1) 372.4; $^1$H NMR (400 MHz, CD$_3$OD) δ 7.41 (d, J=7.5 Hz, 4H), 7.35 (d, J=7.5 Hz, 2H), 7.31–7.22 (m, 7H), 7.16 (t, J=7.7 Hz, 2H), 4.50 (s, 1H), 3.60 (s, 2H), 3.48 (d, J=8.3 Hz, 2H), 3.16 (d, J=8.3 Hz, 2H).

Preparation of Intermediate 1-Benzhydryl-3-(benzylethylamino)-azetidine-3-carboxylic Acid Amide,
Hydrochloride Salt (I-1A-3c)

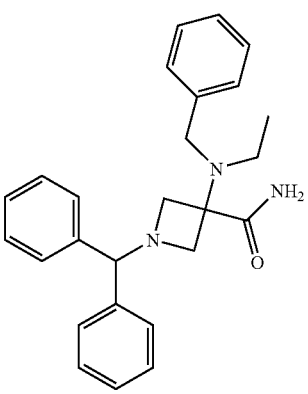

I-1A-3c

A suspension of 1-benzhydryl-3-benzylaminoazetidine-3-carboxylic acid amide I-1A-3b (3.06 g, 8.24 mmol) in methanol (80 ml) cooled in an ice bath was treated with acetic acid (2.4 ml, 41 mmol), sodium acetate (6.8 g, 82 mmol) and acetaldehyde (1.8 ml, 41 mmol). After stirring for 10 minutes, NaCNBH$_3$ (6.24 mg, 9.9 mmol) was added, portionwise. After stirring for 45 minutes, the mixture was allowed to warm to room temperature and stir overnight. The reaction was concentrated, in vacuo, and the residue then extracted from saturated aqueous sodium bicarbonate with ethyl acetate. The combined organic layers were washed with brine, dried (MgSO$_4$), and then concentrated, in vacuo, to afford the crude product (3.8 g): +APcI MS (M+1) 400.5; $^1$H NMR (400 MHz, CD$_2$Cl$_2$) δ 7.41–7.37 (m, 6H), 7.29–7.22 (m, 6H), 7.20–7.12 (m, 3H), 4.44 (s, 1H), 3.74 (s, 2H), 3.47 (d, J=8.3 Hz, 2H), 3.12 (d, J=8.3 Hz, 2H), 2.56 (q, J=7.2 Hz, 2H), 0.85 (t, J=7.1 Hz, 3H).

For purification, a solution of the free base in methanol (75 ml) was treated with 1M HCl in diethyl ether (21 ml), dropwise over 5 minutes. After stirring for 20 minutes, the mixture was concentrated under reduced pressure followed by concentration from addition methanol (2×) and then ethanol. The residue was suspended and stirred in isopropanol (3 ml) while diethyl ether (50 ml) was slowly added. After stirring for 45 minutes, the solids were isolated by vacuum filtration, washed with ether and then dried, in vacuo, to provide I-1A-3c (4.4 g, quantitative): +APcI MS (M+1) 400.5; $^1$H NMR (400 MHz, CD$_3$OD) δ 7.55–7.25 (br m, 15H), 5.76 (br s, 1H), 4.21 (br s, 4H), 3.93 (v br s, 2H), 1.02 (br s, 3H).

Preparation of Intermediate
1-Benzhydryl-3-ethylaminoazetidine-3-carboxylic
Acid Amide (I-1A-3d)

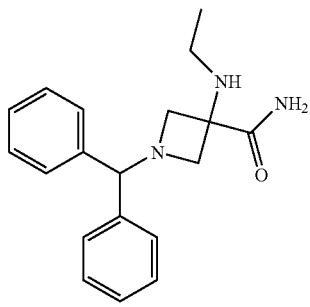

I-1A-3d

To a solution of 1-benzhydrylazetidin-3-one (53.4 g, 225 mmol) in methanol (750 ml) was added ethylamine hydrochloride (20.2 g, 243 mmol), KCN (15.4 g, 229 mmol) and then acetic acid (14.3 ml, 247 mmol) at room temperature. After stirring for 2.5 hours at room temperature, at which point the starting ketone had been consumed, the mixture was heated at 55° C. for 15 hours. The reaction was cooled to 50° C. and then treated with methyl sulfoxide (19.2 ml, 270 mmol), followed by 2N aqueous NaOH (251 ml) over a 10-minute period. A solution of 11% aqueous peroxide (80 ml, 247 mmol) was added over 5 minutes (exothermic reaction), during which time a precipitate formed. Additional water (270 ml) was added to aid stirring. After cooling to room temperature and stirring for an additional hour, the solids were collected on a sintered funnel, washed with water, and then dried, in vacuo, to give crude I-1A-3d (55.3 g, 79%) as a solid.

For purification purposes, crude 1-benzhydryl-3-ethylaminoazetidine-3-carboxylic acid amide (I-1A-3d; 83.0 g, 268 mmol) was added to 1 M HCl (1.3 l), portionwise. After washing the solution with methylene chloride (1 l, then 0.8 l), the mixture was treated with 50% aqueous NaOH (130 ml) to bring the pH=10. The precipitate that formed on basification were collected on a sintered funnel, washed with water, and then dried, in vacuo, to give I-1A-3d (72.9 g, 88%) as a colorless solid: +ESI MS (M+1) 310.5; $^1$H NMR (400 MHz, CD$_3$OD) δ 7.41 (d, J=7.1 Hz, 4H), 7.25 (t, J=7.5 Hz, 4H), 7.16 (t, J=7.5 Hz, 2H), 4.49 (s, 1H), 3.44 (d, J=8.3 Hz, 2H), 3.11 (d, J=8.3 Hz, 2H), 2.47 (q, J=7.1 Hz, 2H), 1.10 (t, J=7.3 Hz, 3H).

Preparation of Intermediate
3-Ethylaminopiperidine-3-carboxylic Acid Amide,
Hydrochloride Salt (I-1A-3e)

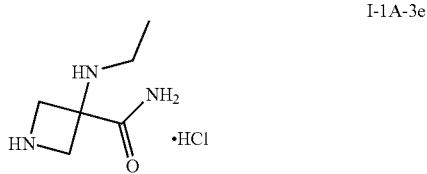

I-1A-3e

To a solution of 1-benzhydryl-3-(benzylethylamino)-azetidine-3-carboxylic acid amide hydrochloride salt (I-1A-3c; 0.66 g, 1.4 mmol) in methanol (25 ml) was added 20% Pd(OH)$_2$ on carbon (30% water; 0.13 g). The mixture was placed on a Parr® shaker and then reduced (45 psi H$_2$) at room temperature overnight. The mixture was diluted with methanol (200 ml) filtered through a 0.45 μm filter disk, and then concentrated to a solid. The residue was triturated from diethyl ether, collected by vacuum filtration, washed with ether and then dried, in vacuo, to afford I-1A-3e (298 mg, 98%): +APcI MS (M+1) 144.1; $^1$H NMR (400 MHz, CD$_2$Cl$_2$) δ 4.56 (br s, 4H), 3.00 (q, J=7.2 Hz, 2H), 1.36 (t, J=7.1 Hz, 3H).

Alternate Preparation of Intermediate
3-Ethylaminopiperidine-3-carboxylic Acid Amide,
Hydrochloride Salt (I-1A-3e)

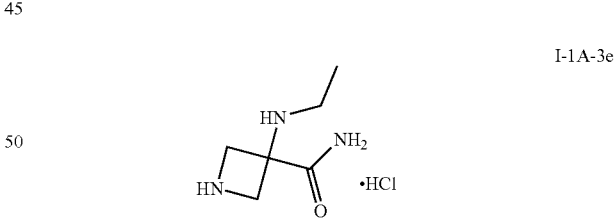

I-1A-3e

To a suspension of 1-benzhydryl-3-ethylaminoazetidine-3-carboxylic acid amide (I-1A-3d; 36.1 g, 117 mmol) in methanol (560 ml) at room temperature was added concentrated aqueous HCl (19.5 ml, 234 mmol), resulting in a clear solution. To 20% Pd(OH)$_2$ on carbon (3.75 g) was added methanol (85 ml), followed by the methanolic solution of I-1A-3d. The mixture was placed on a Parr® shaker and then reduced (50 psi H$_2$) at room temperature for 20 hours. The reaction was then filtered through Celite® and then concentrated to low volume under reduced pressure, at which point a precipitate formed. The suspension was diluted with MTBE (500 ml), stirred for an additional hour, and the precipitate collected by vacuum filtration. The solid was washed with MTBE and then dried, in vacuo, to afford I-1A-3e (24.8 g, 98%) as a colorless solid.

Preparation of Intermediate 2-(2-Chlorophenyl)-5-methylpyrazolo[1,5-a]pyrimidin-7-ol (I-1A-3f)

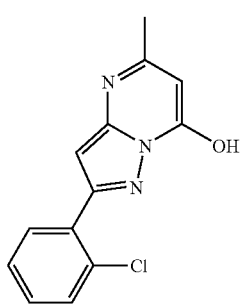

I-1A-3f

To a solution of 5-(2-chlorophenyl)-2H-pyrazol-3-ylamine (I-1A-1a; 1.51 g, 7.80 mmol) in acetic acid (10 ml) was added ethyl acetoacetate (1.1 ml, 8.6 mmol). The reaction was heated at reflux for 17 hours. Upon cooling to room temperature a solid precipitate formed which, after standing for 2 days, was isolated by vacuum filtration and washed with additional acetic acid. The solids were stirred in ether and then isolated by vacuum filtration to afford I-1A-3f as a colorless solid (1.52 g, 75%): +ESI MS (M+1) 260.2; $^1$H NMR (400 MHz, DMSO-$d_6$) δ 12.18 (br s, 1H), 7.85–7.81 (m, 1H), 7.57–7.54 (m, 1H), 7.46–7.41 (m, 2H), 6.49 (s, 1H), 5.61 (s, 1H), 2.29 (s, 3H).

Preparation of Intermediate 7-Chloro-2-(2-chlorophenyl)-5-methylpyrazolo[1,5-a]pyrimidine (I-1A-3g)

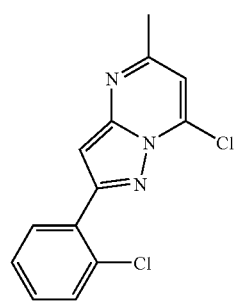

I-1A-3g

To a slurry of 2-(2-chlorophenyl)-5-methylpyrazolo[1,5-a]pyrimidin-7-ol (I-1A-3f; 700 mg, 2.70 mmol) and triethylamine (0.57 ml, 4.0 mmol) in toluene (30 ml) at room temperature was added POCl$_3$ (1.3 ml, 14 mmol), dropwise. The mixture was heated at 95° C. for 21 hours, cooled to room temperature, then slowly added to a stirred mixture of ice, saturated aqueous sodium bicarbonate and ethyl acetate. The aqueous layer was separated and extracted with additional ethyl acetate. The combined organic layers were washed with brine, dried (MgSO$_4$), and then concentrated, in vacuo, to afford the crude product (0.79 g). Purification on a Biotage™ Flash 40S column using 0–20% ethyl acetate in hexanes as eluant afforded I-1A-3g as an off-white solid (643 mg, 86%): +ESI MS (M+1) 278.12; $^1$H NMR (400 MHz, CD$_2$Cl$_2$) δ 7.96–7.93 (m, 1H), 7.54–7.51 (m, 1H), 7.50–7.35 (m, 2H), 7.15 (s, 1H), 6.90 (s, 1H), 2.59 (s, 3H).

Preparation of Intermediate 7-Chloro-2-(2-chlorophenyl)-3-iodo-5-methylpyrazolo[1,5-a]pyrimidine (I-1A-3h)

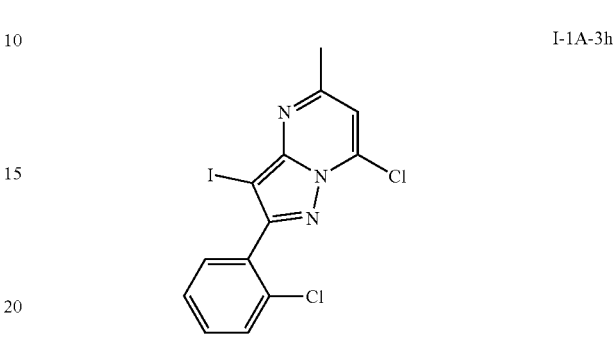

I-1A-3h

To a solution of 7-chloro-2-(2-chlorophenyl)-5-methylpyrazolo[1,5-a]pyrimidine (I-1A-3g; 370 mg, 1.33 mmol) in 5:1 methylene chloride/chloroform (9 ml) cooled in an ice bath was added N-iodosuccinimide (449 mg, 2.0 mmol), portionwise, to give a heterogeneous mixture. After 1.5 hours, the ice bath was removed and the reaction was stirred an additional 2.5 hours to give a homogenous, pink solution. The reaction was extracted from aqueous NaHCO$_3$ with methylene chloride. The combined extracts were washed with saturated aqueous Na$_2$S$_2$O$_4$ and brine, dried (MgSO$_4$), and then concentrated, in vacuo, to afford product I-1A-3h as a tan solid (535 mg, quantitative): +ESI MS (M+1) 403.9; $^1$H NMR (400 MHz, CD$_2$Cl$_2$) δ 7.57–7.40 (m, 4H), 6.99 (s, 1H), 2.66 (s, 3H).

Preparation of Intermediate 3-(2-Chlorophenyl)-2-(4-chlorophenyl)-3-oxopropionitrile (1–3A-1a)

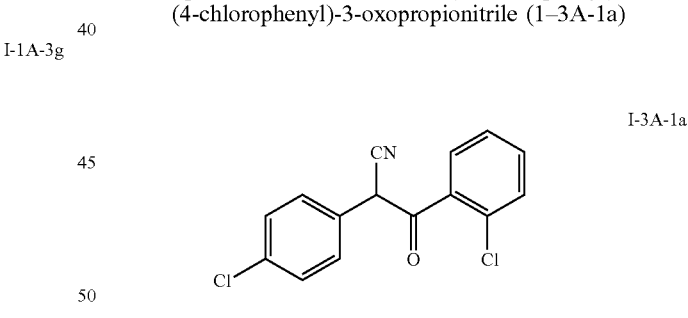

I-3A-1a

To a solution of (4-chlorophenyl)acetonitrile (15.1 g, 100 mmol) in THF (250 ml) was added NaH (60% dispersion in oil, 8.0 g, 200 mmol) in 3 portions over 5 minutes. To this was added a solution of 2-chlorobenzoic acid ethyl ester (18.3 g, 100 mmol) in THF (50 ml), dropwise over 10 minutes. The mixture was then heated at 60° C. overnight. After cooling to room temperature, water was added (2×10 ml, bubbling observed), and the reaction was concentrated, in vacuo, to ½ volume. The mixture was diluted with water (125 ml) and methylene chloride (125 ml), adjusted to pH=7 with 3 N aqueous HCl, and the aqueous layer separated and extracted with additional methylene chloride. The combined organics were dried (MgSO$_4$) and concentrated, in vacuo, to give a brown oil (33 g) that began to solidify on standing. After stirring the residue overnight in diisopropyl ether (250 ml), the solid product was collected by vacuum filtration to afford, after drying, in vacuo, title product I-3A-1a (15.2 g, 52%) as a tan solid: −ESI MS (M−1) 288.0; $^1$H NMR (400 MHz, CD$_2$Cl$_2$) δ 7.74 (d, J=8.30 Hz, 1H), 7.60–7.25 (m, 7H), 5.65 (s, 1H).

Preparation of Intermediate 5-(2-Chlorophenyl)-4-(4-chlorophenyl)-2H-pyrazol-3-ylamine (I-3A-1b)

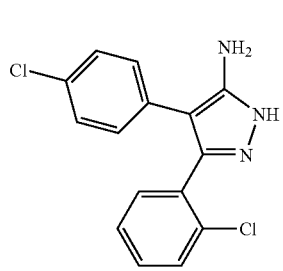

I-3A-1b

To a solution of 3-(2-chlorophenyl)-2-(4-chlorophenyl)-3-oxopropionitrile (I-3A-1a; 13.8 g, 47.6 mmol) in toluene (150 ml) was added hydrazine hydrate (4.62 ml, 95.2 mmol) and then acetic acid (6.82 ml, 119 mmol), each dropwise. The reaction was heated at reflux for 7 hours and then cooled and diluted with ethyl acetate (300 ml). The organic layer was washed with saturated aqueous NaHCO$_3$ (2×) and brine. The combined aqueous layers were adjusted to pH=11 with 5 N aqueous NaOH and then extracted with ethyl acetate (2×). The combined organic layers were dried (MgSO$_4$) and concentrated, in vacuo, to an oil (13.7 g). Flash chromatography using 0–5% methanol in methylene chloride as eluant afforded an oil (5.6 g) which contained the desired material. The residue was thinned with a small amount of ethyl acetate, and then slowly added to stirred diisopropyl ether. After filtration to remove precipitated solids, the filtrate was concentrated, in vacuo, to give title product I-3A-1b (3.97 g, 27%) as a tan foam: +ESI MS (M+1) 304.1; $^1$H NMR (400 MHz, CD$_3$OD) δ 7.45–7.25 (m, 4H), 7.20 (d, J=8.7 Hz, 2H), 7.09 (d, J=8.7 Hz, 2H).

Preparation of Intermediate 3-(4-Chlorophenyl)-2-(2-chlorophenyl)-6-methylpyrazolo[1,5-a]pyrimidin-7-ol (I-3A-1c)

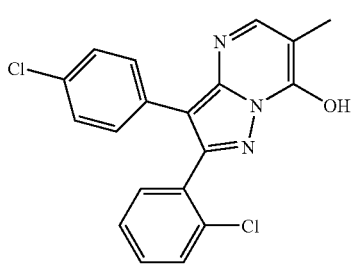

I-3A-1c

To a mixture of 5-(2-chlorophenyl)-4-(4-chlorophenyl)-2H-pyrazol-3-ylamine (I-3A-1b; 393 mg, 1.29 mmol) in acetic acid (4.3 ml) was added 3-hydroxy-2-methylacrylic acid ethyl ester sodium salt (590 mg, 3.88 mmol), portionwise. The reaction was heated at 100° C. for 2 hours (precipitate formed after 35 minutes). After cooling to room temperature, the precipitated solid was isolated by vacuum filtration and then repulped from diethyl ether to afford I-3A-1c as a colorless solid (141 mg, 30%): +ESI MS (M+1) 370.0; $^1$H NMR (400 MHz, DMSO-d$_6$) δ 12.14 (br s, 1H), 7.75 (s, 1H), 7.50–7.38 (m, 4H), 7.32 (d, J=8.7 Hz, 2H), 7.17 (d, J=8.7 Hz, 2H), 2.01 (s, 3H).

Preparation of Intermediate 7-Chloro-3-(4-chlorophenyl)-2-(2-chlorophenyl)-6-methylpyrazolo[1,5-a]pyrimidine (I-3A-1d)

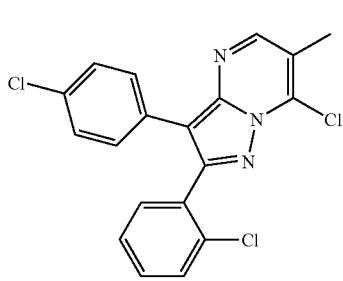

I-3A-1d

To a slurry of 3-(4-chlorophenyl)-2-(2-chlorophenyl)-6-methylpyrazolo[1,5-a]pyrimidin-7-ol (I-3A-1c; 119 mg, 0.321 mmol) and diisopropylethylamine (0.084 ml, 0.48 mmol) in toluene (2.2 ml) at room temperature was added POCl$_3$ (0.15 ml, 1.61 mmol), dropwise. The mixture was heated at 100° C. for 22 hours, cooled to room temperature, then slowly added to a stirred mixture of ice, saturated aqueous sodium bicarbonate and ethyl acetate. The aqueous layer was separated and extracted with additional ethyl acetate. The combined organic layers were washed with brine, dried (MgSO$_4$), and then concentrated, in vacuo, to afford the crude product (120 mg). Purification on a Biotage™ Flash 12M column using 0–8% ethyl acetate in hexanes as eluant afforded I-3A-1d (102 mg, 82%) as a yellow solid: +ESI MS (M+1) 388.1; $^1$H NMR (400 MHz, CD$_2$Cl$_2$) δ 8.44 (s, 1H), 7.55–7.37 (m, 6H), 7.27 (d, J=8.7 Hz, 2H), 2.51 (s, 3H).

Preparation of Intermediate
1-Benzhydryl-3-methylaminoazetidine-3-carbonitrile
(I-3A-2a)

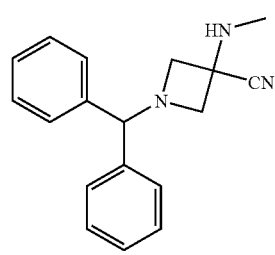

I-3A-2a

To a solution of 1-benzhydrylazetidin-3-one (2.13 g, 8.98 mmol) in methanol (17 ml) was added methylamine hydrochloride (1.21 g, 18.0 mmol) and then acetic acid (1.03 ml, 18.0 mmol) at room temperature. After stirring for 5 minutes, solid KCN (1.17 g, 18.0 mmol) was added and the mixture was heated to 60° C. for 19 hours. The reaction was cooled; the solid product was collected by vacuum filtration, rinsed with methanol, and then dried, in vacuo, to afford I-3A-2a as a colorless solid (2.50 g, quantitative): +ESI MS (M+1) 278.3; $^1$H NMR (400 MHz, CD$_2$Cl$_2$) δ 7.43 (d, J=7.5 Hz, 4H), 7.29 (t, J=7.5 Hz, 4H), 7.23 (t, J=7.3 Hz, 2H), 4.45 (s, 1H), 3.55 (d, J=7.5 Hz, 2H), 3.15 (d, J=7.1 Hz, 2H), 2.40 (s, 3H).

Preparation of Intermediate
1-Benzhydryl-3-methylaminoazetidine-3-carboxylic Acid Amide (I-3A-2b)

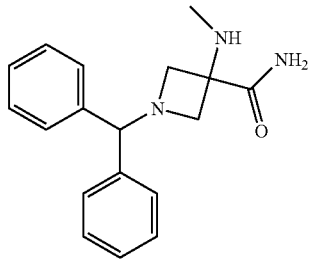

I-3A-2b

A vigorously stirred solution of 1-benzhydryl-3-methylaminoazetidine-3-carbonitrile (I-3A-2a; 2.10 g, 7.57 mmol) in methylene chloride (25 ml) cooled in an ice bath was treated with H$_2$SO$_4$ (4.0 ml, 76 mmol), dropwise. After the reaction mixture was allowed to warm to room temperature and stir overnight, it was cooled in an ice bath and then carefully quenched with concentrated aqueous NH$_4$OH to pH 11. The mixture was extracted with methylene chloride; the combined organic layers were dried (Na$_2$SO$_4$) and then concentrated, in vacuo, to afford I-3A-2b (1.2 g, 54%) as an off-white solid: +ESI MS (M+1) 296.3; $^1$H NMR (400 MHz, CD$_3$OD) δ 7.41 (d, J=7.5 Hz, 4H), 7.25 (t, J=7.5 Hz, 4H), 7.16 (t, J=7.1 Hz, 2H), 4.48 (s, 1H), 3.41 (d, J=8.7 Hz, 2H), 3.09 (d, J=8.7 Hz, 2H), 2.24 (s, 3H).

Preparation of Intermediate
3-Methylaminoazetidine-3-carboxylic Acid Amide, Hydrochloride Salt (I-3A-2c)

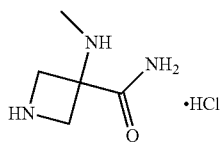

I-3A-1c

To a suspension of 1-benzhydryl-3-methylaminoazetidine-3-carboxylic acid amide (I-3A-2b; 13.5 g, 45.8 mmol) in methanol (90 ml) was added concentrated aqueous HCl (8.0 ml, 96 mol), dropwise, to give a homogeneous solution. After the addition of 20% Pd(OH)$_2$ on carbon (50% water; 4.1 g), the mixture was placed on a Parr® shaker and then reduced (50 psi H$_2$) at room temperature for 7 hours. The mixture was filtered through a pad of Celite®, washing with copious amount of 9:1 methanol/water, and then 9:1 tetrahydrofuran/water until no product eluted (determined with ninhydrin stain). The filtrate was then concentrated, in vacuo, and the residue triturated from diethyl ether to give I-3A-2c (9.3 g, quantitative) as a brown solid: +APcI MS (M+1) 129.9; $^1$H NMR (400 MHz, CD$_3$OD) δ 4.50 (d, J=12.0 Hz, 2H), 4.43 (d, J=12.9 Hz, 2H), 2.64 (s, 3H).

Preparation of Intermediate 3-(4-Chlorophenyl)-2-(2-chlorophenyl)-5-methylpyrazolo[1,5-a]pyrimidin-7-ol (I-3A-4a)

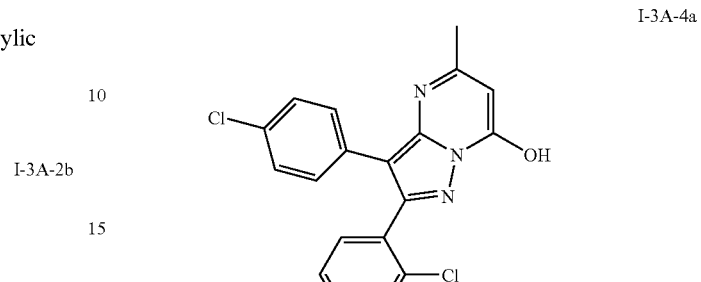

I-3A-4a

To a mixture of 5-(2-chlorophenyl)-4-(4-chlorophenyl)-2H-pyrazol-3-ylamine (I-3A-1b; 3.00 g, 9.86 mmol) in acetic acid (12 ml) was added ethyl acetoacetate (1.63 ml, 12.8 mmol). The reaction was heated at 100° C. for 16 hours. After cooling to room temperature, the precipitated solid was isolated by vacuum filtration and then repulped from diethyl ether to afford I-3A-4a (1.1 g, 30%) as a colorless solid: +ESI MS (M+1) 370.0; $^1$H NMR (400 MHz, DMSO-d$_6$) δ 12.12 (s, 1H), 7.45–7.33 (m, 6H), 7.13 (d, J=8.7 Hz, 2H), 5.70 (s, 1H), 2.30 (s, 3H).

Preparation of Intermediate 7-Chloro-3-(4-chlorophenyl)-2-(2-chlorophenyl)-5-methylpyrazolo[1,5-a]pyrimidine (I-3A-4b)

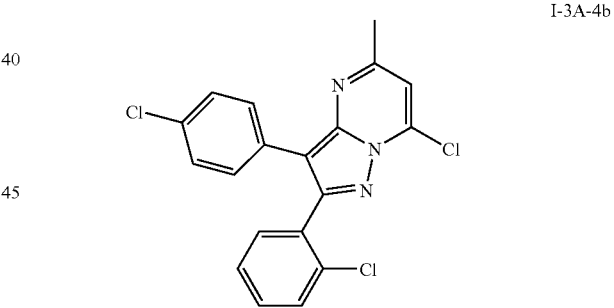

I-3A-4b

To a slurry of 3-(4-chlorophenyl)-2-(2-chlorophenyl)-5-methylpyrazolo[1,5-a]pyrimidin-7-ol (I-3A-4a; 1.08 g, 2.92 mmol) and diisopropylethylamine (0.763 ml, 4.38 mmol) in toluene (30 ml) at room temperature was added POCl$_3$ (1.36 ml, 14.6 mmol), dropwise. The mixture was heated at 100° C. for 16 hours, cooled to room temperature, then slowly added to a stirred mixture of ice, saturated aqueous sodium bicarbonate and ethyl acetate. The aqueous layer was separated and extracted with additional ethyl acetate. The combined organic layers were washed with brine, dried (MgSO$_4$), and then concentrated, in vacuo, to afford the crude product. Purification on a Biotage™ Flash 40M column using 0–10% ethyl acetate in hexanes as eluant afforded I-3A-4b (1.05 g, 92%) as a yellow solid: +ESI MS (M+1) 388.1; $^1$H NMR (400 MHz, CD$_2$Cl$_2$) δ 7.55–7.35 (m, 6H), 7.26 (d, J=8.7 Hz, 2H), 6.98 (s, 1H), 2.64 (s, 3H).

Preparation of Intermediate 3-(4-Chlorophenyl)-2-(2-chlorophenyl)-5,6-dimethylpyrazolo[1,5-a]pyrimidin-7-ol (I-4A-1a)

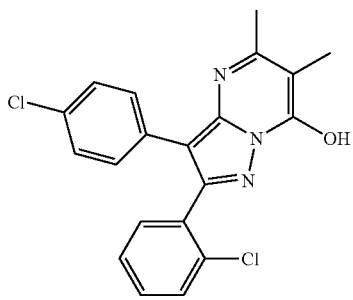

To a mixture of 5-(2-chlorophenyl)-4-(4-chlorophenyl)-2H-pyrazol-3-ylamine (I-3A-1b; 0.642 g, 2.11 mmol) in acetic acid (2.6 ml) was added 2-methyl-3-oxobutyric acid ethyl ester (366 mg, 2.53 mmol). The reaction was heated at 100° C. for 5 hours. After cooling to room temperature, the precipitated solid was isolated by vacuum filtration and then repulped from diethyl ether to afford I-4A-1a (292 mg, 36%) as a colorless solid: +ESI MS (M+1) 384.1; $^1$H NMR (400 MHz, DMSO-$d_6$) δ 11.77 (s, 1H), 7.45–7.33 (m, 6H), 7.11 (d, J=8.7 Hz, 2H), 2.33 (s, 3H), 1.99 (s, 3H).

Preparation of Intermediate 7-Chloro-3-(4-chlorophenyl)-2-(2-chlorophenyl)-5,6-dimethylpyrazolo[1,5-a]pyrimidine (I-4A-1b)

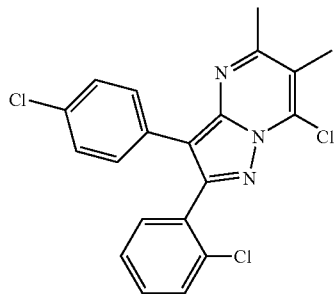

To a slurry of 3-(4-chlorophenyl)-2-(2-chlorophenyl)-5,6-dimethyl-pyrazolo[1,5-a]pyrimidin-7-ol (I-4A-1a; 0.277 g, 0.721 mmol) and diisopropylethylamine (0.188 ml, 1.08 mmol) in toluene (7.2 ml) at room temperature was added POCl$_3$ (0.336 ml, 3.60 mmol), dropwise. The mixture was heated at 100° C. for 7 hours, cooled to room temperature, and then slowly added to a stirred mixture of ice, saturated aqueous sodium bicarbonate and ethyl acetate. The aqueous layer was separated and extracted with additional ethyl acetate. The combined organic layers were washed with brine, dried (MgSO$_4$), and then concentrated, in vacuo, to afford the crude product. Purification on a Biotage™ Flash 40S column using 0–8% ethyl acetate in hexanes as eluant afforded I-4A-1b (146 mg, 50%) as a yellow solid: +ESI MS (M+1) 402.0; $^1$H NMR (400 MHz, CD$_2$Cl$_2$) δ 7.55–7.35 (m, 6H), 7.25 (d, J=8.7 Hz, 2H), 2.66 (s, 3H), 2.47 (s, 3H).

Preparation of Intermediate 2-Benzhydryl-5-methyl-2,5,7-triazaspiro[3.4]oct-6-en-8-one (I-5A-10a)

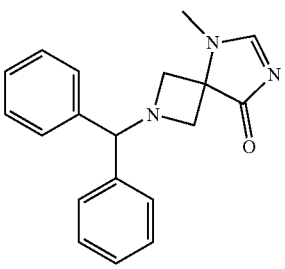

N,N-Dimethylformamide dimethyl acetal (1.1 ml, 8.3 mmol) was combined with 1-benzhydryl-3-methylaminoazetidine-3-carboxylic acid amide (I-3A-2b; 153 mg, 0.52 mmol) and heated to reflux. After 3 hours, the suspension was cooled and extracted from saturated aqueous NaHCO$_3$ with ethyl acetate. The combined extracts were dried (Na$_2$SO$_4$) and concentrated, in vacuo, to afford I-5A-10a as a solid (152 mg, 96%): +ESI MS (M+1) 306.3; $^1$H NMR (400 MHz, CD$_3$OD) δ 8.42 (s, 1H), 7.47 (d, J=7.5 Hz, 4H), 7.27 (t, J=7.5 Hz, 4H), 7.17 (t, J=7.5 Hz, 2H), 4.57 (s, 1H), 3.58 (s, 3H), 3.55 (d, J=10.0 Hz, 2H), 3.34 (d, J=10.0 Hz, 2H).

Preparation of Intermediate 5-Methyl-2,5,7-triazaspiro[3.4]octan-8-one, Hydrochloride Salt (I-5A-10b)

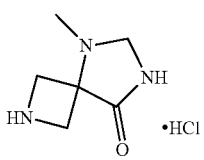

To a solution of 2-benzhydryl-5-methyl-2,5,7-triazaspiro[3.4]oct-6-en-8-one (I-5A-10a; 189 mg, 0.619 mmol) in methanol (30 ml) was added 1 M HCl in diethyl ether (1.3 ml). After the addition of 20% Pd(OH)$_2$ on carbon (50% water; 95 mg), the mixture was placed on a Parr® shaker and then reduced (50 psi H$_2$) at room temperature for 5 hours. The reaction was filtered through a 0.45 μM disk, and then concentrated, in vacuo, to give a solid. Trituration from diethyl ether afforded I-5A-10b (124 mg, 94%) as an off-white solid: +APcI MS (M+1) 142.0; $^1$H NMR (400 MHz, CD$_3$OD) δ 4.38 (d, J=12.0 Hz, 2H), 4.17 (s, 2H), 4.13 (d, J=12.5 Hz, 2H), 2.71 (s, 3H).

Preparation of Intermediate 2-(2-Chlorophenyl)-7-ethoxy-3-iodopyrazolo[1,5-a]pyrimidine (I-11A-1a)

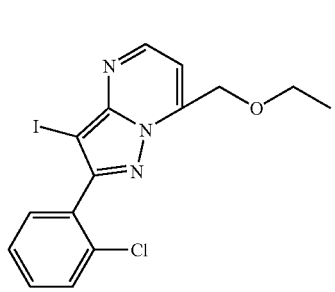

I-11A-1a

To a mixture of 7-chloro-2-(2-chlorophenyl)-3-iodopyrazolo[1,5-a]pyrimidine (I-1A-1d; 6.80 g, 17.4 mmol) in ethanol (175 ml) was added NaH (60% dispersion in oil, 439 mg, 18 mmol), portionwise. After stirring overnight, the suspended solids were isolated by vacuum filtration to afford, after drying, in vacuo, product I-11A-1a (6.87 g, 99%) as a solid: +APcI MS (M+1) 400.0; $^1$H NMR (400 MHz, CD$_3$OD) δ 8.51 (d, J=5.0 Hz, 1H), 7.58–7.40 (m, 4H), 6.67 (d, J=5.0 Hz, 1H), 4.58 (q, J=7.1 Hz, 2H), 1.58 (t, J=7.1 Hz, 3H).

Preparation of Intermediate 3-(4-Chlorophenyl)-2-(2-chlorophenyl)-pyrazolo[1,5-a]pyrimidin-7-ol (I-12A-1a)

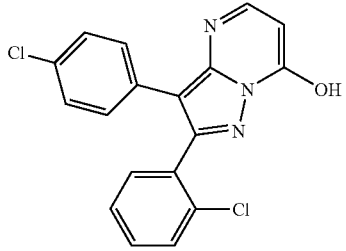

I-12A-1a

To a solution of 3-(4-chlorophenyl)-2-(2-chlorophenyl)-7-ethoxypyrazolo[1,5-a]pyrimidine (11A-1; 250 mg, 0.653 mmol) in THF (6.5 ml) was added water (1.5 ml) and 1M tetrabutylammonium hydroxide in water (3.3 ml, 3.3 mmol). The reaction was heated at 60° C. overnight, cooled, diluted with ethyl acetate and water, and then adjusted to pH 4.5 with 1M aqueous HCl. The aqueous layer was separated and extracted with ethyl acetate. The combined organic layers were washed with brine, dried (MgSO$_4$), and then concentrated to afford, after trituration from ethyl acetate, I-12A-1a as a tan solid (138 mg, 60%): +APcI MS (M+1) 354.1; $^1$H NMR (400 MHz, CD$_3$OD) δ 7.79 (d, J=7.1 Hz, 1H), 7.49–7.43 (m, 1H), 7.42–7.35 (m, 3H), 7.30 (d, J=8.7 Hz, 2H), 7.15 (d, J=8.7 Hz, 2H), 5.93 (d, J=7.1 Hz, 1H).

Preparation of 7-Chloro-3-(4-chlorophenyl)-2-(2-chlorophenyl)-pyrazolo[1,5-a]pyrimidine (I-13A-1a)

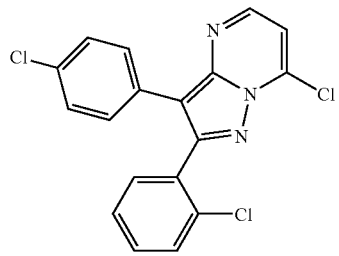

I-13A-1a

To a slurry of 3-(4-chlorophenyl)-2-(2-chlorophenyl)-pyrazolo[1,5-a]pyrimidin-7-ol (I-12A-1a; 2.00 g, 5.61 mmol) and diisopropylethylamine (4.0 ml, 22 mmol) in toluene (60 ml) at room temperature was added POCl$_3$ (2.1 ml, 22 mmol), dropwise. The mixture was heated at 100° C. for 7 hours, concentrated, in vacuo, and the purified by silica gel chromatography using 10% hexanes in methylene chloride as eluant to afford I-13A-1a (1.72 g, 82%) as a solid: +APcI MS (M+1) 374.1; $^1$H NMR (400 MHz, CD$_2$Cl$_2$) δ 8.49 (d, J=4.6 Hz, 1H), 7.54–7.38 (m, 6H), 7.28 (d, J=8.7 Hz, 2H), 7.12 (d, J=4.2 Hz, 1H).

Preparation of Intermediate 6-Ally-3-(4-chlorophenyl)-2-(2-chlorophenyl)-pyrazolo[1,5-a]pyrimidin-7-ol (I-15A-1a)

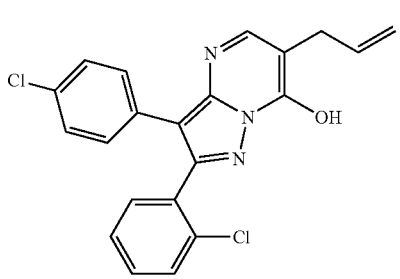

I-15A-1a

To a suspension of 7-chloro-3-(4-chlorophenyl)-2-(2-chlorophenyl)-pyrazolo[1,5-a]pyrimidine (I-13A-1a; 1.72 g, 4.6 mmol) in allyl alcohol (50 ml) at 0° C. was added NaH (60% dispersion in oil, 0.28 g, 6.9 mmol), portionwise over 3 minutes. After warming to room temperature, the reaction was stirred overnight. The resultant allyl ether was then heated at 125° C. for 1.5 hours to facilitate the rearrangement. The reaction was concentrated, in vacuo, to give a residue which was partitioned between ethyl acetate and water adjusted to pH=4 with 1M aqueous HCl. The organic layer which contained dispersed solids was separated, washed with brine, and the solids then collected by vacuum filtration to give product I-15A-1a (1.24 g, 68%) as a solid: +ESI MS (M+1) 396.4; $^1$H NMR (400 MHz, CD$_3$OD) δ 7.64 (s 1H), 7.52–7.48 (m, 1H), 7.43–7.48 (m, 3H), 7.30 (d, J=8.7 Hz, 2H), 7.15 (d, J=8.7 Hz, 2H), 6.06–5.92 (m, 1H), 5.21–5.14 (m, 1H), 5.12–5.07 (m, 1H).

Example 1

Preparation of Intermediate 1-[2-(2-Chlorophenyl)-3-iodopyrazolo[1,5-a]pyrimidin-7-yl]-4-ethylaminopiperidine-4-carboxylic Acid Amide (I-1A-1h)

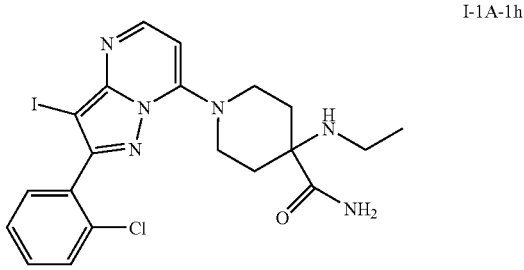

I-1A-1h

To a solution of 7-chloro-2-(2-chlorophenyl)-3-iodopyrazolo[1,5-a]pyrimidine (I-1A-1d; 80 mg, 0.21 mmol) and triethylamine (44 μl, 0.32 mmol) in 1:1 ethanol/methylene chloride (2 ml) was added 4-ethylaminopiperidine-4-carboxylic acid amide (I-1A-1g; 40 mg, 0.23 mmol). A colorless precipitate formed after several minutes and the mixture was stirred overnight. The solid precipitate was isolated by vacuum filtration, washed with ethanol and ether, and then dried, in vacuo, to afford product I-1A-1h as an off-white solid (95 mg, 86%): +APcI MS (M+1) 525.4; $^1$H NMR (400 MHz, CD$_3$OD) δ 8.27 (d, J=5.4 Hz, 1H), 7.55 (d, J=7.5 Hz, 1H), 7.48–7.39 (m, 3H), 6.45 (d, J=5.6 Hz, 1H), 4.14–3.96 (m, 2H), 3.92–3.84 (m, 2H), 2.50 (q, J=7.1 Hz, 2H), 2.23–2.15 (m, 2H), 1.85–1.77 (m, 2H), 1.16 (t, J=7.1 Hz, 3H).

Preparation of 1-[3-(4-Chlorophenyl)-2-(2-chlorophenyl)-pyrazolo[1,5-a]pyrimidin-7-yl]-4-ethylaminopiperidine-4-carboxylic Acid Amide (1A-1)

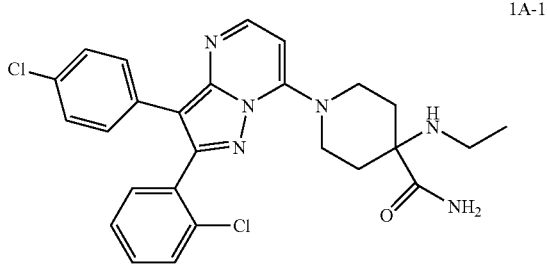

1A-1

A mixture of 1-[2-(2-chlorophenyl)-3-iodopyrazolo[1,5-a]pyrimidin-7-yl]-4-ethylaminopiperidine-4-carboxylic acid amide (I-1A-1h; 90 mg, 0.17 mmol) and 4-chlorophenylboronic acid (41 mg, 0.26 mmol) in ethanol (2 ml), toluene (2 ml) and 2M aqueous Na$_2$CO$_3$ (1 ml) was degassed (3×) by pulling a vacuum followed by refilling with nitrogen gas. Tetrakis(triphenylphosphine)palladium (27 mg, 0.023 mmol) was added and the mixture was heated to 80° C. for 1 hr. After cooling to room temperature, the mixture was extracted from water with ethyl acetate, the combined organic layers were washed with brine, dried (MgSO$_4$), filtered through a 0.45 μm filter disk, and then concentrated, in vacuo, to afford the crude product (190 mg). Purification on a Chromatotron using 0–5% methanol in methylene chloride as eluant afforded compound 1A-1 (62 mg, 72%): +ESI MS (M+1) 509.4; $^1$H NMR (400 MHz, CD$_3$OD) δ 8.28 (d, J=5.4 Hz, 1H), 7.48–7.35 (m, 6H), 7.22 (d, J=8.7 Hz, 2H), 6.46 (d, J=5.0 Hz, 1H), 4.04–3.96 (m, 2H), 3.92–3.84 (m, 2H), 2.53 (q, 7.0 Hz, 2H), 2.27–2.19 (m, 2H), 1.88–1.81 (m, 2H), 1.12 (t, J=7.0 Hz, 3H).

The Hydrochloride Salt of Compound 1A-1 may be Prepared Using the Following Procedure:

To a solution of 1-[3-(4-chlorophenyl)-2-(2-chlorophenyl)-pyrazolo[1,5-a]pyrimidin-7-yl]-4-ethylaminopiperidine-4-carboxylic acid amide (1A-1; 62 mg, 0.12 mmol) in methanol (2 ml) was added 1M HCl in diethyl ether (0.30 ml). After stirring for 5 minutes, the reaction was concentrated, in vacuo, and then triturated from ethanol (4 drops) and excess diethyl ether. The solid precipitate was isolated by vacuum filtration, washed with ether and then dried, in vacuo, to afford the hydrochloride salt of 1A-1 as a light yellow solid (46 mg, 66%): +ESI MS (M+1) 509.3; $^1$H NMR (400 MHz, CD$_3$OD) δ 8.83 (d, J=6.6 Hz, 1H), 7.49–7.44 (m, 3H), 7.41–7.35 (m, 3H), 7.26 (d, J=8.7 Hz, 2H), 6.76 (d, J=6.6 Hz, 1H), 4.82–4.73 (br m, 2H), 4.04 (br t, J=11.8 Hz, 2H), 3.07 (q, J=7.2 Hz, 2H), 2.71 (br d, J=15.8 Hz, 2H), 2.74–2.25 (br m, 2H), 1.36 (t, J=7.3 Hz, 3H).

The compounds listed in Table 1 below were prepared using procedures analogous to those described above for the synthesis of Compound 1A-1 using the appropriate starting materials which are available commercially, prepared using preparations well-known to those skilled in the art, or prepared in a manner analogous to routes described above for other intermediates. The compounds listed below were isolated initially as the free base and then generally converted to their corresponding hydrochloride salt for testing.

TABLE 1

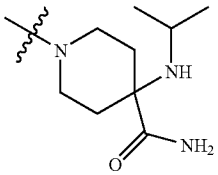

| Example No. | R$^2$ | R$^3$ | —NRR' | MS (M + H) + |
|---|---|---|---|---|
| 1A-2 | H | H | (4-isopropylamino-piperidine-4-carboxamide) | 523.3 |
| 1A-3 | Me | H | (3-ethylamino-azetidine-3-carboxamide) | 495.0 |

Example 2

Preparation of Intermediate 1-[2-(2-Chlorophenyl)-3-iodopyrazolo[1,5-a]pyrimidin-7-yl]-3-ethylaminoazetidine-3-carboxylic Acid Amide (I-2A-1a)

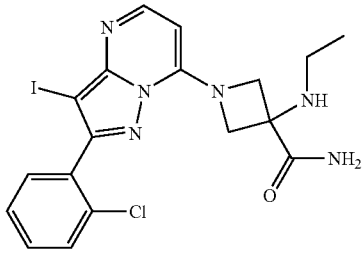

I-2A-1a

To a slurry of 3-ethylaminoazetidine-3-carboxylic acid amide, hydrochloride salt (I-1A-3e; 1.13 g, 5.2 mmol) and diisopropylethylamine (3.2 ml, 18 mmol) in acetone (60 ml) was added 7-chloro-2-(2-chlorophenyl)-3-iodopyrazolo[1,5-a]pyrimidine (I-1A-1d; 1.36 g, 3.48 mmol). The mixture was heated to 50° C. overnight. Additional azetidine and diisopropylethylamine were added in portions until the reaction was judged complete by LCMS. A pale yellow precipitate formed and was isolated by vacuum filtration. The filtrate was concentrated to 20 ml and then diluted with diethyl ether to precipitate additional material that was collected by vacuum filtration. The combined solids were triturated from ether to afford product I-2A-1a as a pale yellow solid (1.3 g, 76%): +ESI MS (M+1) 497.0; $^1$H NMR (400 MHz, DMSO-D$_6$) δ 8.27 (d, J=5.4 Hz, 1H), 7.59 (d, J=7.9 Hz, 1H), 7.52–7.44 (m, 3H), 7.35 (br s, 1H), 7.30 (br s, 1H), 5.98 (d, J=5.0 Hz, 1H), 2.40–2.30 (m, 2H), 0.99 (t, J=7.1 Hz, 3H).

Preparation of 1-[3-(4-Chlorophenyl)-2-(2-chlorophenyl)-pyrazolo[1,5-a]pyrimidin-7-yl]-3-ethylaminoazetidine-3-carboxylic Acid Amide (2A-1)

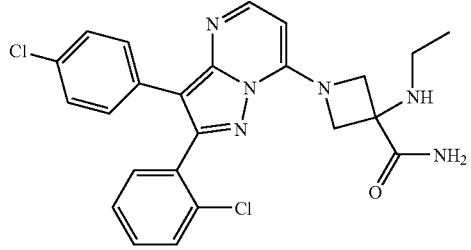

2A-1

A mixture of 1-[2-(2-chlorophenyl)-3-iodopyrazolo[1,5-a]pyrimidin-7-yl]-3-ethylaminoazetidine-3-carboxylic acid amide (I-2A-1a; 1.10 g, 2.22 mmol), 4-chlorophenylboronic acid (0.382 g, 2.44 mmol) and tetrakis(triphenylphosphine) palladium (384 mg, 0.33 mmol) in ethanol (25 ml), toluene (25 ml), and 2M aqueous Na$_2$CO$_3$ (12.5 ml) was heated to 80° C. for 3 hours. After cooling to room temperature, the mixture was extracted from water with ethyl acetate, the combined organic layers were washed with brine, dried (MgSO$_4$), and then concentrated, in vacuo, to afford the crude product. Flash chromatography using 40:1 methylene chloride/methanol as eluant afforded a yellow solid. Trituration of the solid from diethyl ether/methanol afforded 2A-1 (0.49 g, 46%) as an off-white solid: +ESI MS (M+1) 481.1; $^1$H NMR (400 MHz, DMSO-D$_6$) δ 8.19 (d, J=5.0 Hz, 1H), 7.50–7.30 (m, 6H), 7.21 (d, J=8.7 Hz, 2H), 6.99 (br d, J=3.3 Hz, 1H), 5.77 (d, J=5.4 Hz, 1H), 5.59 (br d, J=3.7 Hz, 1H), 4.88 (br d, J=7.9 Hz, 2H), 4.36 (br s, 2H), 2.61 (q, J=7.2 Hz, 2H), 1.14 (t, J=7.1 Hz, 3H).

The Hydrochloride Salt of Compound 2A-1 may be Prepared Using the Following Procedure:

To a suspension of 1-[3-(4-chlorophenyl)-2-(2-chlorophenyl)-pyrazolo[1,5-a]pyrimidin-7-yl]-3-ethylaminoazetidine-3-carboxylic acid amide in methanol was added excess 2M HCl in diethyl ether. After stirring for 5 minutes, the reaction was concentrated, in vacuo, to give a yellow solid. A portion of the solid (46 mg) was stirred in 95:5 isopropyl alcohol/water (1 ml) for 1 hour. The mother liquor was removed by pipette, and the process repeated a second time. The solid was then stirred in MTBE (1 ml) for an additional hour before the solvent was removed by pipette. The isolated solid was then dried, in vacuo, to afford the hydrochloride salt of 2A-1 as an off-white solid (30 mg, 65%): +ESI MS (M+1) 481.1; $^1$H NMR (400 MHz, CD$_3$OD) δ 8.26 (d, J=6.6 Hz, 1H), 7.50–7.20 (m, 8H), 6.32 (d, J=6.6 Hz, 1H), 5.35–5.13 (br m, 4H), 3.19 (q, J=7.1 Hz, 2H), 1.39 (t, J=7.1 Hz, 3H).

Example 3

Preparation of 1-[3-(4-Chlorophenyl)-2-(2-chlorophenyl)-6-methylpyrazolo[1,5-a]pyrimidin-7-yl]-4-ethylaminopiperidine-4-carboxylic Acid Amide (3A-1)

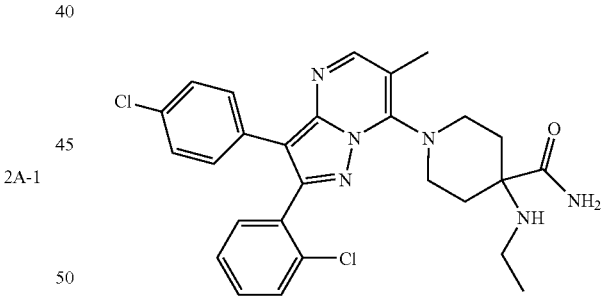

3A-1

To a solution of 7-chloro-3-(4-chlorophenyl)-2-(2-chlorophenyl)-6-methylpyrazolo[1,5-a]pyrimidine (I-3A-1d; 31.3 mg, 0.0806 mmol) and diisopropylethylamine (0.025 ml, 0.14 mmol) in THF (1 ml) was added 4-ethylaminopiperidine-4-carboxylic acid amide (I-1A-1g; 18.5 mg, 0.108 mmol). The mixture was stirred at 50° C. for 20 hours. After cooling to room temperature, the reaction was extracted from saturated aqueous NaHCO$_3$ with ethyl acetate, the combined organic layers were dried (MgSO$_4$), concentrated and purified on a Biotage™ Flash 12S column using 0–5% methanol in methylene chloride as eluant to afford, after trituration from hexanes/methylene chloride, product 3A-1 as a solid (29 mg, 69%): +ESI MS (M+1) 523.4; $^1$H NMR (400 MHz, CD$_3$OD) δ 8.24 (s, 1H), 7.48–7.34 (m, 6H), 7.21 (d, J=8.7 Hz, 2H), 3.82–3.74 (m, 2H), 3.66–3.58 (m, 2H), 2.51 (q, J=7.1 Hz, 2H), 2.39 (s, 3H), 2.28–2.20 (m, 2H), 1.88–1.80 (m, 2H), 1.10 (t, J=7.1 Hz, 3H).

Preparation of 3-[3-(4-Chlorophenyl)-2-(2-chlorophenyl)-5-methylpyrazolo[1,5-a]pyrimidin-7-yl]-6-morpholin-4-yl-3-(1α,5α,6α)-azabicyclo[3.1.0]hexane-6-carbonitrile (3A-2):

3A-2

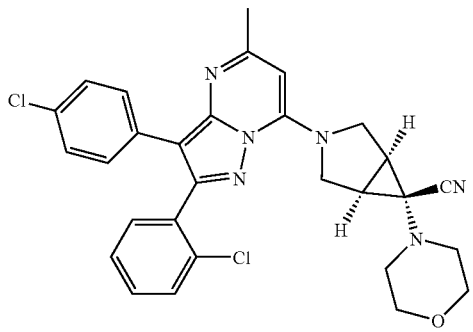

3-[3-(4-Chlorophenyl)-2-(2-chlorophenyl)-5-methylpyrazolo[1,5-a]pyrimidin-7-yl]-6-morpholin-4-yl-3-(1α,5α,6α)-azabicyclo[3.1.0]hexane-6-carbonitrile was prepared using procedures analogous to those described above for the synthesis of Compound 3A-1. The final coupling step was conducted in 9:1 acetone/water: +ESI MS (M+1) 545.5; $^1$H NMR (400 MHz, CD$_2$Cl$_2$) δ 7.48–7.32 (m, 6H), 7.21 (d, J=8.7 Hz, 2H), 5.75 (s, 1H), 4.48 (d, J=11.6 Hz, 2H), 4.26–4.18 (m, 2H), 3.65 (t, J=4.8 Hz, 4H), 2.69 (t, J=4.8 Hz, 4H), 2.47 (s, 3H), 2.33–2.28 (m, 2H).

Example 4

Preparation of 1-[3-(4-Chlorophenyl)-2-(2-chlorophenyl)-5,6-dimethylpyrazolo[1,5-a]pyrimidin-7-yl]-3-ethylaminoazetidine-3-carboxylic Acid Amide (4A-1)

4A-1

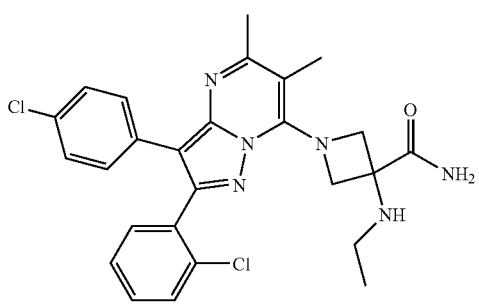

To a solution of 7-chloro-3-(4-chlorophenyl)-2-(2-chlorophenyl)-5,6-dimethylpyrazolo[1,5-a]pyrimidine (I-4A-1b; 44.7 mg, 0.111 mmol) and diisopropylethylamine (0.058 ml, 0.33 mmol) in THF (0.6 ml) and methanol (0.1 ml) was added 3-ethylaminoazetidine-3-carboxylic acid amide, hydrochloride salt (I-1A-3e; 28.7 mg, 0.133 mmol). The mixture was stirred at 55° C. for 23 hours. After cooling to room temperature, the reaction was extracted from saturated aqueous NaHCO$_3$, the combined organic layers were dried (MgSO$_4$), concentrated and purified on a Biotage™ Flash 12S column using 0–3% methanol in methylene chloride as eluant to afford product 4A-1 (34.7 mg, 61%) as a solid: +ESI MS (M+1) 509.0; $^1$H NMR (400 MHz, CD$_3$OD) δ 7.44–7.30 (m, 6H), 7.18 (d, J=8.7 Hz, 2H), 5.15 (d, J=9.6 Hz, 2H), 4.78 (d, J=9.6 Hz, 2H), 2.54 (q, J=7.1 Hz, 2H), 2.46 (s, 3H), 2.32 (s, 3H), 1.13 (t, J=7.1 Hz, 3H).

The Hydrochloride Salt of Compound 4A-1 may be Prepared Using the Following Procedure:

To a solution of 1-[3-(4-chlorophenyl)-2-(2-chlorophenyl)-5,6-dimethylpyrazolo[1,5-a]pyrimidin-7-yl]-3-ethylaminoazetidine-3-carboxylic acid amide (4A-1; 35 mg, 0.068 mmol) in methylene chloride (0.6 ml) and methanol (0.1 ml) was added 1M HCl in diethyl ether (0.076 ml). After stirring for 20 minutes, the reaction was concentrated, in vacuo, then triturated from diisopropyl ether to afford the hydrochloride salt of 4A-1 (38 mg, quantitative) as an off-white solid: $^1$H NMR (400 MHz, CD$_3$OD) δ 7.48–7.24 (m, 8H), 5.44 (d, J=12.0 Hz, 2H), 5.25 (br d, J=11.6 Hz, 2H), 3.4–3.0 (br m, 2H), 2.54 (s, 3H), 2.37 (s, 3H), 1.34 (br t, 2H), The compounds listed in Table 2 below were prepared using procedures analogous to those described above for the synthesis of Compound 4A-1 using the appropriate starting materials which are available commercially, prepared using preparations well-known to those skilled in the art, or prepared in a manner analogous to routes described above for other intermediates. The compounds listed below were isolated initially as the free base and then generally converted to their corresponding hydrochloride salt for testing. The final coupling step for Compound 4A-4 was conducted in 9:1 acetone/water.

TABLE 2

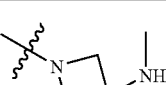

| Example No. | R$^2$ | R$^3$ | —NRR' | MS (M + H) + |
|---|---|---|---|---|
| 4A-2 | H | Me | 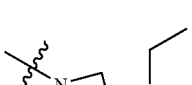 | 481.3 |
| 4A-3 | H | Me |  | 495.3 |

TABLE 2-continued

| Example No. | R² | R³ | —NRR' | MS (M + H) + |
|---|---|---|---|---|
| 4A-4 | Me | H | (azetidin-3-yl with C(O)NH₂ and NH-Me) | 481.2 |

Example 5

Preparation of 4-[3-(4-Chlorophenyl)-2-(2-chlorophenyl)-5-methylpyrazolo[1,5-a]pyrimidin-7-yl]-piperazine-1-carboxylic Acid tert-Butyl Ester (5A-1)

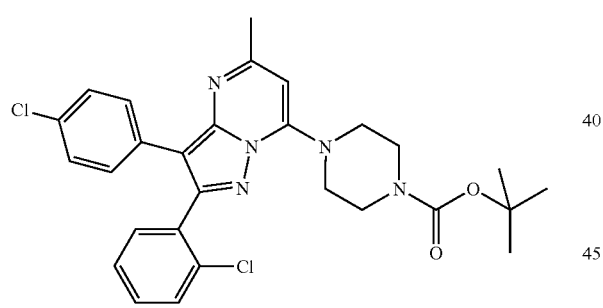

5A-1

To a solution of 7-chloro-3-(4-chlorophenyl)-2-(2-chlorophenyl)-5-methylpyrazolo[1,5-a]pyrimidine (I-3A-4b; 109 mg, 0.280 mmol) and Argonaut™ PS-DIEA (97 mg, 0.38 mmol) in 1,2-dichloroethane (2.8 ml) was added piperazine-1-carboxylic acid tert-butyl ester (70.5 mg, 0.378 mmol). The mixture was stirred at room temperature for 19 hours, filtered, concentrated and then purified on a Biotage™ Flash 12M column using 0–35% ethyl acetate in hexanes as eluant to afford, after trituration from hexanes/methylene chloride, product 5A-1 (132 mg, 88%) as an off-white solid: +ESI MS (M+1) 538.4; ¹H NMR (400 MHz, CD₂Cl₂) δ 7.48–7.32 (m, 6H), 7.22 (d, J=8.7 Hz, 2H), 6.13 (s, 1H), 3.73–3.61 (m, 8H), 2.56 (s, 3H), 1.45 (s, 9H).

The compounds listed in Table 3 below were prepared using procedures analogous to those described above for the synthesis of Compound 5A-1 using the appropriate starting materials which are available commercially, prepared using preparations well-known to those skilled in the art, or prepared in a manner analogous to routes described above for other intermediates. The final coupling step for Compounds 5A-3 through 5A-14 was conducted at 40° C.

TABLE 3

| Example No. | —NRR' | MS (M + H) + |
|---|---|---|
| 5A-2 | (bicyclic diamine with N-Boc) | 550.4 |
| 5A-3 | NH-n-butyl | 425.4 |
| 5A-4 | NH-CH₂CH₂OCH₃ | 427.3 |
| 5A-5 | NH-CH₂CH₂-(4-fluorophenyl) | 491.3 |
| 5A-6 | NH-CH₂CH₂-morpholine | 482.1 |
| 5A-7 | piperazine-N-(pyrimidin-2-yl) | 516.4 |
| 5A-8 | 4-methylpiperazine | 452.0 |
| 5A-9 | piperidine-spiro-imidazolidinone with N-isopropyl | 549.1 |

TABLE 3-continued

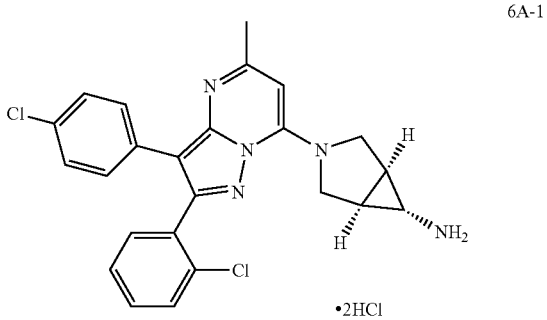

| Example No. | —NRR' | MS (M + H) + |
|---|---|---|
| 5A-10 | (azetidine-spiro-imidazolidinone) | 493.0 |
| 5A-11 | (4-acetyl-4-phenylpiperidine) | 555.3 |
| 5A-12 | (4-(4-fluorophenyl)-4-hydroxypiperidine) | 547.4 |
| 5A-13 | (3-(tert-butoxycarbonylamino)-azabicyclo[3.1.0]hexane) | 550.4 |
| 5A-14 | (4-benzyl-4-hydroxypiperidine) | 543.4 |

Example 6

Preparation of 3-[3-(4-Chlorophenyl)-2-(2-chlorophenyl)-5-methylpyrazolo[1,5-a]pyrimidin-7-yl]-3-(1α,5α,6α)-azabicyclo[3.1.0]hex-6-ylamine. Hydrochloride Salt (6A-1)

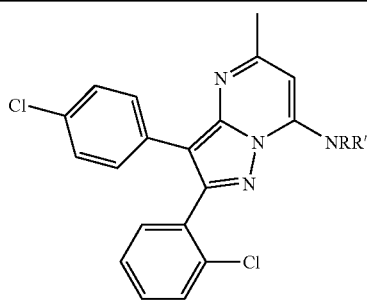

6A-1
·2HCl

To a solution of {3-[3-(4-chlorophenyl)-2-(2-chlorophenyl)-5-methylpyrazolo[1,5-a]pyrimidin-7-yl]-3-(1α,5α,6α)-azabicyclo[3.1.0]hex-6-yl}-carbamic acid tert-butyl ester (5A-13; 25 mg, 0.045 mmol) in methylene chloride (1 ml) was added 4M HCl in dioxane (0.11 ml, 45 mmol). After stirring 6 hours, the reaction was concentrated, in vacuo, and then triturated from diethyl ether to afford 6A-1 (24 mg, quantitative) as an off-white solid: +ESI MS (M+1) 450.3; $^1$H NMR (400 MHz, CD$_3$OD) δ 7.46–7.34 (m, 6H), 7.20 (d, J=8.3 Hz, 2H), 6.32 (s, 1H), 4.44–4.30 (br m, 2H), 2.67 (s, 1H), 2.56 (s, 3H), 2.35 (s, 2H).

The compounds listed in Table 4 below were prepared using procedures analogous to those described above for the synthesis of Compound 6A-1 using the appropriate starting materials which are available commercially, prepared using preparations well-known to those skilled in the art, or prepared in a manner analogous to routes described above for other intermediates.

TABLE 4

| Example No. | —NRR' | MS (M + H) + |
|---|---|---|
| 6A-2 | (diazabicyclic amine) | 450.4 |

TABLE 4-continued

| Example No. | —NRR' | MS (M + H) + |
|---|---|---|
| 6A-3 | (piperazin-1-yl) | 438.4 |

Example 7

Preparation of 1-{4-[3-(4-Chlorophenyl)-2-(2-chlorophenyl)-5-methylpyrazolo[1,5-a]pyrimidin-7-yl]-piperazin-1-yl}-ethanone (7A-1)

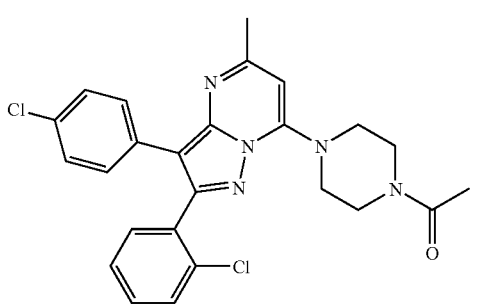

To a mixture of 3-(4-chlorophenyl)-2-(2-chlorophenyl)-5-methyl-7-piperazin-1-yl-pyrazolo[1,5-a]pyrimidine, hydrochloride salt (6A-3; 25 mg, 0.049 mmol), Argonaut™ PS-DIEA (63 mg, 0.24 mmol) and diisopropylethylamine (0.020 ml, 0.11 mmol) in methylene chloride (1 ml), was added acetyl chloride (0.005 ml, 0.074 mmol). After stirring 20 minutes, the reaction was filtered, concentrated and then purified on a Biotage™ Flash 12S column using 0–50% ethyl acetate in hexanes as eluant to afford, after trituration from hexanes/methylene chloride, 7A-1 (19 mg, 79%) as a solid: +ESI MS (M+1) 480.3; $^1$H NMR (400 MHz, CD$_3$OD) δ 7.49–7.34 (m, 6H), 7.23 (d, J=8.7 Hz, 2H), 6.14 (s, 1H), 3.84–3.78 (m, 4H), 3.71–3.61 (m, 4H), 2.57 (s, 3H), 2.10 (s, 3H).

The compounds listed in Table 5 below were prepared using procedures analogous to those described above for the synthesis of Compound 7A-1 using the appropriate starting materials which are available commercially, prepared using preparations well-known to those skilled in the art, or prepared in a manner analogous to routes described above for other intermediates. Compounds 7A-2, 7A-3 and 7A-4 were isolated initially as the free base and then converted to their corresponding hydrochloride salt for testing.

TABLE 5

| Example No. | —NRR' | MS (M + H) + |
|---|---|---|
| 7A-2 | piperazinyl-N-SO$_2$CH$_3$ | 516.3 |
| 7A-3 | piperazinyl-N-SO$_2$CH$_2$CH$_3$ | 530.3 |
| 7A-4 | piperazinyl-N-SO$_2$CH(CH$_3$)$_2$ | 544.3 |
| 7A-5 | bicyclic diamine-SO$_2$CH(CH$_3$)$_2$ | 556.3 |
| 7A-6 | bicyclic diamine-C(O)CH$_3$ | 492.3 |

Example 8

Preparation of 3-(4-Chlorophenyl)-2-(2-chlorophenyl)-7-isopropoxy-5-methylpyrazolo[1,5-a]pyrimidine (8A-1)

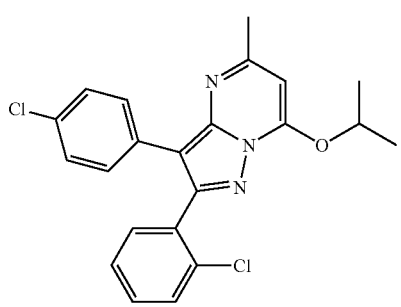

8A-1

To a solution of 7-chloro-3-(4-chlorophenyl)-2-(2-chlorophenyl)-5-methylpyrazolo[1,5-a]pyrimidine (I-3A-4b; 59 mg, 0.15 mmol) in THF (0.5 ml) and isopropanol (0.5 ml) was added NaH (60% dispersion in oil, 30 mg, 0.76 mmol). After stirring for 1 hour, the reaction was extracted from saturated aqueous NaHCO$_3$ with ethyl acetate, the combined organic layers were dried (MgSO$_4$), concentrated and purified on a Biotage™ Flash 12M column using 0–35% ethyl acetate in hexanes as eluant to afford 8A-1 (59 mg, 95%) as a colorless solid: +ESI MS (M+1) 412.4; $^1$H NMR (400 MHz, CD$_2$Cl$_2$) δ 7.50–7.36 (m, 6H), 7.23 (d, J=8.7 Hz, 2H), 6.19 (s, 1H), 4.99 (septuplet, J=6.1 Hz, 1H), 2.62 (s, 3H), 1.57 (d, J=5.8 Hz, 6H).

Example 9

Preparation of 7-(1-tert-Butylazetidin-3-yloxy)-3-(4-chlorophenyl)-2-(2-chlorophenyl)-5-methylpyrazolo[1,5-a]pyrimidine (9A-1)

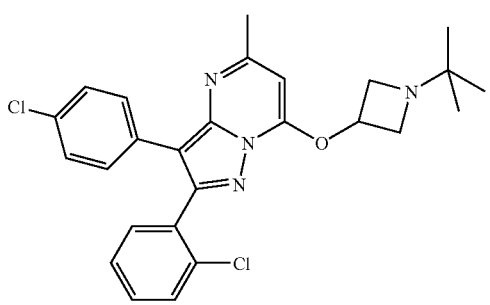

9A-1

To a solution of 1-tert-butylazetidin-3-ol (24 mg, 0.19 mmol) and 7-chloro-3-(4-chlorophenyl)-2-(2-chlorophenyl)-5-methylpyrazolo[1,5-a]pyrimidine (I-3A-4b; 36 mg, 0.093 mmol) in THF (1 ml) was added NaH (60% dispersion in oil, 9.3 mg, 0.23 mmol). After stirring for 1 hour, the reaction was quenched with water, extracted from saturated aqueous NaHCO$_3$ with ethyl acetate, the combined organic layers were dried (MgSO$_4$), concentrated and purified on a Biotage™ Flash 12M column using 0–5% methanol in methylene chloride as eluant to afford 9A-1 (26 mg, 59%) as a colorless solid: +ESI MS (M+1) 481.4; $^1$H NMR (400 MHz, CD$_2$Cl$_2$) δ 7.50–7.36 (m, 6H), 7.24 (d, J=8.7 Hz, 2H), 5.99 (s, 1H), 5.10–5.02 (m, 1H), 3.76–3.70 (br m, 2H), 3.49–3.43 (br m, 2H), 2.60 (s, 3H), 1.00 (s, 9H).

The compounds listed in Table 6 below were prepared using procedures analogous to those described above for the synthesis of Compound 9A-1 using the appropriate starting materials which are available commercially, prepared using preparations well-known to those skilled in the art, or prepared in a manner analogous to routes described above for other intermediates.

TABLE 6

| Example No. | —OR | MS (M + H) + |
|---|---|---|
| 9A-2 | ![structure] 3-(N-benzyl)pyrrolidinyloxy | 529.4 |
| 9A-3 | ![structure] 3-(N-cyclohexyl)azetidinyloxy | 507.4 |

Example 10

Preparation of 3-[3-(4-Chlorophenyl)-2-(2-chlorophenyl)-5-methylpyrazolo[1,5-a]pyrimidin-7-yl]-6-morpholin-4-yl-3-(1α,5α,6α)-azabicyclo[3.1.0]hexane-6-carboxylic Acid Amide (10A-1)

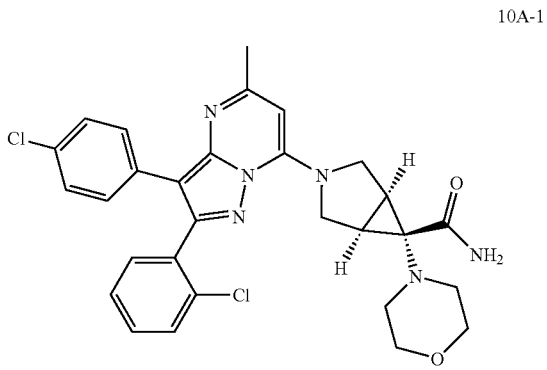

10A-1

3-[3-(4-Chlorophenyl)-2-(2-chlorophenyl)-5-methylpyrazolo[1,5-a]pyrimidin-7-yl]-6-morpholin-4-yl-3-(1α,5α,6α)-azabicyclo[3.1.0]hexane-6-carbonitrile (3A-2; 25 mg, 0.046 mmol) was heated at 100° C. in H₂SO₄ (0.6 ml) for 2 hours. The reaction mixture was cooled in an ice bath and then carefully quenched with aqueous 5N NaOH to pH 11. The mixture was extracted with ethyl acetate, the combined organic layers were dried (MgSO₄) and then concentrated, in vacuo, to afford, after trituration from methylene chloride/hexanes, product 10A-1 (21 mg, 80%) as a solid: +ESI MS (M+1) 563.4; ¹H NMR (400 MHz, CD₂Cl₂) δ0 7.48–7.32 (m, 6H), 7.20 (d, J=8.3 Hz, 2H), 5.74 (s, 1H), 5.60 (br s, 1H), 5.48 (br s, 1H), 4.69 (d, J=11.2 Hz, 2H), 3.83 (dd, J=9.6, 2.5 Hz, 2H), 3.60 (t, J=4.4 Hz, 4H), 2.66 (t, J=4.4 Hz, 4H), 2.45 (s, 3H), 2.01–2.00 (m, 2H).

Example 11

Preparation of 3-(4-Chlorophenyl)-2-(2-chlorophenyl)-7-ethoxypyrazolo[1,5-a]pyrimidine (11A-1)

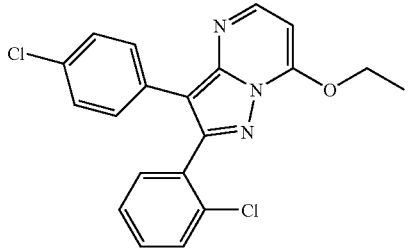

11A-1

To a mixture of 2-(2-chlorophenyl)-7-ethoxy-3-iodopyrazolo[1,5-a]pyrimidine (1–11A-1a; 6.76 g, 16.9 mmol), 4-chlorophenylboronic acid (4.07 g, 26.0 mmol), powdered K₂CO₃ (4.7 g, 34 mmol) and (1,1'-bis(diphenylphosphino)ferrocene)dichloropalladium(II), dichloromethane complex (0.69 g, 0.85 mmol) was added degassed dimethoxyethane (136 ml) and water (34 ml). The reaction was heated at 87° C. for 1.5 hours, cooled, and then concentrated under reduced pressure. The residue was dissolved in ethyl acetate and washed with 1 M aqueous NaOH, 1 M aqueous HCl, and brine. Suspended solids were collected by filtration (3.0 g). The solvent was removed, in vacuo, and the residue was triturated from ethanol to give additional solids (1.9 g). The combined solids were purified by silica gel chromatography using 9:1 methylene chloride/ hexanes as eluant to afford 11A-1 (4.45 g, 68%) as an off-white solid: +ESI MS (M+1) 384.3; ¹H NMR (400 MHz, CD₃OD) δ 8.51 (d, J=5.0 Hz, 1H), 7.53–7.40 (m, 6H), 7.24 (d, J=8.7 Hz, 2H), 6.66 (d, J=5.0 Hz, 1H), 4.59 (q, J=7.1 Hz, 2H), 1.60 (t, J=7.1 Hz, 3H).

Example 12

Preparation of 3-(4-Chlorophenyl)-2-(2-chlorophenyl)-7-(2,2,2-trifluoroethoxy)-pyrazolo[1,5-a]pyrimidine (12A-1)

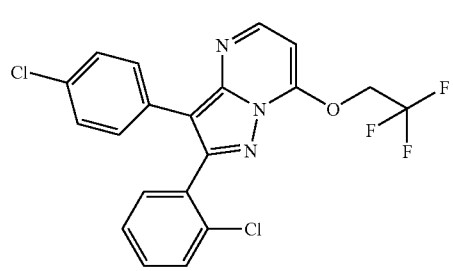

12A-1

To a mixture of 3-(4-chlorophenyl)-2-(2-chlorophenyl)-pyrazolo[1,5-a]pyrimidin-7-ol (I-12A-1a; 65 mg, 0.18 mmol) and Cs₂CO₃ (59 mg, 0.18 mmol) in DMF (1.5 ml) was added a DMF solution (0.1 ml) of trifluoromethanesulfonic acid 2,2,2-trifluoroethyl ester (42 mg, 0.18 mmol). After stirring at 60° C. overnight, the mixture was extracted from pH 7 water with ethyl acetate. The combined organic layers were washed with brine, dried (MgSO₄) and then concentrated, in vacuo, to afford the crude product. Purification on a Chromatotron using 1:0:0, 20:1:0, and then 20:0:1 methylene chloride/ethyl acetate/methanol as eluants afforded, in addition to two N-alkylated isomers, product 12A-1 (16.5 mg, 21%) as a solid: +ESI MS (M+1) 438.4; ¹H NMR (400 MHz, CD₃OD) δ 8.56 (d, J=5.0 Hz, 1H), 7.55–7.41 (m, 6H), 7.24 (d, J=8.7 Hz, 2H), 6.80 (d, J=5.0 Hz, 1H), 5.16 (q, J=7.9 Hz, 2H).

Example 13

Preparation of 7-Allyloxy-3-(4-chlorophenyl)-2-(2-chlorophenyl)-pyrazolo[1,5-a]pyrimidine (13A-1)

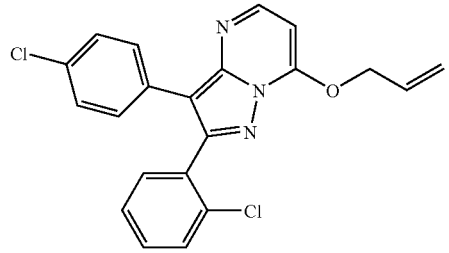

13A-1

To a suspension of 7-chloro-3-(4-chlorophenyl)-2-(2-chlorophenyl)-pyrazolo[1,5-a]pyrimidine (I-13A-1a; 30 mg, 0.08 mmol) in allyl alcohol (0.8 ml) was added NaH (60% dispersion in oil, 2 mg, 0.08 mmol). After stirring overnight, the reaction was concentrated and purified on a Chromatotron using methylene chloride as eluant to give product 13A-1 (12 mg, 38%) as a solid: +ESI MS (M+1) 396.4; ¹H NMR (400 MHz, CD₃OD) δ 8.51 (d, J=5.4 Hz, 1H), 7.53–7.40 (m, 6H), 7.24 (d, J=8.7 Hz, 2H), 6.68 (d, J=5.4 Hz, 1H), 6.20 (ddt, J=17.0, 10.4, 5.8 Hz, 1H), 5.64–5.58 (m, 1H), 5.45–5.41 (m, 1H), 5.10–5.08 (m, 2H).

Example 14

Preparation of 3,7-Bis-(4-chlorophenyl)-2-(2-chlorophenyl)-pyrazolo[1,5-a]pyrimidine (14A-1)

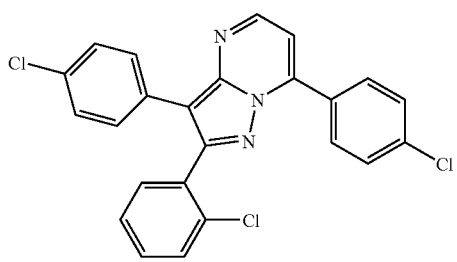

14A-1

A mixture of 7-chloro-2-(2-chlorophenyl)-3-iodopyrazolo[1,5-a]pyrimidine (I-1A-1d; 50 mg, 0.13 mmol), 4-chlorophenylboronic acid (30 mg, 0.19 mmol), $Na_2CO_3$ (108 mg, 0.67 mmol), and tetrakis(triphenylphosphine)palladium (15 mg, 0.013 mmol) in ethanol (1 ml) and water (0.23 ml) was degassed (3×) by pulling a vacuum followed by refilling with nitrogen gas. The reaction was heated at 72° C. for 2 hr, cooled to room temperature, and then extracted from water with ethyl acetate. The combined organic layers were washed with brine, dried ($MgSO_4$), and then concentrated, in vacuo. Purification on a Chromatotron using 20% ethyl acetate in hexanes as eluant afforded compound 14A-1 (17 mg, 30%) as a solid: +ESI MS (M+1) 450.3; $^1$H NMR (400 MHz, $CD_2Cl_2$) δ 8.62 (d, J=4.1 Hz, 1H), 8.01 (d, J=8.7 Hz, 2H), 7.56 (d, J=8.7 Hz, 2H), 7.51–7.36 (m, 6H), 7.28 (d, J=8.7 Hz, 2H), 7.04 (d, J=4.1 Hz, 1H).

Example 15

Preparation of 2-(2-Chlorophenyl)-3-(4-chlorophenyl)-7-iodomethyl-6,7-dihydro-8-oxa-1,4,8b-triaza-as-indacene (15A-1)

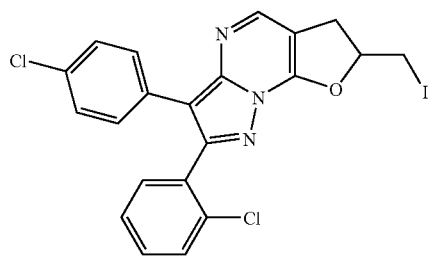

15A-1

To a mixture of 6-allyl-3-(4-chlorophenyl)-2-(2-chlorophenyl)-pyrazolo[1,5-a]pyrimidin-7-ol (I-15A-1a; 25 mg, 0.063 mmol) in 9:1 methylene chloride/chloroform (0.63 ml) at 0° C. was added N-iodosuccinimide (15 mg, 0.066 mmol), portionwise. The reaction was stirred overnight at room temperature and then extracted from water with ethyl acetate. The combined organic layers were washed with brine, dried ($MgSO_4$), and then concentrated, in vacuo. Purification on a Biotage™ Flash 12S column using 20% ethyl acetate in hexanes as eluant afforded compound 15A-1 (15 mg, 46%) as a solid: +ESI MS (M+1) 522.3; $^1$H NMR (400 MHz, $CD_3OD$) δ 8.46 (s, 1H), 7.53–7.40 (m, 6H), 7.24 (d, J=8.7 Hz, 2H), 5.45–5.41 (m, 1H), 3.81–3.64 (m, 2H), 3.33 (d, J=6.2 Hz, 2H).

Example 16

Preparation of 6-Bromo-5-butyl-3-(4-chlorophenyl)-2-(2-chlorophenyl)-7-ethoxypyrazolo[1,5-a]pyrimidine (16A-1) and 5-Butyl-3-(4-chlorophenyl)-2-(2-chlorophenyl)-7-ethoxypyrazolo[1,5-a]pyrimidine (16A-2)

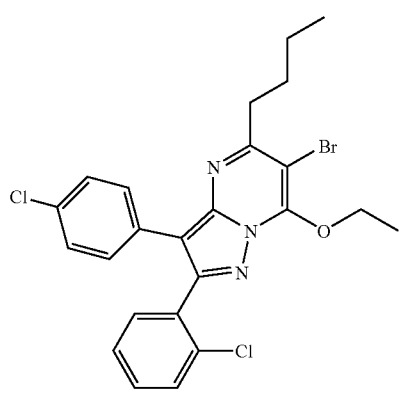

16A-1

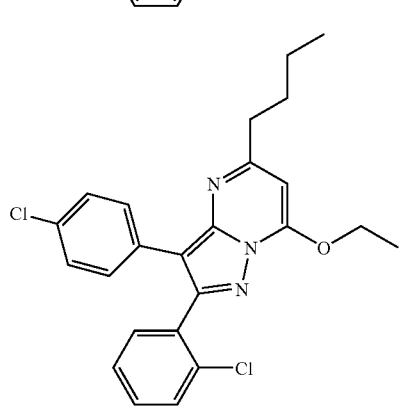

16A-2

To a solution of 3-(4-chlorophenyl)-2-(2-chlorophenyl)-7-ethoxypyrazolo[1,5-a]pyrimidine (11A-1; 50 mg, 0.13 mmol) in THF (0.5 ml) at −78° C. was 2.5M n-BuLi in hexanes (0.055 ml, 0.14 mmol), dropwise. After stirring for 1 hour, a solution of N-bromosuccinimide (28 mg, 0.16 mmol) in THF (0.5 ml) was added, dropwise. Following an additional 1.5 hours, the reaction was warmed to room temperature and stirred overnight. The mixture was extracted from water with ethyl acetate; the combined organic layers were washed with brine, dried ($MgSO_4$) and then concentrated, in vacuo. Purification on a Chromatotron using 60–10% hexanes in methylene chloride as eluant afforded compound 16A-1 (7.7 mg, 11%) and 16A-2 (23 mg, 40%) as a solids. 16A-1: +APcI MS (M+1) 518.1; $^1$H NMR (400 MHz, $CD_3OD$) δ 7.52–7.40 (m, 6H), 7.23 (d, J=8.7 Hz, 2H), 4.83 (q, J=7.1 Hz, 2H), 3.06 (t, J=7.5 Hz, 2H), 1.88–1.79 (m, 2H), 1.55–1.46 (m, 5H), 1.00 (t, J=7.3 Hz, 3H). 16A-2: +APcI MS (M+1) 440.1; $^1$H NMR (400 MHz, $CD_3OD$) δ 7.52–7.40 (m, 6H), 7.22 (d, J=8.7 Hz, 2H), 5.56 (s, 1H), 4.55 (q, J=7.1 Hz, 2H), 2.87 (t, J=7.7 Hz, 2H), 1.86–1.77 (m, 2H), 1.58 (t, J=7.0 Hz, 3H), 1.50–1.42 (m, 2H), 0.99 (t, J=7.3 Hz, 3H).

Example 17

Preparation of 6-Bromo-3-(4-chlorophenyl)-2-(2-chlorophenyl)-7-ethoxypyrazolo[1,5-a]pyrimidine (17A-1)

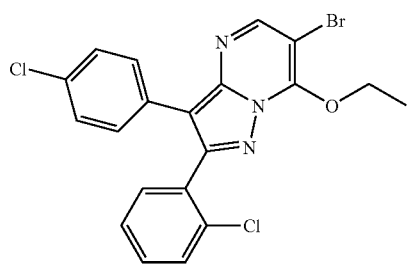

To a solution of 3-(4-chlorophenyl)-2-(2-chlorophenyl)-7-ethoxypyrazolo[1,5-a]pyrimidine (11A-1; 50 mg, 0.13 mmol) in 9:1 methylene chloride/chloroform (1.3 ml) at 0° C. was added N-iodosuccinimide (35 mg, 0.20 mmol), portionwise. The reaction was stirred overnight at room temperature and then extracted from water with ethyl acetate. The combined organic layers were washed with brine, dried (MgSO$_4$), and then concentrated, in vacuo. Purification on a Biotage™ Flash 12S column using 1:1 methylene chloride/hexanes as eluant afforded compound 17A-1 (47 mg, 78%) as a solid: +ESI MS (M+1) 462.0; $^1$H NMR (400 MHz, CD$_3$OD) δ 8.61 (s, 1H), 7.52–7.39 (m, 6H), 7.24 (d, J=8.7 Hz, 2H), 4.92 (q, J=7.1 Hz, 2H), 1.52 (t, J=7.1 Hz, 3H).

Pharmacological Testing

The utility of the compounds of the present invention in the practice of the instant invention can be evidenced by activity in at least one of the protocols described herein below. The following acronyms are used in the protocols described below.

BSA—bovine serum albumin
DMSO—dimethylsulfoxide
EDTA—ethylenediamine tetracetic acid
PBS—phosphate-buffered saline
EGTA—ethylene glycol-bis(β-aminoethyl ether) N,N,N',N'-tetraacetic acid
GDP—guanosine diphosphate
sc—subcutaneous
po—orally
ip—intraperitoneal
icv—intra cerebro ventricular
iv—intravenous
[$^3$H]SR141716A—radiolabeled N-(piperidin-1-yl)-5-(4-chlorophenyl)-1-(2,4-dichlorophenyl)-4-methyl-1H-pyrazole-3-carboxamide hydrochloride available from Amersham Biosciences, Piscataway, N.J.
[$^3$H]CP-55940—radiolabled 5-(1,1-dimethylheptyl)-2-[5-hydroxy-2-(3-hydroxypropyl)-cyclohexyl]-phenol available from NEN Life Science Products, Boston, Mass.
AM251—N-(piperidin-1-yl)-1-(2,4-dichlorophenyl)-5-(4-iodophenyl)-4-methyl-1H-pyrazole-3-carboxamide available from Tocris™, Ellisville, Mo.

All of the compounds listed in the Example section above were tested in the CB-1 receptor binding assay below. The compounds provided a range of binding activities from 0.2–155 nM. Those compounds having an activity <20 nM were then tested in the CB-1 GTPγ [$^{35}$S] Binding Assay and the CB-2 binding assay described below in the Biological Binding Assays section. Selected compounds were then tested in vivo using one or more of the functional assays described in the Biological Functional Assays section below.

In Vitro Biological Assays

Bioassay systems for determining the CB-1 and CB-2 binding properties and pharmacological activity of cannabinoid receptor ligands are described by Roger G. Pertwee in "Pharmacology of Cannabinoid Receptor Ligands" *Current Medicinal Chemistry*, 6, 635–664 (1999) and in WO 92/02640 (U.S. application Ser. No. 07/564,075 filed Aug. 8, 1990, incorporated herein by reference).

The following assays were designed to detect compounds that inhibit the binding of [$^3$H] SR141716A (selective radiolabeled CB-1 ligand) and [$^3$H] 5-(1,1-dimethylheptyl)-2-[5-hydroxy-2-(3-hydroxypropyl)-cyclohexyl]-phenol ([$^3$H] CP-55940; radiolabeled CB-1/CB-2 ligand) to their respective receptors.

Rat CB-1 Receptor Binding Protocol

PelFreeze brains (available from Pel Freeze Biologicals, Rogers, Ark.) were cut up and placed in tissue preparation buffer (5 mM Tris HCl, pH=7.4 and 2 mM EDTA), polytroned at high speed and kept on ice for 15 minutes. The homogenate was then spun at 1,000×g for 5 minutes at 4° C. The supernatant was recovered and centrifuged at 100,000×G for 1 hour at 4° C. The pellet was then re-suspended in 25 ml of TME (25 nM Tris, pH=7.4, 5 mM MgCl$_2$, and 1 mM EDTA) per brain used. A protein assay was performed and 200 µl of tissue totaling 20 µg was added to the assay.

The test compounds were diluted in drug buffer (0.5% BSA, 10% DMSO and TME) and then 25 µl were added to a deep well polypropylene plate. [$^3$H] SR141716A was diluted in a ligand buffer (0.5% BSA plus TME) and 25 µl were added to the plate. A BCA protein assay was used to determine the appropriate tissue concentration and then 200 µl of rat brain tissue at the appropriate concentration was added to the plate. The plates were covered and placed in an incubator at 20° C. for 60 minutes. At the end of the incubation period 250 µl of stop buffer (5% BSA plus TME) was added to the reaction plate. The plates were then harvested by Skatron onto GF/B filtermats presoaked in BSA (5 mg/ml) plus TME. Each filter was washed twice. The filters were dried overnight. In the morning the filters were counted on a Wallac Betaplate™ counter (available from PerkinElmer Life Sciences™, Boston, Mass.).

Human CB-1 Receptor Binding Protocol

Human embryonic kidney 293 (HEK 293) cells transfected with the CB-1 receptor cDNA (obtained from Dr. Debra Kendall, University of Connecticut) were harvested in homogenization buffer (10 mM EDTA, 10 mM EGTA, 10 mM Na Bicarbonate, protease inhibitors; pH=7.4), and homogenized with a Dounce Homogenizer. The homogenate was then spun at 1,000×g for 5 minutes at 4° C. The supernatant was recovered and centrifuged at 25,000×G for 20 minutes at 4° C. The pellet was then re-suspended in 10 ml of homogenization buffer and re-spun at 25,000×G for 20 minutes at 4° C. The final pellet was re-suspended in 1 ml of TME (25 mM Tris buffer (pH=7.4) containing 5 mM MgCl$_2$ and 1 mM EDTA). A protein assay was performed and 200 µl of tissue totaling 20 µg was added to the assay.

The test compounds were diluted in drug buffer (0.5% BSA, 10% DMSO and TME) and then 25 µl were added to a deep well polypropylene plate. [$^3$H] SR141716A was diluted in a ligand buffer (0.5% BSA plus TME) and 25 µl were added to the plate. The plates were covered and placed in an incubator at 30° C. for 60 minutes. At the end of the incubation period 250 µl of stop buffer (5% BSA plus TME) was added to the reaction plate. The plates were then harvested by Skatron onto GF/B filtermats presoaked in BSA (5 mg/ml) plus TME. Each filter was washed twice. The filters were dried overnight. In the morning the filters were counted on a Wallac Betaplate™ counter (available from PerkinElmer Life Sciences™, Boston, Mass.).

CB-2 Receptor Binding Protocol

Chinese hamster ovary-K1 (CHO-K1) cells transfected with CB-2 cDNA (obtained from Dr. Debra Kendall, University of Connecticut) were harvested in tissue preparation buffer (5 mM Tris-HCl buffer (pH=7.4) containing 2 mM EDTA), polytroned at high speed and kept on ice for 15 minutes. The homogenate was then spun at 1,000×g for 5 minutes at 4° C. The supernatant was recovered and centrifuged at 100,000×G for 1 hour at 4° C. The pellet was then re-suspended in 25 ml of TME (25 mM Tris buffer (pH=7.4) containing 5 mM MgCl$_2$ and 1 mM EDTA) per brain used. A protein assay was performed and 200 µl of tissue totaling 10 µg was added to the assay.

The test compounds were diluted in drug buffer (0.5% BSA, 10% DMSO, and 80.5% TME) and then 25 µl were added to the deep well polypropylene plate. [3H] CP-55940 was diluted a ligand buffer (0.5% BSA and 99.5% TME) and then 25 µl were added to each well at a concentration of 1 nM. A BCA protein assay was used to determine the appropriate tissue concentration and 200 µl of the tissue at the appropriate concentration was added to the plate. The plates were covered and placed in an incubator at 30° C. for 60 minutes. At the end of the incubation period 250 µl of stop buffer (5% BSA plus TME) was added to the reaction plate. The plates were then harvested by Skatron format onto GF/B filtermats presoaked in BSA (5 mg/ml) plus TME. Each filter was washed twice. The filters were dried overnight. The filters were then counted on the Wallac Betaplate™ counter.

CB-1 GTPγ [$^{35}$S]Binding Assay

Membranes were prepared from CHO-K1 cells stably transfected with the human CB-1 receptor cDNA. Membranes were prepared from cells as described by Bass et al, in "Identification and characterization of novel somatostatin antagonists," *Molecular Pharmacology*, 50, 709–715 (1996). GTPγ [$^{35}$S] binding assays were performed in a 96 well FlashPlate™ format in duplicate using 100 pM GTPγ [$^{35}$S] and 10 µg membrane per well in assay buffer composed of 50 mM Tris HCl, pH 7.4, 3 mM MgCl$_2$, pH 7.4, 10 mM MgCl$_2$, 20 mM EGTA, 100 mM NaCl, 30 µM GDP, 0.1% bovine serum albumin and the following protease inhibitors: 100 µg/ml bacitracin, 100 µg/ml benzamidine, 5 µg/ml aprotinin, 5 µg/ml leupeptin. The assay mix was then incubated with increasing concentrations of antagonist ($10^{-10}$ M to $10^{-5}$ M) for 10 minutes and challenged with the cannabinoid agonist CP-55940 (10 µM). Assays were performed at 30° C. for one hour. The FlashPlates™ were then centrifuged at 2000×g for 10 minutes. Stimulation of GTPγ [$^{35}$S] binding was then quantified using a Wallac Microbeta. EC$_{50}$ calculations done using Prism™ by Graphpad.

Inverse agonism was measured in the absense of agonist.

CB-1 FLIPR-based Functional Assay Protocol

CHO-K1 cells co-transfected with the human CB-1 receptor cDNA (obtained from Dr. Debra Kendall, University of Connecticut) and the promiscuous G-protein G16 were used for this assay. Cells were plated 48 hours in advance at 12500 cells per well on collagen coated 384 well black clear assay plates. Cells were incubated for one hour with 4µM Fluo-4 AM (Molecular Probes) in DMEM (Gibco) containing 2.5 mM probenicid and pluronic acid (0.04%). The plates were then washed 3 times with HEPES-buffered saline (containing probenicid; 2.5 mM) to remove excess dye. After 20 minutes the plates were added to the FLIPR individually and fluorescence levels was continuously monitored over an 80 second period. Compound additions were made simultaneously to all 384 wells after 20 seconds of baseline. Assays were performed in triplicate and 6 point concentration-response curves generated. Antagonist compounds were subsequently challenged with 3 µM WIN 55,212-2 (agonist). Data were analyzed using Graph Pad Prism.

Detection of Inverse Agonists

The following cyclic-AMP assay protocol using intact cells was used to determine inverse agonist activity.

Cells were plated into a 96-well plate at a plating density of 10,000–14,000 cells per well at a concentration of 100 µl per well. The plates were incubated for 24 hours in a 37° C. incubator. The media was removed and media lacking serum (100 µl) was added. The plates were then incubated for 18 hours at 37° C.

Serum free medium containing 1 mM IBMX was added to each well followed by 10 µl of test compound (1:10 stock solution (25 mM compound in DMSO) into 50% DMSO/ PBS) diluted 10× in PBS with 0.1% BSA. After incubating for 20 minutes at 37° C., 2 µM of Forskolin was added and then incubated for an additional 20 minutes at 37° C. The media was removed, 100 µl of 0.01N HCl was added and then incubated for 20 minutes at room temperature. Cell lysate (75 µl) along with 25 µl of assay buffer (supplied in FlashPlate™ cAMP assay kit available from NEN Life Science Products Boston, Mass.) into a Flashplate. cAMP standards and cAMP tracer were added following the kit's protocol. The flashplate was then incubated for 18 hours at 4° C. The content of the wells were aspirated and counted in a Scintillation counter.

In Vivo Biological Assays

Cannabinoid agoinists such as Δ$^9$-tetrahydrocannabinol (Δ$^9$-THC) and CP-55940 have been shown to affect four characteristic behaviors in mice, collectively known as the Tetrad. For a description of these behaviors see: Smith, P. B., et al. in "The pharmacological activity of anandamide, a putative endogenous cannabinoid, in mice." J. Pharmacol. Exp. Ther., 270(1), 219–227 (1994) and Wiley, J., et al. in "Discriminative stimulus effects of anandamide in rats," Eur. J. Pharmacol., 276(1–2), 49–54 (1995). Reversal of these activities in the Locomotor Activity, Catalepsy, Hypothermia, and Hot Plate assays described below provides a screen for in vivo activity of CB-1 antagonists.

All data is presented as % reversal from agonist alone using the following formula: (CP/agonist-vehicle/agonist)/(vehicle/vehicle-vehicle/agonist). Negative numbers indicate a potentiation of the agonist activity or non-antagonist activity. Positive numbers indicate a reversal of activity for that particular test.

Locomotor Activity

Male ICR mice (n=6; 17–19 g, Charles River Laboratories, Inc., Wilmington, Mass.) were pre-treated with test compound (sc, po, ip, or icv). Fifteen minutes later, the mice were challenged with CP-55940 (sc). Twenty-five minutes after the agonist injection, the mice were placed in clear acrylic cages (431.8 cm×20.9 cm×20.3 cm) containing clean wood shavings. The subjects were allowed to explore surroundings for a total of about 5 minutes and the activity was recorded by infrared motion detectors (available from Coulbourn Instruments™, Allentown, Pa.) that were placed on top of the cages. The data was computer collected and expressed as "movement units."

Catalepsy

Male ICR mice (n=6; 17–19 g upon arrival) were pre-treated with test compound (sc, po, ip or icv). Fifteen minutes later, the mice were challenged with CP-55940 (sc). Ninety minutes post injection, the mice were placed on a 6.5 cm steel ring attached to a ring stand at a height of about 12 inches. The ring was mounted in a horizontal orientation and the mouse was suspended in the gap of the ring with fore- and hind-paws gripping the perimeter. The duration that the mouse remained completely motionless (except for respiratory movements) was recorded over a 3-minute period.

The data were presented as a percent immobility rating. The rating was calculated by dividing the number of seconds the mouse remains motionless by the total time of the observation period and multiplying the result by 100. A percent reversal from the agonist was then calculated.

Hypothermia

Male ICR mice (n=5; 17–19 g upon arrival) were pre-treated with test compounds (sc, po, ip or icv). Fifteen minutes later, mice were challenged with the cannabinoid agonist CP-55940 (sc). Sixty-five minutes post agonist injection, rectal body temperatures were taken. This was done by inserting a small thermostat probe approximately 2–2.5 cm into the rectum. Temperatures were recorded to the nearest tenth of a degree Hot Plate Male ICR mice (n=7; 17–19 g upon arrival) are pre-treated with test compounds (sc, po, ip or iv). Fifteen minutes later, mice were challenged with a cannabinoid agonist CP-55940 (sc). Forty-five minutes later, each mouse was tested for reversal of analgesia using a standard hot plate meter (Columbus Instruments). The hot plate was 10"×10"×0.75" with a surrounding clear acrylic wall. Latency to kick, lick or flick hindpaw or jump from the platform was recorded to the nearest tenth of a second. The timer was experimenter activated and each test had a 40 second cut off. Data were presented as a percent reversal of the agonist induced analgesia.

Food Intake

The following screen was used to evaluate the efficacy of test compounds for inhibiting food intake in Sprague-Dawley rats after an overnight fast.

Male Sprague-Dawley rats were obtained from Charles River Laboratories, Inc. (Wilmington, Mass.). The rats were individually housed and fed powdered chow. They were maintained on a 12-hour light/dark cycle and received food and water ad libitum. The animals were acclimated to the vivarium for a period of one week before testing was conducted. Testing was completed during the light portion of the cycle.

To conduct the food intake efficacy screen, rats were transferred to individual test cages without food the afternoon prior to testing, and the rats were fasted overnight. After the overnight fast, rats were dosed the following morning with vehicle or test compounds. A known antagonist was dosed (3 mg/kg) as a positive control, and a control group received vehicle alone (no compound). The test compounds were dosed at ranges between 0.1 and 100 mg/kg depending upon the compound. The standard vehicle was 0.5% (w/v) methylcellulose in water and the standard route of administration was oral. However, different vehicles and routes of administration were used to accommodate various compounds when required. Food was provided to the rats 30 minutes after dosing and the Oxymax automated food intake system (Columbus Instruments, Columbus, Ohio) was started. Individual rat food intake was recorded continuously at 10-minute intervals for a period of two hours. When required, food intake was recorded manually using an electronic scale; food was weighed every 30 minutes after food was provided up to four hours after food was provided. Compound efficacy was determined by comparing the food intake pattern of compound-treated rats to vehicle and the standard positive control.

Alcohol Intake

The following protocol evaluates the effects of alcohol intake in alcohol preferring (P) female rats (bred at Indiana University) with an extensive drinking history. The following references provide detailed descriptions of P rats: Li, T.-K., et al., "Indiana selection studies on alcohol related behaviors" in *Development of Animal Models as Pharmacogenetic Tools* (eds McClearn C. E., Deitrich R. A. and Erwin V. G.), Research Monograph 6, 171–192 (1981) NIAAA, ADAMHA, Rockville, Md.; Lumeng, L, et al., "New strains of rats with alcohol preference and nonpreference" *Alcohol And Aldehyde Metabolizing Systems*, 3, Academic Press, New York, 537–544 (1977); and Lumeng, L, et al., "Different sensitivities to ethanol in alcohol-preferring and -nonpreferring rats," *Pharmacol. Biochem Behav.*, 16, 125–130 (1982).

Female rats were given 2 hours of access to alcohol (10% v/v and water, 2-bottle choice) daily at the onset of the dark cycle. The rats were maintained on a reverse cycle to facilitate experimenter interactions. The animals were initially assigned to four groups equated for alcohol intakes: Group 1—vehicle (n=8); Group 2—positive control (e.g. 5.6 mg/kg AM251; n=8); Group 3—low dose test compound (n=8); and Group 4—high dose of test compound (n=8). Test compounds were generally mixed into a vehicle of 30% (w/v) β-cyclodextrin in distilled water at a volume of 1–2 ml/kg. Vehicle injections were given to all groups for the first two days of the experiment. This was followed by 2 days of drug injections (to the appropriate groups) and a final day of vehicle injections. On the drug injection days, drugs were given sc 30 minutes prior to a 2-hour alcohol access period. Alcohol intake for all animals was measured during the test period and a comparison was made between test compound and vehicle-treated animals to determine effects of the compounds on alcohol drinking behavior.

Additional drinking studies were done utilizing female C57Bl/6 mice (Charles River). Several studies have shown that this strain of mice will readily consume alcohol with little to no manipulation required (Middaugh et al., "Ethanol Consumption by C57BL/6 Mice: Influence of Gender and Procedural Variables" *Alcohol*, 17 (3), 175–183, 1999; Le et al., "Alcohol Consumption by C57BL/6, BALA/c, and DBA/2 Mice in a Limited Access Paradigm" *Pharmacology Biochemisrty and Behavior*, 47, 375–378, 1994).

For our purposes, upon arrival (17–19 g) mice were individually housed and given unlimited access to powdered rat chow, water and a 10% (w/v) alcohol solution. After 2–3 weeks of unlimited access, water was restricted for 20 hours and alcohol was restricted to only 2 hours access daily. This was done in a manner that the access period was the last 2 hours of the dark part of the light cycle.

Once drinking behavior stabilized, testing commenced. Mice were considered stable when the average alcohol consumption for 3 days was ±20% of the average for all 3 days. Day 1 of test consisted of all mice receiving vehicle injection (sc or ip). Thirty to 120 minutes post injection access was given to alcohol and water. Alcohol consumption for that day was calculated (g/kg) and groups were assigned (n=7–10) so that all groups had equivocal alcohol intake. On day 2 and 3, mice were injected with vehicle or drug and the same protocol as the previous day was followed. Day 4 was wash out and no injections were given. Data was analyzed using repeated measures ANOVA. Change in water or alcohol consumption was compared back to vehicle for each day of the test. Positive results would be interpreted as a compound that was able to significantly reduce alcohol consumption while having no effect on water Oxygen Consumption Methods:

Whole body oxygen consumption is measured using an indirect calorimeter (Oxymax from Columbus Instruments, Columbus, Ohio) in male Sprague Dawley rats (if another rat strain or female rats are used, it will be specified). Rats (300–380 g body weight) are placed in the calorimeter chambers and the chambers are placed in activity monitors. These studies are done during the light cycle. Prior to the measurement of oxygen consumption, the rats are fed standard chow ad libitum. During the measurement of oxygen consumption, food is not available. Basal pre-dose oxygen consumption and ambulatory activity are measured every 10 minutes for 2.5 to 3 hours. At the end of the basal pre-dosing period, the chambers are opened and the animals are administered a single dose of compound (the usual dose range is 0.001 to 10 mg/kg) by oral gavage (or other route of administration as specified, i.e., sc, ip, iv). Test compounds are prepared in methylcellulose, water or other specified vehicle (examples include PEG400, 30% beta-cyclo dextran and propylene glycol). Oxygen consumption and ambulatory activity are measured every 10 minutes for an additional 1–6 hours post-dosing.

The Oxymax calorimeter software calculates the oxygen consumption (ml/kg/h) based on the flow rate of air through the chambers and difference in oxygen content at inlet and output ports. The activity monitors have 15 infrared light beams spaced one inch apart on each axis, ambulatory activity is recorded when two consecutive beams are broken and the results are recorded as counts.

Resting oxygen consumption, during pre- and post-dosing, is calculated by averaging the 10-min O2 consumption values, excluding periods of high ambulatory activity (ambulatory activity count>100) and excluding the first 5 values of the pre-dose period and the first value from the post-dose period. Change in oxygen consumption is reported as percent and is calculated by dividing the post-dosing resting oxygen consumption by the pre-dose oxygen consumption*100. Experiments will typically be done with n=4–6 rats and results reported are mean+/–SEM.

Interpretation:

An increase in oxygen consumption of >10% is considered a positive result. Historically, vehicle-treated rats have no change in oxygen consumption from pre-dose basal.

The invention claimed is:

1. A compound of Formula (I)

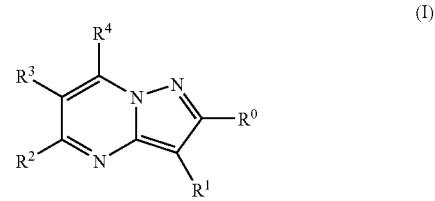

wherein $R^0$ is an optionally substituted aryl or an optionally substituted heteroaryl;

$R^1$ is an optionally substituted aryl;

$R^2$ and $R^3$ are each independently hydrogen, halo, $(C_1-C_4)$alkyl, halo-substituted $(C_1-C_4)$alkyl, or $(C_1-C_4)$alkoxy;

$R^4$ is (i) a group having Formula (IA) or Formula (IB)

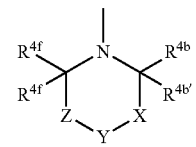

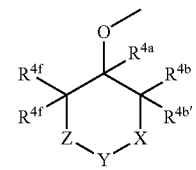

where $R^{4a}$ is hydrogen or $(C_1-C_3)$alkyl;

$R^{4b}$ and $R^{4b'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3–6 membered partially or fully saturated heterocycle, and a partially or fully saturated carbocyclic ring, where said moiety is optionally substituted with one or more substituents, or either $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —CH$_2$CH$_2$— or —C(R$^{4c}$)(R$^{4c'}$)—, where $R^{4c}$ and $R^{4c'}$ are each independently hydrogen, cyano, hydroxy, amino, H$_2$NC(O)—, or a chemical moiety selected from the group consisting of (C$_1$–C$_6$)alkyl, (C$_1$–C$_6$)alkoxy, acyloxy, acyl, (C$_1$–C$_3$)alkyl-O—C(O)—, (C$_1$–C$_4$)alkyl-NH—C(O)—, ((C$_1$–C$_4$)alkyl)$_2$N—C(O)—, (C$_1$–C$_6$)alkylamino-, di(C$_1$–C$_4$)alkylamino-, (C$_3$–C$_6$)cycloalkylamino-, acylamino-, aryl(C$_1$–C$_4$)alkylamino-, heteroaryl(C$_1$–C$_4$)alkylamino-, aryl, heteroaryl, a 3–6 membered partially or fully saturated heterocycle, and a 3–6 membered partially or fully saturated carbocyclic ring, where said moiety is optionally substituted with one or more substituents, or either $R^{4c}$ or $R^{4c'}$ taken together with $R^{4e}$, $R^{4e'}$, $R^{4f}$, or $R^{4f'}$ forms a bond, a methylene bridge or an ethylene bridge;

Y is oxygen, sulfur, —C(O)—, or —C(R$^{4d}$)(R$^{4d'}$)—, where $R^{4d}$ and $R^{4d'}$ are each independently hydrogen, cyano, hydroxy, amino, H$_2$NC(O)—, or a chemical moiety selected from the group consisting of (C$_1$–C$_6$)alkyl, (C$_1$–C$_6$)alkoxy, acyloxy, acyl, (C$_1$–C$_3$)alkyl-O—C(O)—, (C$_1$–C$_4$)alkyl-NH—C(O)—, ((C$_1$–C$_4$)alkyl)$_2$N—C(O)—, (C$_1$–C$_6$)alkylamino-, di(C$_1$–C$_4$)alkylamino-, (C$_3$–C$_6$)cycloalkylamino-, acylamino-, aryl(C$_1$–C$_4$)alkylamino-, heteroaryl(C$_1$–C$_4$)alkylamino-, aryl, heteroaryl, a 3–6 membered partially or fully saturated heterocycle, and a 3–6 membered partially or fully saturated carbocyclic ring, where said moiety is optionally substituted with one or more substituents, or $R^{4d}$ and $R^{4d'}$ taken together form a 3–6 membered partially or fully saturated carbocyclic ring, 3–6 membered partially or fully saturated heterocyclic ring, a 5–6 membered lactone ring, or a 4–6 membered lactam ring, where said carbocyclic ring, said heterocyclic ring, said lactone ring and said lactam ring are optionally substituted with one or more substituents and said lactone ring and said lactam ring optionally contain an additional heteroatom selected from oxygen, nitrogen or sulfur, or Y is —NR$^{4d''}$—, where R$^{4d''}$ is a hydrogen or a chemical moiety selected from the group consisting of (C$_1$–C$_6$)alkyl, (C$_3$–C$_6$)cycloalkyl, (C$_1$–C$_3$)alkylsulfonyl-, (C$_1$–C$_3$)alkylaminosulfonyl-, di(C$_1$–C$_3$)alkylaminosulfonyl-, acyl, (C$_1$–C$_6$)alkyl-O—C(O)—, aryl, and heteroaryl, where said moiety is optionally substituted with one or more substituents;

Z is a bond, —CH$_2$CH$_2$—, or —C(R$^{4e}$)(R$^{4e'}$)—, where $R^{4e}$ and $R^{4e'}$ are each independently hydrogen, cyano, hydroxy, amino, H$_2$NC(O)—, or a chemical moiety selected from the group consisting of (C$_1$–C$_6$)alkyl, (C$_1$–C$_6$)alkoxy, acyloxy, acyl, (C$_1$–C$_3$)alkyl-O—C(O)—, (C$_1$–C$_4$)alkyl-NH—C(O)—, ((C$_1$–C$_4$)alkyl)$_2$N—C(O)—, (C$_1$–C$_6$)alkylamino-, di(C$_1$–C$_4$)alkylamino-, (C$_3$–C$_6$)cycloalkylamino-, acylamino-, aryl(C$_1$–C$_4$)alkylamino-, heteroaryl(C$_1$–C$_4$)alkylamino-, aryl, heteroaryl, a 3–6 membered partially or fully saturated heterocycle, and a 3–6 membered partially or fully saturated carbocyclic ring, where said moiety is optionally substituted with one or more substituents, or either $R^{4e}$ or $R^{4e'}$ taken together with $R^{4b}$, $R^{4b'}$, $R^{4c}$, or $R^{4c'}$ forms a bond, a methylene bridge or an ethylene bridge; and $R^{4f}$ and $R^{4f'}$ are each independently hydrogen, cyano, hydroxy, amino, H$_2$NC(O)—, or a chemical moiety selected from the group consisting of (C$_1$–C$_6$)alkyl, (C$_1$–C$_6$)alkoxy, acyloxy, acyl, (C$_1$–C$_3$)alkyl-O—C(O)—, (C$_1$–C$_4$)alkyl-NH—C(O)—, ((C$_1$–C$_4$)alkyl)$_2$N—C(O)—, (C$_1$–C$_6$)alkylamino-, di(C$_1$–C$_4$)alkylamino-, (C$_3$–C$_6$)cycloalkylamino-, acylamino-, aryl(C$_1$–C$_4$)alkylamino-, heteroaryl(C$_1$–C$_4$)alkylamino-, aryl, heteroaryl, a 3–6 membered partially or fully saturated heterocycle, and a 3–6 membered partially or fully saturated carbocyclic ring, where said moiety is optionally substituted with one or more substituents, or either $R^{4f}$ or $R^{4f'}$ taken together with $R^{4b}$, $R^{4b'}$, $R^{4c}$, or $R^{4c'}$ forms a bond, a methylene bridge or an ethylene bridge; or (ii) —O—R$^5$, where R$^5$ taken together with R$^3$ forms a 5- to 6-membered partially saturated heterocyclic ring optionally containing an additional oxygen, or a 5-membered heteroaryl, said heterocyclic ring and said heteroaryl being optionally substituted with one or more substituents;

or a pharmaceutically acceptable salt thereof.

2. The compound of claim 1 wherein R$^4$ is a group having Formula (IA)

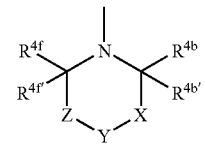

IA where, $R^{4b}$ and $R^{4b'}$ are each independently hydrogen, H$_2$NC(O)—, or a chemical moiety selected from the group consisting of (C$_1$–C$_6$)alkyl, acyl, (C$_1$–C$_3$)alkyl-O—C(O)—, (C$_1$–C$_4$)alkyl-NH—C(O)—, (C$_1$–C$_4$)alkyl)$_2$N—C(O)—, aryl, heteroaryl, a 3–6 membered partially or fully saturated heterocycle, and a partially or fully saturated carbocyclic ring, where said moiety is optionally substituted with one or more substituents, or $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —CH$_2$CH$_2$— or —C(R$^{4c}$)(R$^{4c'}$)—, where R$^{4c}$ is hydrogen, cyano, hydroxy, amino, H$_2$NC(O)—, or a chemical moiety selected from the group consisting of (C$_1$–C$_6$)alkyl, (C$_1$–C$_6$)alkoxy, acyloxy, acyl, (C$_1$–C$_3$)alkyl-O—C(O)—, (C$_1$–C$_4$)alkyl-NH—C(O)—, (C$_1$–C$_4$)alkyl)$_2$N—C(O)—, (C$_1$–C$_6$)alkylamino-, ((C$_1$–C$_4$)alkyl)$_2$amino-, (C$_3$–C$_6$)cycloalkylamino-, acylamino-, aryl(C$_1$–C$_4$)alkylamino-, heteroaryl(C$_1$–C$_4$)alkylamino-, aryl, heteroaryl, a 3–6 membered partially or fully saturated heterocycle, and a partially or fully saturated carbocyclic ring, where said moiety is optionally substituted with one or more substituents, or $R^{4c}$ taken together with $R^{4e}$, $R^{4e'}$, $R^{4f}$, or $R^{4f'}$ forms a bond, a methylene bridge, or an ethylene bridge, and $R^{4c'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $((C_1-C_4)$alkyl$)_2$N—C(O)—, aryl, heteroaryl, a 3–6 membered partially or fully saturated heterocycle, and a partially or fully saturated carbocyclic ring, where said moiety is optionally substituted with one or more substituents, or $R^{4c'}$ taken together with $R^{4e}$, $R^{4e'}$, $R^{4f}$, or $R^{4f'}$ forms a bond, a methylene bridge, or an ethylene bridge;

Y is oxygen, sulfur, —C(O)—, or —C($R^{4d}$)($R^{4d'}$)—, where $R^{4d}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, $((C_1-C_4)$alkyl$)_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3–6 membered partially or fully saturated heterocycle, and a partially or fully saturated carbocyclic ring, where said moiety is optionally substituted with one or more substituents, and $R^{4d'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $((C_1-C_4)$alkyl$)_2$N—C(O)—, aryl, heteroaryl, a 3–6 membered partially or fully saturated heterocycle, and a partially or fully saturated carbocyclic ring, where said moiety is optionally substituted with one or more substituents, or $R^{4d}$ and $R^{4d'}$ taken together form a 3–6 membered partially or fully saturated carbocyclic ring, a 3–6 membered partially or fully saturated heterocyclic ring, a 5–6 membered lactone ring, or a 4–6 membered lactam ring, where said carbocyclic ring, said heterocyclic ring, said lactone ring and said lactam ring are optionally substituted with one or more substituents and said lactone ring and said lactam ring optionally contain an additional heteroatom selected from oxygen, nitrogen or sulfur, or Y is —$NR^{4d''}$—, where $R^{4d''}$ is a hydrogen or a chemical moiety selected from the group consisting of $(C_1-C_6)$ alkyl, $(C_3-C_6)$cycloalkyl, $(C_1-C_3)$alkylsulfonyl-, $(C_1-C_3)$alkylaminosulfonyl-, di$(C_1-C_3)$alkylaminosulfonyl-, acyl, $(C_1-C_6)$alkyl-O—C(O)—, aryl, and heteroaryl, where said moiety is optionally substituted with one or more substituents;

Z is a bond, —$CH_2CH_2$—, or —C($R^{4e}$)($R^{4e'}$)—, where $R^{4e}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, $((C_1-C_4)$alkyl$)_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3–6 membered partially or fully saturated heterocycle, and a partially or fully saturated carbocyclic ring, where said moiety is optionally substituted with one or more substituents, or $R^{4e}$ taken together with $R^{4b}$, $R^{4b'}$, $R^{4c}$ or $R^{4c'}$ forms a bond, a methylene bridge, or an ethylene bridge, and $R^{4e'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $((C_1-C_4)$alkyl$)_2$N—C(O)—, aryl, heteroaryl, a 3–6 membered partially or fully saturated heterocycle, and a partially or fully saturated carbocyclic ring, where said moiety is optionally substituted with one or more substituents, or $R^{4e'}$ taken together with $R^{4b}$, $R^{4b'}$, $R^{4c}$ or $R^{4c'}$ forms a bond, a methylene bridge, or an ethylene bridge; and $R^{4f}$ and $R^{4e'}$ are each independently hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $((C_1-C_4)$alkyl$)_2$N—C(O)—, aryl, heteroaryl, a 3–6 membered partially or fully saturated heterocycle, and a partially or fully saturated carbocyclic ring, where said moiety is optionally substituted with one or more substituents, or $R^{4f}$ or $R^{4f'}$ taken together with $R^{4b}$, $R^{4b'}$, $R^{4e}$, or $R^{4c'}$ forms a bond, a methylene bridge, or an ethylene bridge;

or a pharmaceutically acceptable salt thereof.

3. The compound of claim of 2 wherein $R^0$ and $R^1$ are each independently a substituted phenyl;

$R^{4b}$ is hydrogen, an optionally substituted $(C_1-C_3)$alkyl, or taken together with $R^{4e}$, $R^{4e'}$, $R^{4f}$, or $R^{4f'}$ forms a bond, a methylene bridge, or an ethylene bridge;

$R^{4b'}$ is hydrogen, an optionally substituted $(C_1-C_3)$alkyl, or taken together with $R^{4e}$, $R^{4e'}$, $R^{4e}$, or $R^{4f'}$ forms a bond, a methylene bridge, or an ethylene bridge;

$R^{4f}$ is hydrogen, an optionally substituted $(C_1-C_3)$alkyl, or taken together with $R^{4b}$, $R^{4b'}$, $R^{4c}$, or $R^{4c'}$ forms a bond, a methylene bridge, or an ethylene bridge; and $R^{4f'}$ is hydrogen, an optionally substituted $(C_1-C_3)$alkyl, or taken together with $R^{4b}$, $R^{4b'}$, $R^{4c}$, or $R^{4c'}$ forms a bond, a methylene bridge, or an ethylene bridge;

or a pharmaceutically acceptable salt thereof.

4. The compound of claim 3 wherein

X is —C($R^{4c}$)($R^{4c'}$)—, where $R^{4c}$ and $R^{4c'}$ are each independently hydrogen, $H_2NC(O)$—, or a chemical moiety selected from $(C_1-C_6)$alkyl, $(C_1-C_4)$alkyl-NH—C(O)—, or $((C_1-C_4)$alkyl$)_2$N—C(O)—, where said moiety is optionally substituted with one or more substituents, or either $R^{4c}$ or $R^{4c'}$ taken together with $R^{4e}$, $R^{4e'}$, $R^{4f}$, or $R^{4f'}$ forms a bond, a methylene bridge or an ethylene bridge;

Y is —$NR^{4d''}$—, where $R^{4d''}$ is a hydrogen or a chemical moiety selected from the group consisting of $(C_1-C_6)$ alkyl, $(C_3-C_6)$cycloalkyl, $(C_1-C_3)$alkylsulfonyl, $(C_1-C_3)$alkylaminosulfonyl, di$(C_1-C_3)$alkylaminosulfonyl, acyl, $(C_1-C_6)$alkyl-O—C(O)—, aryl, and heteroaryl, where said moiety is optionally substituted with one or more substituents;

Z is —C($R^{4e}$)($R^{4e'}$)—, where $R^{4e}$ and $R^{4e'}$ are each independently hydrogen, $H_2NC(O)$—, or a chemical moiety selected from $(C_1-C_6)$alkyl, $(C_1-C_4)$alkyl-NH—C(O)—, or $((C_1-C_4)$alkyl$)_2$N—C(O)—, where said moiety is optionally substituted with one or more substituents, or either $R^{4e}$ or $R^{4e'}$ taken together with $R^{4b}$, $R^{4b'}$, $R^{4c}$, or $R^{4c'}$ forms a bond, a methylene bridge or an ethylene bridge;

or a pharmaceutically acceptable salt thereof.

5. The compound of claim 4 wherein $R^{4d''}$ is a hydrogen or a chemical moiety selected from the group consisting of $(C_1-C_3)$alkylsulfonyl, $(C_1-C_3)$alkylaminosulfonyl, di$(C_1-C_3)$alkylaminosulfonyl, acyl, $(C_1-C_6)$alkyl-O—C(O)—, and heteroaryl, where said moiety is optionally substituted with one or more substituents;

or a pharmaceutically acceptable salt thereof.

6. The compound of claim 5 wherein $R^{4d''}$ is a hydrogen or a chemical moiety selected from the group consisting of $(C_1-C_3)$alkylsulfonyl, $(C_1-C_3)$alkylaminosulfonyl, di$(C_1-C_3)$alkylaminosulfonyl, acyl, and $(C_1-C_6)$alkyl-O—C(O)—, where said moiety is optionally substituted with 1–3 fluorines, or $R^{4d''}$ is a heteroaryl, where said heteroaryl is optionally substituted with 1 to 2 substituents independently selected from the group consisting of chloro, fluoro, $(C_1-C_3)$alkoxy, $(C_1-C_3)$alkyl, and fluoro-substituted $(C_1-C_3)$alkyl;

or a pharmaceutically acceptable salt thereof.

7. The compound of claim 4, 5 or 6 wherein $R^0$ and $R^1$ are each independently a phenyl substituted with 1 to 3 substituents independently selected from the group consisting of halo, $(C_1-C_4)$alkoxy, $(C_1-C_4)$alkyl, halo-substituted $(C_1-C_4)$alkyl, and cyano;

or a pharmaceutically acceptable salt thereof.

8. The compound of claim 7 wherein $R^0$ and $R^1$ are each independently a phenyl substituted with 1 to 2 substituents independently selected from the group consisting of chloro, fluoro, $(C_1-C_4)$alkoxy, $(C_1-C_4)$alkyl, fluoro-substituted $(C_1-C_4)$alkyl), and cyano;

or a pharmaceutically acceptable salt thereof.

9. The compound of claim 8 wherein $R^0$ is 2-chlorophenyl, 2-fluorophenyl, 2,4-dichlorophenyl, 2-fluoro-4-chlorophenyl, 2-chloro-4-fluorophenyl, or 2,4-difluorophenyl; and $R^1$ is 4-chlorophenyl or 4-fluorophenyl;

or a pharmaceutically acceptable salt thereof.

10. The compound of claim 9 selected from the group consisting of 3-(4-chlorophenyl)-2-(2-chlorophenyl)-5-methyl-7-(4-methylpiperazin-1-yl)-pyrazolo[1,5-a]pyrimidine;

3-(4-chlorophenyl)-2-(2-chlorophenyl)-5-methyl-7-(4-pyrimidin-2-yl-piperazin-1-yl)-pyrazolo[1,5-a]pyrimidine;

3-(4-chloro-phenyl)-2-(2-chlorophenyl)-7-[(1S,4S)-5-methanesulfonyl-2,5-diazabicyclo[2.2.1]hept-2-yl]-5-methylpyrazolo[1,5-a]pyrimidine;

3-(4-chlorophenyl)-2-(2-chlorophenyl)-5-methyl-7-[4-(propane-2-sulfonyl)-piperazin-1-yl]-pyrazolo[1,5-a]pyrimidine;

3-(4-chlorophenyl)-2-(2-chlorophenyl)-7-(4-ethanesulfonyl-piperazin-1-yl)-5-methylpyrazolo[1,5-a]pyrimidine;

3-(4-chlorophenyl)-2-(2-chlorophenyl)-7-(4-methanesulfonylpiperazin-1-yl)-5-methylpyrazolo[1,5-a]pyrimidine;

1-{4-[3-(4-chlorophenyl)-2-(2-chlorophenyl)-5-methylpyrazolo[1,5-a]pyrimidin-7-yl]-piperazin-1-yl}-ethanone;

4-[3-(4-chlorophenyl)-2-(2-chlorophenyl)-5-methylpyrazolo[1,5-a]pyrimidin-7-yl]-piperazine-1-carboxylic acid tert-butyl ester;

3-(4-chlorophenyl)-2-(2-chlorophenyl)-5-methyl-7-[(1S,4S)-5-(propane-2-sulfonyl)-2,5-diazabicyclo[2.2.1]hept-2-yl]-pyrazolo[1,5-a]pyrimidine;

1-{(1S,4S)-5-[3-(4-chlorophenyl)-2-(2-chlorophenyl)-5-methylpyrazolo [1,5-a]pyrimidin-7-yl]-2,5-diazabicyclo[2.2.1]hept-2-yl}-ethanone; and (1S,4S)-5-[3-(4-chlorophenyl)-2-(2-chlorophenyl)-5-methylpyrazolo[1,5-a]pyrimidin-7-yl]-2,5-diazabicyclo[2.2.1]heptane-2-carboxylic acid tert-butyl ester or a pharmaceutically acceptable salt thereof.

11. The compound of claim 3 wherein Y is —C($R^{4d}$)($R^{4d'}$)—, where $R^{4d}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3–6 membered partially or fully saturated heterocycle, and a partially or fully saturated carbocyclic ring, where said moiety is optionally substituted with one or more substituents, $R^{4d'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a 3–6 membered partially or fully saturated heterocycle, and a partially or fully saturated carbocyclic ring, where said moiety is optionally substituted, or $R^{4d}$ and $R^{4d'}$ taken together form a 3–6 membered partially or fully saturated carbocyclic ring, a 3–6 membered partially or fully saturated heterocyclic ring, a 5–6 membered lactone ring, or a 4–6 membered lactam ring, where said carbocyclic ring, said heterocyclic ring, said lactone ring and said lactam ring are optionally substituted with one or more substituents and said lactone ring and said lactam ring optionally contain an additional heteroatom selected from oxygen, nitrogen or sulfur;

or a pharmaceutically acceptable salt thereof.

12. The compound of claim 11 wherein $R^{4b}$, $R^{4b'}$, $R^{4f}$, and $R^{4f'}$ are all hydrogen;

$R^{4d}$ is amino, $(C_1-C_6)$alkylamino, di$(C_1-C_4)$alkylamino, $(C_3-C_6)$cycloalkylamino, acylamino, aryl$(C_1-C_4)$alkylamino-, heteroaryl$(C_1-C_4)$alkylamino-; and $R^{4d'}$ is $(C_1-C_6)$alkyl, $H_2NC(O)$—, $(C_1-C_4)$alkyl-NH—C(O)—, or $((C_1-C_4)$alkyl)$_2$N—C(O)—, or aryl;

or a pharmaceutically acceptable salt thereof.

13. The compound of claim 12 wherein

X is a bond or —C($R^{4c}$)($R^{4c'}$)—, where $R^{4c}$ and $R^{4c'}$ are each hydrogen; and Z is a bond or C($R^{4e}$)($R^{4e'}$)—, where $R^{4e}$ and $R^{4e'}$ are each hydrogen;

or a pharmaceutically acceptable salt thereof.

14. The compound of claim 13 wherein $R^{4d}$ is amino, $(C_1-C_6)$alkylamino, di$(C_1-C_4)$alkylamino, $(C_3-C_6)$cycloalkylamino; and $R^{4d'}$ is $H_2NC(O)$—, $(C_1-C_4)$alkyl-NH—C(O)—, or $((C_1-C_4)$alkyl)$_2$N—C(O)—;

or a pharmaceutically acceptable salt thereof.

15. The compound of claim 11, 12, 13 or 14 wherein $R^0$ and $R^1$ are each independently a phenyl substituted with 1 to 3 substituents independently selected from the group consisting of halo, $(C_1-C_4)$alkoxy, $(C_1-C_4)$alkyl, halo-substituted $(C_1-C_4)$alkyl, and cyano;

or a pharmaceutically acceptable salt thereof.

16. The compound of claim 15 wherein $R^0$ and $R^1$ are each independently a phenyl substituted with 1 to 2 substituents independently selected from the group consisting of chloro, fluoro, $(C_1-C_4)$alkoxy, $(C_1-C_4)$alkyl, fluoro-substituted $(C_1-C_4)$alkyl), and cyano;

or a pharmaceutically acceptable salt thereof.

17. The compound of claim 16 wherein $R^0$ is 2-chlorophenyl, 2-fluorophenyl, 2,4-dichlorophenyl, 2-fluoro-4-chlorophenyl, 2-chloro-4-fluorophenyl, or 2,4-difluorophenyl; and $R^1$ is 4-chlorophenyl or 4-fluorophenyl;

or a pharmaceutically acceptable salt thereof.

18. The compound of claim 17 selected from the group consisting of

1-[3-(4-chlorophenyl)-2-(2-chlorophenyl)-pyrazolo[1,5-a]pyrimidin-7-yl]-4-ethylaminopiperidine-4-carboxylic acid amide;

1-[3-(4-chlorophenyl)-2-(2-chlorophenyl)-pyrazolo[1,5-a]pyrimidin-7-yl]-4-isopropylaminopiperidine-4-carboxylic acid amide;

1-[3-(4-chlorophenyl)-2-(2-chlorophenyl)-pyrazolo[1,5-a]pyrimidin-7-yl]-3-ethylaminoazetidine-3-carboxylic acid amide;

1-[3-(4-chlorophenyl)-2-(2-chlorophenyl)-6-methylpyrazolo[1,5-a]pyrimidin-7-yl]-3-ethylaminoazetidine-3-carboxylic acid amide;

1-[3-(4-chlorophenyl)-2-(2-chlorophenyl)-5,6-dimethylpyrazolo[1,5-a]pyrimidin-7-yl]-3-ethylaminoazetidine-3-carboxylic acid amide;

1-[3-(4-chlorophenyl)-2-(2-chlorophenyl)-pyrazolo[1,5-a]pyrimidin-7-yl]-3-methylaminoazetidine-3-carboxylic acid amide;

1-[3-(4-chlorophenyl)-2-(2-chlorophenyl)-5-methylpyrazolo[1,5-a]pyrimidin-7-yl]-3-ethylaminoazetidine-3-carboxylic acid amide;

1-[3-(4-chlorophenyl)-2-(2-chlorophenyl)-6-methylpyrazolo[1,5-a]pyrimidin-7-yl]-3-methylaminoazetidine-3-carboxylic acid amide; and 1-[3-(4-chlorophenyl)-2-(2-chlorophenyl)-6-methylpyrazolo[1,5-a]pyrimidin-7-yl]-4-ethylaminopiperidine-4-carboxylic acid amide;

or a pharmaceutically acceptable salt thereof.

19. The compound of claim 18 selected from the group consisting of

1-[3-(4-chlorophenyl)-2-(2-chlorophenyl)-pyrazolo[1,5-a]pyrimidin-7-yl]4-isopropylaminopiperidine-4-carboxylic acid amide;

1-[3-(4-chlorophenyl)-2-(2-chlorophenyl)-pyrazolo[1,5-a]pyrimidin-7-yl]-3-ethylaminoazetidine-3-carboxylic acid amide;

1-[3-(4-chlorophenyl)-2-(2-chlorophenyl)-pyrazolo[1,5-a]pyrimidin-7-yl]-3-ethylaminoazetidine-3-carboxylic acid amide; and 1-[3-(4-chlorophenyl)-2-(2-chlorophenyl)-pyrazolo[1,5-a]pyrimidin-7-yl]-3-methylaminoazetidine-3-carboxylic acid amide;

or a pharmaceutically acceptable salt thereof.

20. The compound of claim 11 wherein $R^{4b}$, $R^{4b'}$, $R^{4f}$, and $R^{4f'}$ are all hydrogen;

$R^{4d}$ is hydrogen, hydroxy, amino, or a chemical moiety selected from the group consisting of $(C_1-C_6)$alkyl, $(C_1-C_6)$alkoxy, acyloxy, acyl, $(C_1-C_3)$alkyl-O-C(O)-, $(C_1-C_6)$alkylamino-, and di$(C_1-C_4)$alkylamino-, where said moiety is optionally substituted with one or more substituents; and $R^{4d'}$ is hydrogen, or a chemical moiety selected from the group consisting of $(C_1-C_6)$alkyl, aryl and heteroaryl, where said moiety is optionally substituted with one or more substituents;

or a pharmaceutically acceptable salt thereof.

21. The compound of claim 20 wherein

X is a bond or $-C(R^{4c})(R^{4c'})-$, where $R^{4c}$ and $R^{4c'}$ are each independently hydrogen or an optionally substituted $(C_1-C_6)$alkyl, or either $R^{4c}$ or $R^{4c'}$ taken together with $R^{4e}$ or $R^{4e'}$ forms a bond, a methylene bridge or an ethylene bridge; and Z is a bond or $-C(R^{4e})(R^{4e'})-$, where $R^{4e}$ and $R^{4e'}$ are each independently hydrogen or an optionally substituted $(C_1-C_6)$alkyl, or either $R^{4e}$ or $R^{4e'}$ taken together with $R^{4c}$ or $R^{4c'}$ forms a bond, a methylene bridge or an ethylene bridge;

or a pharmaceutically acceptable salt thereof.

22. The compound of claim 21 wherein $R^{4c}$ and $R^{4c'}$ are each hydrogen or either $R^{4c}$ or $R^{4c'}$ taken together with $R^{4e}$ or $R^{4e'}$ forms a bond;

$R^{4d}$ is hydrogen, hydroxy, amino, or a chemical moiety selected from the group consisting of $(C_1-C_6)$alkoxy, acyl, $(C_1-C_6)$alkylamino-, and di$(C_1-C_4)$alkylamino-;

$R^{4d'}$ is hydrogen, or a chemical moiety selected from the group consisting of $(C_1-C_6)$alkyl and aryl, where said moiety is optionally substituted with one or more substituents; and $R^{4e}$ and $R^{4e'}$ are hydrogen or either $R^{4e}$ or $R^{4e'}$ taken together with $R^{4c}$ or $R^{4c'}$ forms a bond;

or a pharmaceutically acceptable salt thereof.

23. The compound of claim 20, 21, or 22 wherein $R^0$ and $R^1$ are each independently a phenyl substituted with 1 to 3 substituents independently selected from the group consisting of halo, $(C_1-C_4)$alkoxy, $(C_1-C_4)$alkyl, halo-substituted $(C_1-C_4)$alkyl, and cyano;

or a pharmaceutically acceptable salt thereof.

24. The compound of claim 23 wherein $R^0$ and $R^1$ are each independently a phenyl substituted with 1 to 2 substituents independently selected from the group consisting of chloro, fluoro, $(C_1-C_4)$alkoxy, $(C_1-C_4)$alkyl, fluoro-substituted $(C_1-C_4)$alkyl), and cyano;

or a pharmaceutically acceptable salt thereof.

25. The compound of claim 24 wherein $R^0$ is 2-chlorophenyl, 2-fluorophenyl, 2,4-dichlorophenyl, 2-fluoro-4-chlorophenyl, 2-chloro-4-fluorophenyl, or 2,4-difluorophenyl; and $R^1$ is 4-chlorophenyl or 4-fluorophenyl;

or a pharmaceutically acceptable salt thereof.

26. The compound of claim 25 selected from the group consisting of

1-{1-[3-(4-chlorophenyl)-2-(2-chlorophenyl)-5-methylpyrazolo[1,5-a]pyrimidin-7-yl]4-phenylpiperidin-4-yl}-ethanone;

3-[3-(4-chlorophenyl)-2-(2-chlorophenyl)-5-methylpyrazolo[1,5-a]pyrimidin-7-yl]-3-(1a,5a,6a)-azabicyclo[3.1.0]hex-6-ylamine;

1-[3-(4-chlorophenyl)-2-(2-chlorophenyl)-5-methylpyrazolo[1,5-a]pyrimidin-7-yl]-4-(4-fluorophenyl)-piperidin-4-ol; and 4-benzyl-1-[3-(4-chlorophenyl)-2-(2-chlorophenyl)-5-methylpyrazolo[1,5-a]pyrimidin-7-yl]-piperidin-4-ol;

or a pharmaceutically acceptable salt thereof.

27. The compound of claim 11 wherein $R^{4b}$, $R^{4b'}$, $R^{4f}$, and $R^{4f'}$ are all hydrogen; and $R^{4d}$ and $R^{4d'}$ taken together form a 3–6 membered partially or fully saturated carbocyclic ring, a 3–6 membered partially or fully saturated heterocyclic ring, a 5–6 membered lactone ring, or a 4–6 membered lactam ring, where said carbocyclic ring, said heterocyclic ring, said lactone ring and said lactam ring are optionally substituted with one or more substituents and said lactone ring or said lactam ring optionally contains an additional heteroatom selected from oxygen, nitrogen or sulfur;

or a pharmaceutically acceptable salt thereof.

28. The compound of claim 27 wherein

X is a bond, $-CH_2CH_2-$ or $-C(R^{4c})(R^{4c'})-$, where $R^{4c}$ and $R^{4c'}$ are each independently hydrogen or an optionally substituted $(C_1-C_6)$alkyl, or either $R^{4c}$ or $R^{4c'}$ taken together with $R^{4e}$ or $R^{4e'}$ forms a bond, a methylene bridge or an ethylene bridge; and Z is a bond, $-CH_2CH_2-$ or $-C(R^{4e})(R^{4e'})-$, where $R^{4e}$ and $R^{4e'}$ are each independently hydrogen or an optionally substituted $(C_1-C_6)$alkyl, or either $R^{4e}$ or $R^{4e'}$ taken together with $R^{4c}$ or $R^{4c'}$ forms a bond, a methylene bridge or an ethylene bridge;

or a pharmaceutically acceptable salt thereof.

29. The compound of claim 27 wherein $R^{4d}$ and $R^{4d'}$ taken together form a 5–6 membered lactam ring, where said lactam ring is optionally substituted with one or more substituents and optionally contains an additional heteroatom selected from nitrogen or oxygen;

or a pharmaceutically acceptable salt thereof.

30. The compound of claim 29 wherein

X is a bond or —C($R^{4c}$)($R^{4c'}$)—, where $R^{4c}$ and $R^{4c'}$ are each hydrogen; and Z is a bond or —C($R^{4e}$)($R^{4e'}$)—, where $R^{4e}$ and $R^{4e'}$ are each hydrogen;

or a pharmaceutically acceptable salt thereof.

31. The compound of claim 27, 28, 29 or 30 wherein $R^0$ and $R^1$ are each independently a phenyl substituted with 1 to 3 substituents independently selected from the group consisting of halo, ($C_1$–$C_4$)alkoxy, ($C_1$–$C_4$)alkyl, halo-substituted ($C_1$–$C_4$)alkyl, and cyano;

or a pharmaceutically acceptable salt thereof.

32. The compound of claim 31 wherein $R^0$ and $R^1$ are each independently a phenyl substituted with 1 to 2 substituents independently selected from the group consisting of chloro, fluoro, ($C_1$–$C_4$)alkoxy, ($C_1$–$C_4$)alkyl, fluoro-substituted ($C_1$–$C_4$)alkyl, and cyano;

or a pharmaceutically acceptable salt thereof.

33. The compound of claim 32 wherein $R^0$ is 2-chlorophenyl, 2-fluorophenyl, 2,4-dichlorophenyl, 2-fluoro-4-chlorophenyl, 2-chloro-4-fluorophenyl, or 2,4-difluorophenyl; and $R^1$ is 4-chlorophenyl or 4-fluorophenyl;

or a pharmaceutically acceptable salt thereof.

34. The compound of claim 33 selected from the group consisting of

8-[3-(4-chlorophenyl)-2-(2-chlorophenyl)-5-methylpyrazolo[1,5-a]pyrimidin-7-yl]-1-isopropyl-1,3,8-triazaspiro[4.5]decan-4-one; and 2-[3-(4-chlorophenyl)-2-(2-chlorophenyl)-5-methylpyrazolo[1,5-a]pyrimidin-7-yl]-5-methyl-2,5,7-triazaspiro[3.4]octan-8-one;

or a pharmaceutically acceptable salt thereof.

35. The compound of claim 34 which is

8-[3-(4-chlorophenyl)-2-(2-chlorophenyl)-pyrazolo[1,5-a]pyrimidin-7-yl]-1-isopropyl-1,3,8-triazaspiro[4.5]decan-4-one;

or a pharmaceutically acceptable salt thereof.

36. The compound of claim 1 wherein $R^4$ is a group of Formula (IB)

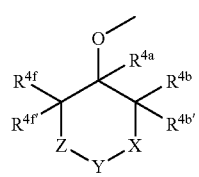

IB where $R^{4a}$ is as defined in claim 1;

$R^{4b}$ is hydrogen, cyano, hydroxy, amino, $H_2NC(O)$—, or a chemical moiety selected from the group consisting of ($C_1$–$C_6$)alkyl, ($C_1$–$C_6$)alkoxy, acyloxy, acyl, ($C_1$–$C_3$)alkyl-O—C(O)—, ($C_1$–$C_4$)alkyl-NH—C(O)—, (($C_1$–$C_4$)alkyl)$_2$N—C(O)—, ($C_1$–$C_6$)alkylamino-, (($C_1$–$C_4$)alkyl)$_2$amino-, ($C_3$–$C_6$)cycloalkylamino-, acylamino-, aryl($C_1$–$C_4$)alkylamino-, heteroaryl($C_1$–$C_4$)alkylamino-, aryl, heteroaryl, a 3–6 membered partially or fully saturated heterocycle, and a partially or fully saturated carbocyclic ring, where said moiety is optionally substituted with one or more substituents, $R^{4b'}$ is hydrogen, $H_2NC(O)$—, or a chemical moiety selected from the group consisting of ($C_1$–$C_6$)alkyl, acyl, ($C_1$–$C_3$)alkyl-O—C(O)—, ($C_1$–$C_4$)alkyl-NH—C(O)—, (($C_1$–$C_4$)alkyl)$_2$N—C(O)—, aryl, heteroaryl, a 3–6 membered partially or fully saturated heterocycle, and a partially or fully saturated carbocyclic ring, where said moiety is optionally substituted with one or more substituents, or $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —CH$_2$CH$_2$— or —C($R^{4c}$)($R^{4c'}$)—, where $R^{4c}$ is hydrogen, cyano, hydroxy, amino, $H_2NC(O)$—, or a chemical moiety selected from the group consisting of ($C_1$–$C_6$)alkyl, ($C_1$–$C_6$)alkoxy, acyloxy, acyl, ($C_1$–$C_3$)alkyl-O—C(O)—, ($C_1$–$C_4$)alkyl-NH—C(O)—, (($C_1$–$C_4$)alkyl)$_2$N—C(O)—, ($C_1$–$C_6$)alkylamino-, (($C_1$–$C_4$)alkyl)$_2$amino-, ($C_3$–$C_6$)cycloalkylamino-, acylamino-, aryl($C_1$–$C_4$)alkylamino-, heteroaryl($C_1$–$C_4$)alkylamino-, aryl, heteroaryl, a 3–6 membered partially or fully saturated heterocycle, and a partially or fully saturated carbocyclic ring, where said moiety is optionally substituted with one or more substituents, or $R^{4c}$ taken together with $R^{4e}$, $R^{4e'}$, $R^{4f}$, or $R^{4f'}$ forms a bond, a methylene bridge, or an ethylene bridge, and $R^{4c'}$ is hydrogen, $H_2NC(O)$—, or a chemical moiety selected from the group consisting of ($C_1$–$C_6$)alkyl, acyl, ($C_1$–$C_3$)alkyl-O—C(O)—, ($C_1$–$C_4$)alkyl-NH—C(O)—, (($C_1$–$C_4$)alkyl)$_2$N—C(O)—, aryl, heteroaryl, a 3–6 membered partially or fully saturated heterocycle, and a partially or fully saturated carbocyclic ring, where said moiety is optionally substituted with one or more substituents, or $R^{4c'}$ taken together with $R^{4e}$, $R^{4e'}$, $R^{4f}$, or $R^{4e'}$ forms a bond, a methylene bridge, or an ethylene bridge;

Y is oxygen, sulfur, —C(O)—, or —C($R^{4d}$)($R^{4d'}$)—, where $R^{4d}$ is hydrogen, cyano, hydroxy, amino, $H_2NC(O)$—, or a chemical moiety selected from the group consisting of ($C_1$–$C_6$)alkyl, ($C_1$–$C_6$)alkoxy, acyloxy, acyl, ($C_1$–$C_3$)alkyl-O—C(O)—, ($C_1$–$C_4$)alkyl-NH—C(O)—, (($C_1$–$C_4$)alkyl)$_2$N—C(O)—, ($C_1$–$C_6$)alkylamino-, (($C_1$–$C_4$)alkyl)$_2$amino-, ($C_3$–$C_6$)cycloalkylamino-, acylamino-, aryl($C_1$–$C_4$)alkylamino-, heteroaryl($C_1$–$C_4$)alkylamino-, aryl, heteroaryl, a 3–6 membered partially or fully saturated heterocycle, and a partially or fully saturated carbocyclic ring, where said moiety is optionally substituted with one or more substituents, and $R^{4d'}$ is hydrogen, $H_2NC(O)$—, or a chemical moiety selected from the group consisting of ($C_1$–$C_6$)alkyl, acyl, ($C_1$–$C_3$)alkyl-O—C(O)—, ($C_1$–$C_4$)alkyl-NH—C(O)—, (($C_1$–$C_4$)alkyl)$_2$N—C(O)—, aryl, heteroaryl, a 3–6 membered partially or fully saturated heterocycle, and a partially or fully saturated carbocyclic ring, where said moiety is optionally substituted with one or more substituents, or $R^{4d}$ and $R^{4d'}$ taken together form a 3–6 membered partially or fully saturated carbocyclic ring, a 3–6 membered partially or fully saturated heterocyclic ring, a 5–6 membered lactone ring, or a 4–6 membered lactam ring, where said carbocyclic ring, said heterocyclic ring, said lactone ring and said lactam ring are optionally substituted with one or more substituents and said lactone ring and said lactam ring optionally contain an additional heteroatom selected from oxygen, nitrogen or sulfur;

Y is —NR$^{4d''}$—, where R$^{4d''}$ is a hydrogen or a chemical moiety selected from the group consisting of (C$_1$–C$_6$) alkyl, (C$_3$–C$_6$)cycloalkyl, (C$_1$–C$_3$)alkylsulfonyl-, (C$_1$–C$_3$)alkylaminosulfonyl-, di(C$_1$–C$_3$)alkylaminosulfonyl-, acyl, (C$_1$–C$_6$)alkyl-O—C(O)—, aryl, and heteroaryl, where said moiety is optionally substituted with one or more substituents;

Z is a bond, —CH$_2$CH$_2$—, or —C(R$^{4e}$)(R$^{4e'}$)—, where R$^{4e}$ is hydrogen, cyano, hydroxy, amino, H$_2$NC(O)—, or a chemical moiety selected from the group consisting of (C$_1$–C$_6$)alkyl, (C$_1$–C$_6$)alkoxy, acyloxy, acyl, (C$_1$–C$_3$)alkyl-O—C(O)—, (C$_1$–C$_4$)alkyl-NH—C(O)—, (C$_1$–C$_4$)alkyl)$_2$N—C(O)—, (C$_1$–C$_6$)alkylamino-, ((C$_1$–C$_4$)alkyl)$_2$amino-, (C$_3$–C$_6$)cycloalkylamino-, acylamino-, aryl(C$_1$–C$_4$)alkylamino-, heteroaryl(C$_1$–C$_4$)alkylamino-, aryl, heteroaryl, a 3–6 membered partially or fully saturated heterocyclic ring, and a partially or fully saturated carbocyclic ring, where said moiety is optionally substituted with one or more substituents, or R$^{4e}$ taken together with R$^{4b}$, R$^{4b'}$, R$^{4c}$, or R$^{4c'}$ forms a bond, a methylene bridge, or an ethylene bridge, and R$^{4e'}$, is hydrogen, H$_2$NC(O)—, or a chemical moiety selected from the group consisting of (C$_1$–C$_6$)alkyl, acyl, (C$_1$–C$_3$)alkyl-O—C(O)—, (C$_1$–C$_4$)alkyl-NH—C(O)—, (C$_1$–C$_4$)alkyl)$_2$N—C(O)—, aryl, heteroaryl, a 3–6 membered partially or fully saturated heterocycle, and a partially or fully saturated carbocyclic ring, where said moiety is optionally substituted with one or more substituents, or R$^{4e'}$ taken together with R$^{4b}$, R$^{4b'}$, R$^{4c}$, or R$^{4c'}$ forms a bond, a methylene bridge, or an ethylene bridge;

R$^{4f}$ is hydrogen, cyano, hydroxy, amino, H$_2$NC(O)—, or a chemical moiety selected from the group consisting of (C$_1$–C$_6$)alkyl, (C$_1$–C$_6$)alkoxy, acyloxy, acyl, (C$_1$–C$_3$)alkyl-O—C(O)—, (C$_1$–C$_4$)alkyl-NH—C(O)—, (C$_1$–C$_4$)alkyl)$_2$N—C(O)—, (C$_1$–C$_6$)alkylamino-, ((C$_1$–C$_4$)alkyl)$_2$amino-, (C$_3$–C$_6$)cycloalkylamino-, acylamino-, aryl(C$_1$–C$_4$)alkylamino-, heteroaryl(C$_1$–C$_4$)alkylamino-, aryl, heteroaryl, a 3–6 membered partially or fully saturated heterocycle, and a partially or fully saturated carbocyclic ring, where said moiety is optionally substituted with one or more substituents; and R$^{4f'}$ is hydrogen, H$_2$NC(O)—, or a chemical moiety selected from the group consisting of (C$_1$–C$_6$)alkyl, acyl, (C$_1$–C$_3$)alkyl-O—C(O)—, (C$_1$–C$_4$)alkyl-NH—C(O)—, (C$_1$–C$_4$)alkyl)$_2$N—C(O)—, aryl, heteroaryl, a 3–6 membered partially or fully saturated heterocycle, and a partially or fully saturated carbocyclic ring, where said moiety is optionally substituted with one or more substituents, or R$^{4f}$ or R$^{4f'}$ taken together with R$^{4b}$, R$^{4b'}$, R$^{4c}$, or R$^{4c'}$ forms a bond, a methylene bridge, or an ethylene bridge;

or a pharmaceutically acceptable salt thereof.

37. The compound of claim 36 wherein

R$^0$ and R$^1$ are each independently a substituted phenyl;

R$^{4a}$, R$^{4b}$, R$^{4b'}$, R$^{4f}$ and R$^{4f'}$ are each hydrogen;

or a pharmaceutically acceptable salt thereof.

38. The compound of claim 37 wherein

X is a bond, —CH$_2$CH$_2$— or —C(R$^{4c}$)(R$^{4c'}$)—, where R$^{4c}$ and R$^{4c'}$ are each independently hydrogen or (C$_1$–C$_6$)alkyl;

Y is —NR$^{4d''}$—, where R$^{4d''}$ is hydrogen or a chemical moiety selected from the group consisting of (C$_1$–C$_6$) alkyl, (C$_3$–C$_6$)cycloalkyl, (C$_1$–C$_3$)alkylsulfonyl-, (C$_1$–C$_3$)alkylaminosulfonyl-, di(C$_1$–C$_3$)alkylaminosulfonyl-, acyl, (C$_1$–C$_6$)alkyl-O—C(O)—, aryl, and heteroaryl, where said moiety is optionally substituted with one or more substituents;

Z is a bond, —CH$_2$CH$_2$— or —C(R$^{4c}$)(R$^{4c'}$)—, where R$^{4c}$ and R$^{4c'}$ are each independently hydrogen or (C$_1$–C$_6$)alkyl;

or a pharmaceutically acceptable salt thereof.

39. The compound of claim 37 or 38 wherein R$^0$ and R$^1$ are each independently a phenyl substituted with 1 to 3 substituents independently selected from the group consisting of halo, (C$_1$–C$_4$)alkoxy, (C$_1$–C$_4$)alkyl, halo-substituted (C$_1$–C$_4$)alkyl, and cyano;

or a pharmaceutically acceptable salt thereof.

40. The compound of claim 39 wherein R$^0$ and R$^1$ are each independently a phenyl substituted with 1 to 2 substituents independently selected from the group consisting of chloro, fluoro, (C$_1$–C$_4$)alkoxy, (C$_1$–C$_4$)alkyl, fluoro-substituted (C$_1$–C$_4$)alkyl), and cyano;

or a pharmaceutically acceptable salt thereof.

41. The compound of claim 40 wherein R$^0$ is 2-chlorophenyl, 2-fluorophenyl, 2,4-dichlorophenyl, 2-fluoro-4-chlorophenyl, 2-chloro-4-fluorophenyl, or 2,4-difluorophenyl; and R$^1$ is 4-chlorophenyl or 4-fluorophenyl;

or a pharmaceutically acceptable salt thereof.

42. The compound of claim 41 selected from the group consisting of 7-(1-benzylpyrrolidin-3-yloxy)-3-(4-chlorophenyl)-2-(2-chlorophenyl)-5-methylpyrazolo[1,5-a]pyrimidine;

3-(4-chlorophenyl)-2-(2-chlorophenyl)-7-(1-cyclohexylazetidin-3-yloxy)-5-methylpyrazolo[1,5-a]pyrimidine; and 7-(1-tert-butylazetidin-3-yloxy)-3-(4-chlorophenyl)-2-(2-chlorophenyl)-5-methylpyrazolo[1,5-a]pyrimidine;

or a pharmaceutically acceptable salt thereof.

43. The compound of claim 1 wherein R$^4$ is —O—R$^5$, where R$^5$ taken together with R$^3$ forms a 5- to 6-membered partially saturated heterocyclic ring or a 5- to 6-membered heteroaryl, said heterocyclic ring and said heteroaryl optionally containing an additional oxygen and being optionally substituted with one or more substituents;

or a pharmaceutically acceptable salt thereof.

44. The compound of claim 43 wherein R$^0$ and R$^1$ are each independently a phenyl substituted with 1 to 3 substituents independently selected from the group consisting of halo, (C$_1$–C$_4$)alkoxy, (C$_1$–C$_4$)alkyl, halo-substituted (C$_1$–C$_4$) alkyl, and cyano;

or a pharmaceutically acceptable salt thereof.

45. The compound of claim 44 wherein R$^0$ and R$^1$ are each independently a phenyl substituted with 1 to 2 substituents independently selected from the group consisting of chloro, fluoro, (C$_1$–C$_4$)alkoxy, (C$_1$–C$_4$)alkyl, fluoro-substituted (C$_1$–C$_4$)alkyl), and cyano;

or a pharmaceutically acceptable salt thereof.

46. The compound of claim 45 wherein R$^0$ is 2-chlorophenyl, 2-fluorophenyl, 2,4-dichlorophenyl, 2-fluoro-4-chlorophenyl, 2-chloro-4-fluorophenyl, or 2,4-difluorophenyl; and R$^1$ is 4-chlorophenyl or 4-fluorophenyl;

or a pharmaceutically acceptable salt thereof.

47. The compound of claim 46 which is 3-(4-chlorophenyl)-2-(2-chlorophenyl)-7-iodomethyl-6,7-dihydro-8-oxa-1,4,8b-triaza-as-indacene.

48. A compound of Formula (II)

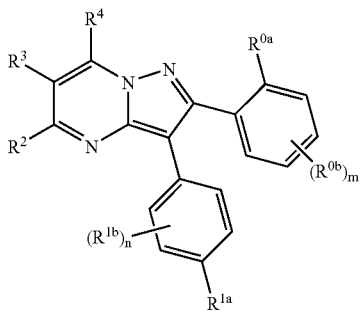

(II)

wherein
$R^{0a}$, $R^{0b}$, $R^{1a}$, and $R^{1b}$ are each independently halo, $(C_1-C_4)$alkoxy, $(C_1-C_4)$alkyl, halo-substituted $(C_1-C_4)$alkyl, or cyano;
n and m are each independently 0, 1 or 2;
$R^2$ and $R^3$ are each independently hydrogen, halo, $(C_1-C_4)$alkyl, halo-substituted $(C_1-C_4)$alkyl, or $(C_1-C_4)$alkoxy;
$R^4$ is
(i) a group having Formula (IA) or Formula (IB)

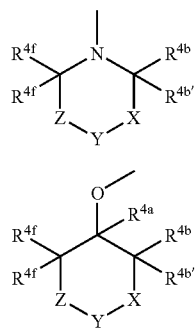

IA

IB where $R^{4a}$ is hydrogen or $(C_1-C_3)$alkyl;
$R^{4b}$ and $R^{4b'}$ are each independently hydrogen, cyano, hydroxy, amino, $H_2NC(O)—$, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, $((C_1-C_4)$alkyl$)_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3–6 membered partially or fully saturated heterocycle, and a partially or fully saturated carbocyclic ring, where the moiety is optionally substituted with one or more substituents,
or either $R^{4b}$ or $R^{4b'}$ taken together with $R^{4e}$, $R^{4e'}$, $R^{4f}$, or $R^{4f'}$ forms a bond, a methylene bridge, or an ethylene bridge;
X is a bond, —CH$_2$CH$_2$— or —C(R$^{4c}$)(R$^{4c'}$)—, where $R^{4c}$ and $R^{4c'}$ are each independently hydrogen, cyano, hydroxy, amino, $H_2NC(O)—$, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a 3–6 membered partially or fully saturated heterocycle, and a 3–6 membered partially or fully saturated carbocyclic ring, where the moiety is optionally substituted with one or more substituents,
or either $R^{4c}$ or $R^{4c'}$ taken together with $R^{4e}$, $R^{4e'}$, $R^{4f}$, or $R^{4f'}$ forms a bond, a methylene bridge or an ethylene bridge;
Y is oxygen, sulfur, —C(O)—, or —C(R$^{4d}$)(R$^{4d'}$)—, where $R^{4d}$ and $R^{4d'}$ are each independently hydrogen, cyano, hydroxy, amino, $H_2NC(O)—$, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a 3–6 membered partially or fully saturated heterocycle, and a 3–6 membered partially or fully saturated carbocyclic ring, where the moiety is optionally substituted with one or more substituents,
or $R^{4d}$ and $R^{4d'}$ taken together form a 3–6 membered partially or fully saturated carbocyclic ring, a 3–6 membered partially or fully saturated heterocyclic ring, a 5–6 membered lactone ring, or a 4–6 membered lactam ring, where said carbocyclic ring, said heterocyclic ring, said lactone ring and said lactam ring are optionally substituted with one or more substituents and said lactone ring and said lactam ring optionally contain an additional heteroatom selected from oxygen, nitrogen or sulfur, or
Y is —NR$^{4d''}$—, where $R^{4d''}$ is a hydrogen or a chemical moiety selected from the group consisting of $(C_1-C_6)$alkyl, $(C_3-C_6)$cycloalkyl, $(C_1-C_3)$alkylsulfonyl-, $(C_1-C_3)$alkylaminosulfonyl-, di$(C_1-C_3)$alkylaminosulfonyl-, acyl, $(C_1-C_6)$alkyl-O—C(O)—, aryl, and heteroaryl, where the moiety is optionally substituted with one or more substituents;
Z is a bond, —CH$_2$CH$_2$—, or —C(R$^{4e}$)(R$^{4e'}$)—, where $R^{4e}$ and $R^{4e'}$ are each independently hydrogen, cyano, hydroxy, amino, $H_2NC(O)—$, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a 3–6 membered partially or fully saturated heterocyclic ring, and a 3–6 membered partially or fully saturated carbocyclic ring, where the moiety is optionally substituted with one or more substituents,
or either $R^{4e}$ or $R^{4e'}$ taken together with $R^{4b}$, $R^{4b'}$, $R^{4c}$, or $R^{4c'}$ forms a bond, a methylene bridge or an ethylene bridge; and
$R^{4f}$ and $R^{4f'}$ are each independently hydrogen, cyano, hydroxy, amino, $H_2NC(O)—$, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, di$(C_1-C_4)$alky lamino-, ($C_3$–$C_6$)cycloalkylamino-, acylamino-, aryl($C_1$–$C_4$)alkylamino-, heteroaryl($C_1$–$C_4$)alkylamino-, aryl, heteroaryl, a 3–6 membered partially or fully saturated heterocycle, and a 3–6 membered partially or fully saturated carbocyclic ring, where the moiety is optionally substituted with one or more substituents, or either $R^{4f}$ or $R^{4f'}$ taken together with $R^{4b}$, $R^{4b'}$, $R^{4c}$, or $R^{c'}$ forms a bond, a methylene bridge or an ethylene bridge;

(ii) a group having Formula (IC)

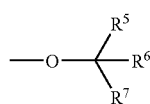

IC where $R^5$ and $R^6$ are each independently hydrogen or ($C_1$–$C_4$)alkyl, and $R^7$ is an optionally substituted ($C_1$–$C_4$)alkyl-, or an optionally substituted 4–6 membered partially or fully saturated heterocylic ring containing 1 to 2 heteroatoms independently selected from oxygen, sulfur or nitrogen, or $R^5$ and $R^6$ or $R^5$ and $R^7$ taken together form a 5–6 membered lactone, 4–6 membered lactam, or a 4–6 membered partially or fully saturated heterocycle containing 1 to 2 heteroatoms independently selected from oxygen, sulfur or nitrogen, where said lactone, said lactam and said heterocycle are optionally substituted with one or more substituents, or $R^5$, $R^6$ or $R^7$ taken together with $R^3$ forms a 5- to 6-membered partially saturated heterocyclic ring or a 5- to 6-membered heteroaryl, where said heterocyclic ring and said heteroaryl optionally contain an additional oxygen and are optionally substituted with one or more substituents;

(iii) an amino group having attached thereto at least one chemical moiety selected from the group consisting of ($C_1$–$C_8$)alkyl, aryl($C_1$–$C_4$)alkyl, a 3–8 membered partially or fully saturated carbocyclic ring, hydroxy($C_1$–$C_6$)alkyl, ($C_1$–$C_3$)alkoxy($C_1$–$C_6$)alkyl, heteroaryl($C_1$–$C_3$)alkyl, and a fully or partially saturated heterocycle, where said chemical moiety is optionally substituted with one or more substituents;

(iv) an ($C_1$–$C_6$)alkyl group having attached thereto at least one chemical moiety selected from the group consisting of hydroxy, ($C_1$–$C_6$)alkoxy, amino, ($C_1$–$C_6$)alkylamino, di(($C_1$–$C_6$)alkyl)amino ($C_1$–$C_3$)alkylsulfonyl, ($C_1$–$C_3$)alkylsulfamyl, di(($C_1$–$C_3$)alkyl)sulfamyl, acyloxy, a fully or partially saturated heterocycle, and a fully or partially saturated carbocyclic ring, where said chemical moiety is optionally substituted with one or more substituents; or (v) an optionally substituted aryl or optionally substituted heteroaryl;

or a pharmaceutically acceptable salt thereof.

49. The compound of claim 48 wherein $R^4$ is a group of Formula (IA);

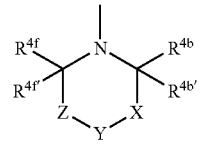

IA where, $R^{4b}$ and $R^{4b'}$ are each independently hydrogen, $H_2NC(O)$—, or a chemical moiety selected from the group consisting of ($C_1$–$C_6$)alkyl, acyl, ($C_1$–$C_3$)alkyl-O—C(O)—, ($C_1$–$C_4$)alkyl-NH—C(O)—, ($C_1$–$C_4$)alkyl)$_2$N—C(O)—, aryl, heteroaryl, a partially or fully saturated heterocycle, and a 3–6 membered partially or fully saturated carbocyclic ring, where said moiety is optionally substituted with one or more substituents, or $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —$CH_2CH_2$— or —$C(R^{4c})(R^{4c'})$—, where $R^{4c}$ is hydrogen, cyano, hydroxy, amino, $H_2NC(O)$—, or a chemical moiety selected from the group consisting of ($C_1$–$C_6$)alkyl, ($C_1$–$C_6$)alkoxy, acyloxy, acyl, ($C_1$–$C_3$)alkyl-O—C(O)—, ($C_1$–$C_4$)alkyl-NH—C(O)—, ($C_1$–$C_4$)alkyl)$_2$N—C(O)—, ($C_1$–$C_6$)alkylamino-, (($C_1$–$C_4$)alkyl)$_2$amino-, ($C_3$–$C_6$)cycloalkylamino-, acylamino-, aryl($C_1$–$C_4$)alkylamino-, heteroaryl($C_1$–$C_4$)alkylamino-, aryl, heteroaryl, a 3–6 membered partially or fully saturated heterocycle, and a partially or fully saturated carbocyclic ring, where said moiety is optionally substituted with one or more substituents, or $R^{4c}$ taken together with $R^{4e}$, $R^{4e'}$, $R^{4f}$, or $R^{4f'}$ forms a bond, a methylene bridge, or an ethylene bridge, and $R^{4c'}$ is hydrogen, $H_2NC(O)$—, or a chemical moiety selected from the group consisting of ($C_1$–$C_6$)alkyl, acyl, ($C_1$–$C_3$)alkyl-O—C(O)—, ($C_1$–$C_4$)alkyl-NH—C(O)—, ($C_1$–$C_4$)alkyl)$_2$N—C(O)—, aryl, heteroaryl, a 3–6 membered partially or fully saturated heterocycle, and a partially or fully saturated carbocyclic ring, where said moiety is optionally substituted with one or more substituents, or $R^{4c'}$ taken together with $R^{4e}$, $R^{4e'}$, $R^{4f}$, or $R^{4f'}$ forms a bond, a methylene bridge, or an ethylene bridge;

Y is oxygen, sulfur, —C(O)—, or —$C(R^{4d})(R^{4d'})$—, where $R^{4d}$ is hydrogen, cyano, hydroxy, amino, $H_2NC(O)$—, or a chemical moiety selected from the group consisting of ($C_1$–$C_6$)alkyl, ($C_1$–$C_6$)alkoxy, acyloxy, acyl, ($C_1$–$C_3$)alkyl-O—C(O)—, ($C_1$–$C_4$)alkyl-NH—C(O)—, ($C_1$–$C_4$)alkyl)$_2$N—C(O)—, ($C_1$–$C_6$)alkylamino-, (($C_1$–$C_4$)alkyl)$_2$amino-, ($C_3$–$C_6$)cycloalkylamino-, acylamino-, aryl($C_1$–$C_4$)alkylamino-, heteroaryl($C_1$–$C_4$)alkylamino-, aryl, heteroaryl, a 3–6 membered partially or fully saturated heterocycle, and a partially or fully saturated carbocyclic ring, where said moiety is optionally substituted with one or more substituents, and $R^{4d'}$ is hydrogen, $H_2NC(O)$—, or a chemical moiety selected from the group consisting of ($C_1$–$C_6$)alkyl, acyl, ($C_1$–$C_3$)alkyl-O—C(O)—, ($C_1$–$C_4$)alkyl-NH—C(O)—, ($C_1$–$C_4$)alkyl)$_2$N—C(O)—, aryl, heteroaryl, a 3–6 membered partially or fully saturated heterocycle, and a partially or fully saturated carbocyclic ring, where said moiety is optionally substituted with one or more substituents, or $R^{4d}$ and $R^{4d'}$ taken together form a 3–6 membered partially or fully saturated carbocyclic ring, a 3–6 membered partially or fully saturated heterocyclic ring, a 5–6 membered lactone ring, or a 4–6 membered lactam ring, where said carbocyclic ring, said heterocyclic ring, said lactone ring and said lactam ring are optionally substituted with one or more substituents and said lactone ring and said lactam ring optionally contain an additional heteroatom selected from oxygen, nitrogen or sulfur, or Y is —$NR^{4d''}$—, where $R^{4d''}$ is a hydrogen or a chemical moiety selected from the group consisting of ($C_1$–$C_6$) alkyl, ($C_3$–$C_6$)cycloalkyl, ($C_1$–$C_3$)alkylsulfonyl-, ($C_1$–$C_3$)alkylaminosulfonyl-, di($C_1$–$C_3$)alkylaminosulfonyl-, acyl, ($C_1$–$C_6$)alkyl-O—C(O)—, aryl, and heteroaryl, where said moiety is optionally substituted with one or more substituents;

Z is a bond, —$CH_2CH_2$—, or —$C(R^{4e})(R^{4e'})$—, where $R^{4e}$ is hydrogen, cyano, hydroxy, amino, $H_2NC(O)$—, or a chemical moiety selected from the group consisting of ($C_1$–$C_6$)alkyl, ($C_1$–$C_6$)alkoxy, acyloxy, acyl, ($C_1$–$C_3$)alkyl-O—C(O)—, ($C_1$–$C_4$)alkyl-NH—C(O)—, ($C_1$–$C_4$)alkyl)$_2$N—C(O)—, ($C_1$–$C_6$)alkylamino-, (($C_1$–$C_4$)alkyl)$_2$amino-, ($C_3$–$C_6$)cycloalkylamino-, acylamino-, aryl($C_1$–$C_4$)alkylamino-, heteroaryl($C_1$–$C_4$)alkylamino-, aryl, heteroaryl, a 3–6 membered partially or fully saturated heterocycle, and a partially or fully saturated carbocyclic ring, where said moiety is optionally substituted with one or more substituents, or $R^{4e}$ taken together with $R^{4b}$, $R^{4b'}$, $R^{4c}$, or $R^{4c'}$ forms a bond, a methylene bridge, or an ethylene bridge, and $R^{4e'}$ is hydrogen, $H_2NC(O)$—, or a chemical moiety selected from the group consisting of ($C_1$–$C_6$)alkyl, acyl, ($C_1$–$C_3$)alkyl-O—C(O)—, ($C_1$–$C_4$)alkyl-NH—C(O)—, ($C_1$–$C_4$)alkyl)$_2$N—C(O)—, aryl, heteroaryl, a 3–6 membered partially or fully saturated heterocycle, and a partially or fully saturated carbocyclic ring, where said moiety is optionally substituted with one or more substituents, or $R^{4e'}$ taken together with $R^{4b}$, $R^{4b'}$, $R^{4c}$, or $R^{4c'}$ forms a bond, a methylene bridge, or an ethylene bridge; and $R^{4f}$ and $R^{4f'}$ are each independently hydrogen, $H_2NC(O)$—, or a chemical moiety selected from the group consisting of ($C_1$–$C_6$)alkyl, acyl, ($C_1$–$C_3$)alkyl-O—C(O)—, ($C_1$–$C_4$)alkyl-NH—C(O)—, ($C_1$–$C_4$)alkyl)$_2$N—C(O)—, aryl, heteroaryl, a 3–6 membered partially or fully saturated heterocycle, and a partially or fully saturated carbocyclic ring, where said moiety is optionally substituted with one or more substituents, or $R^{4f}$ or $R^{4f'}$ taken together with $R^{4b}$, $R^{4b'}$, $R^{4c}$, or $R^{4c'}$ forms a bond, a methylene bridge, or an ethylene bridge;

or a pharmaceutically acceptable salt thereof.

50. The compound of claim of 49 wherein $R^{4b}$ is hydrogen, an optionally substituted ($C_1$–$C_3$)alkyl, or taken together with $R^{4e}$, $R^{4e'}$, $R^{4f}$, or $R^{4f'}$ forms a bond, a methylene bridge, or an ethylene bridge;

$R^{4b'}$ is hydrogen, an optionally substituted ($C_1$–$C_3$)alkyl, or taken together with $R^{4e}$, $R^{4e'}$, $R^{4f}$, or $R^{4e'}$ forms a bond, a methylene bridge, or an ethylene bridge;

$R^{4f}$ is hydrogen, an optionally substituted ($C_1$–$C_3$)alkyl, or taken together with $R^{4b}$, $R^{4b'}$, $R^{4c}$, or $R^{4c'}$ forms a bond, a methylene bridge, or an ethylene bridge; and $R^{4f'}$ is hydrogen, an optionally substituted ($C_1$–$C_3$)alkyl, or taken together with $R^{4b}$, $R^{4b'}$, $R^{4c}$, or $R^{4c'}$ forms a bond, a methylene bridge, or an ethylene bridge;

or a pharmaceutically acceptable salt thereof.

51. The compound of claim 50 wherein

X is —$C(R^{4c})(R^{4c'})$—, where $R^{4c}$ and $R^{4c'}$ are each independently hydrogen, $H_2NC(O)$—, or a chemical moiety selected from ($C_1$–$C_6$)alkyl, ($C_1$–$C_4$)alkyl-NH—C(O)—, or (($C_1$–$C_4$)alkyl)$_2$N—C(O)—, where said moiety is optionally substituted with one or more substituents, or either $R^{4c}$ or $R^{4c'}$ taken together with $R^{4e}$, $R^{4e'}$, $R^{4f}$, or $R^{4f'}$ forms a bond, a methylene bridge or an ethylene bridge;

Y is —$NR^{4d''}$—, where $R^{4d''}$ is a hydrogen or a chemical moiety selected from the group consisting of ($C_1$–$C_6$) alkyl, ($C_3$–$C_6$)cycloalkyl, ($C_1$–$C_3$)alkylsulfonyl, ($C_1$–$C_3$)alkylaminosulfonyl, di($C_1$–$C_3$)alkylaminosulfonyl, acyl, ($C_1$–$C_6$)alkyl-O—C(O)—, aryl, and heteroaryl, where said moiety is optionally substituted with one or more substituents;

Z is —$C(R^{4e})(R^{4e'})$—, where $R^{4e}$ and $R^{4e'}$ are each independently hydrogen, $H_2NC(O)$—, or a chemical moiety selected from ($C_1$–$C_6$)alkyl, ($C_1$–$C_4$)alkyl-NH—C(O)—, or (($C_1$–$C_4$)alkyl)$_2$N—C(O)—, where said moiety is optionally substituted with one or more substituents, or either $R^{4e}$ or $R^{4e'}$ taken together with $R^{4b}$, $R^{4b'}$, $R^{4c}$, or $R^{4c'}$ forms a bond, a methylene bridge or an ethylene bridge;

or a pharmaceutically acceptable salt thereof.

52. The compound of claim 51 wherein $R^{4d''}$ is a hydrogen or a chemical moiety selected from the group consisting of ($C_1$–$C_3$)alkylsulfonyl, ($C_1$–$C_3$)alkylaminosulfonyl, di($C_1$–$C_3$)alkylaminosulfonyl, acyl, ($C_1$–$C_6$)alkyl-O—C(O)—, and heteroaryl, where said moiety is optionally substituted with one or more substituents;

or a pharmaceutically acceptable salt thereof.

53. The compound of claim 52 wherein $R^{4d''}$ is a hydrogen or a chemical moiety selected from the group consisting of ($C_1$–$C_3$)alkylsulfonyl, ($C_1$–$C_3$)alkylaminosulfonyl, di($C_1$–$C_3$)alkylaminosulfonyl, acyl, and ($C_1$–$C_6$)alkyl-O—C(O)—, where said moiety is optionally substituted with 1–3 fluorines, or $R^{4d''}$ is a heteroaryl, where said heteroaryl is optionally substituted with 1 to 2 substituents independently selected from the group consisting of chloro, fluoro, ($C_1$–$C_3$)alkoxy, ($C_1$–$C_3$)alkyl, and fluoro-substituted ($C_1$–$C_3$)alkyl;

or a pharmaceutically acceptable salt thereof.

54. The compound of claim 51, 52, or 53 wherein $R^{0a}$, $R^{0a}$, $R^{1a}$ and $R^{1b}$ are each independently selected from the group consisting of halo, ($C_1$–$C_4$)alkoxy, ($C_1$–$C_4$)alkyl, halo-substituted ($C_1$–$C_4$)alkyl, and cyano;

or a pharmaceutically acceptable salt thereof.

55. The compound of claim 54 wherein $R^{0a}$, $R^{0a}$, $R^{1a}$ and $R^{1b}$ are each independently selected from the group consisting of chloro, fluoro, ($C_1$–$C_4$)alkoxy, ($C_1$–$C_4$)alkyl, fluoro-substituted ($C_1$–$C_4$)alkyl), and cyano; and n and m are each independently 0 or 1;

or a pharmaceutically acceptable salt thereof.

56. The compound of claim 50 wherein Y is —$C(R^{4d})(R^{4d'})$—, where $R^{4d}$ is hydrogen, cyano, hydroxy, amino, $H_2NC(O)$—, or a chemical moiety selected from the group consisting of ($C_1$–$C_6$)alkyl, ($C_1$–$C_6$)alkoxy, acyloxy, acyl, ($C_1$–$C_3$)alkyl-O—C(O)—, ($C_1$–$C_4$)alkyl-NH—C(O)—, ($C_1$–$C_4$)alkyl)$_2$N—C(O)—, ($C_1$–$C_6$)alkylamino-, (($C_1$–$C_4$)

alkyl)$_2$amino-, (C$_3$–C$_6$)cycloalkylamino-, acylamino-, aryl(C$_1$–C$_4$)alkylamino-, heteroaryl(C$_1$–C$_4$)alkylamino-, aryl, heteroaryl, a 3–6 membered partially or fully saturated heterocycle, and a partially or fully saturated carbocyclic ring, where said moiety is optionally substituted with one or more substituents, R$^{4d'}$ is hydrogen, H$_2$NC(O)—, or a chemical moiety selected from the group consisting of (C$_1$–C$_6$)alkyl, acyl, (C$_1$–C$_3$)alkyl-O—C(O)—, (C$_1$–C$_4$)alkyl-NH—C(O)—, (C$_1$–C$_4$)alkyl)$_2$N—C(O)—, aryl, heteroaryl, a 3–6 membered partially or fully saturated heterocycle, and a partially or fully saturated carbocyclic ring, where said moiety is optionally substituted with one or more substituents, or R$^{4d}$ and R$^{4d'}$ taken together form a 3–6 membered partially or fully saturated carbocyclic ring, a 3–6 membered partially or fully saturated heterocyclic ring, a 5–6 membered lactone ring, or a 4–6 membered lactam ring, where said carbocyclic ring, said heterocyclic ring, said lactone ring and said lactam ring are optionally substituted with one or more substituents and said lactone ring and said lactam ring optionally contain an additional heteroatom selected from oxygen, nitrogen or sulfur;

or a pharmaceutically acceptable salt thereof.

57. The compound of claim 56 wherein

R$^{4b}$, R$^{4b'}$, R$^{4f}$, and R$^{4f'}$ are all hydrogen;

R$^{4d}$ is amino, (C$_1$–C$_6$)alkylamino, di(C$_1$–C$_4$)alkylamino, (C$_3$–C$_6$)cycloalkylamino, acylamino, aryl(C$_1$–C$_4$)alkylamino-, heteroaryl(C$_1$–C$_4$)alkylamino-; and R$^{4d'}$ is (C$_1$–C$_6$)alkyl, H$_2$NC(O)—, (C$_1$–C$_4$)alkyl-NH—C(O)—, or ((C$_1$–C$_4$)alkyl)$_2$N—C(O)—, or aryl;

or a pharmaceutically acceptable salt thereof.

58. The compound of claim 57 wherein

X is a bond or —C(R$^{4c}$)(R$^{4c'}$)—, where R$^{4c}$ and R$^{4c'}$ are each hydrogen; and Z is a bond or —C(R$^{4e}$)(R$^{4e'}$)—, where R$^{4e}$ and R$^{4e'}$ are each hydrogen;

or a pharmaceutically acceptable salt thereof.

59. The compound of claim 58 wherein R$^{4d}$ is amino, (C$_1$–C$_6$)alkylamino, di(C$_1$–C$_4$)alkylamino, (C$_3$–C$_6$)cycloalkylamino; and R$^{4d'}$ is H$_2$NC(O)—, (C$_1$–C$_4$)alkyl-NH—C(O)—, or ((C$_1$–C$_4$)alkyl)$_2$N—C(O)—;

or a pharmaceutically acceptable salt thereof.

60. The compound of claim 56, 57, 58 or 59 wherein R$^{0a}$, R$^{0b}$, R$^{1a}$, and R$^{1b}$ are each independently selected from the group consisting of halo, (C$_1$–C$_4$)alkoxy, (C$_1$–C$_4$)alkyl, halo-substituted (C$_1$–C$_4$)alkyl, and cyano;

or a pharmaceutically acceptable salt thereof.

61. The compound of claim 60 wherein R$^{0a}$, R$^{0b}$, R$^{1a}$, and R$^{1b}$ are each independently selected from the group consisting of chloro, fluoro, (C$_1$–C$_4$)alkoxy, (C$_1$–C$_4$)alkyl, fluoro-substituted (C$_1$–C$_4$)alkyl), and cyano; and n and m are each independently selected from 0 or 1;

or a pharmaceutically acceptable salt thereof.

62. The compound of claim 56 wherein

R$^{4b}$, R$^{4b'}$, R$^{4f}$, and R$^{4f'}$ are all hydrogen;

R$^{4d}$ is hydrogen, hydroxy, amino, or a chemical moiety selected from the group consisting of (C$_1$–C$_6$)alkyl, (C$_1$–C$_6$)alkoxy, acyloxy, acyl, (C$_1$–C$_3$)alkyl-O—C(O)—, (C$_1$–C$_6$)alkylamino-, and di(C$_1$–C$_4$)alkylamino-, where said moiety is optionally substituted with one or more substituents; and R$^{4d'}$ is hydrogen, or a chemical moiety selected from the group consisting of (C$_1$–C$_6$)alkyl, aryl and heteroaryl, where said moiety is optionally substituted with one or more substituents;

or a pharmaceutically acceptable salt thereof.

63. The compound of claim 62 wherein

X is a bond or —C(R$^{4c}$)(R$^{4c'}$)—, where R$^{4c}$ and R$^{4c'}$ are each independently hydrogen or an optionally substituted (C$_1$–C$_6$)alkyl, or either R$^{4c}$ or R$^{4c'}$ taken together with R$^{4e}$ or R$^{4e'}$ forms a bond, a methylene bridge or an ethylene bridge; and Z is a bond or —C(R$^{4e}$)(R$^{4e'}$)—, where R$^{4e}$ and R$^{4e'}$ are each independently hydrogen or an optionally substituted (C$_1$–C$_6$)alkyl, or either R$^{4e}$ or R$^{4e'}$ taken together with R$^{4c}$ or R$^{4c'}$ forms a bond, a methylene bridge or an ethylene bridge;

or a pharmaceutically acceptable salt thereof.

64. The compound of claim 63 wherein

R$^{4c}$ and R$^{4c'}$ are each hydrogen or either R$^{4c}$ or R$^{4c'}$ taken together with R$^{4e}$ or R$^{4e'}$ forms a bond;

R$^{4d}$ is hydrogen, hydroxy, amino, or a chemical moiety selected from the group consisting of (C$_1$–C$_6$)alkoxy, acyl, (C$_1$–C$_6$)alkylamino-, and di(C$_1$–C$_4$)alkylamino-;

R$^{4d'}$ is hydrogen, or a chemical moiety selected from the group consisting of (C$_1$–C$_6$)alkyl and aryl, where said moiety is optionally substituted with one or more substituents; and R$^{4e}$ and R$^{4e'}$ are hydrogen or either R$^{4e}$ or R$^{4e'}$ taken together with R$^{4c}$ or R$^{4c'}$ forms a bond;

or a pharmaceutically acceptable salt thereof.

65. The compound of claim 62, 63, or 64 wherein R$^{0a}$, R$^{0b}$, R$^{1a}$ and R$^{1b}$ are each independently selected from the group consisting of halo, (C$_1$–C$_4$)alkoxy, (C$_1$–C$_4$)alkyl, halo-substituted (C$_1$–C$_4$)alkyl, and cyano;

or a pharmaceutically acceptable salt thereof.

66. The compound of claim 65 wherein R$^{0a}$, R$^{0b}$, R$^{1a}$, and R$^{1b}$ are each independently selected from the group consisting of chloro, fluoro, (C$_1$–C$_4$)alkoxy, (C$_1$–C$_4$)alkyl, fluoro-substituted (C$_1$–C$_4$)alkyl), and cyano; and n and m are each independently 0 or 1;

or a pharmaceutically acceptable salt thereof.

67. The compound of claim 56 wherein

R$^{4b}$, R$^{4b'}$, R$^{4f}$, and R$^{4f'}$ are all hydrogen; and

R$^{4d}$ and R$^{4d'}$ taken together form a 3–6 membered partially or fully saturated carbocyclic ring, a 3–6 membered partially or fully saturated heterocyclic ring, a 5–6 membered lactone ring, or a 4–6 membered lactam ring, where said carbocyclic ring, said heterocyclic ring, said lactone ring and said lactam ring are optionally substituted with one or more substituents and said lactone ring or said lactam ring optionally contains an additional heteroatom selected from oxygen, nitrogen or sulfur;

or a pharmaceutically acceptable salt thereof.

68. The compound of claim 67 wherein

X is a bond, —CH$_2$CH$_2$— or —C(R$^{4c}$)(R$^{4c'}$)—, where R$^{4c}$ and R$^{4c'}$ are each independently hydrogen or an optionally substituted (C$_1$-C6)alkyl, or either R$^{4c}$ or R$^{4c'}$ taken together with R$^{4e}$ or R$^{4e'}$ forms a bond, a methylene bridge or an ethylene bridge; and Z is a bond, —CH$_2$CH$_2$— or —C(R$^{4e}$)(R$^{4e'}$)—, where R$^{4e}$ and R$^{4e'}$ are each independently hydrogen or an optionally substituted (C$_1$–C$_6$)alkyl, or either R$^{4e}$ or R$^{4e'}$ taken together with R$^{4c}$ or R$^{4c'}$ forms a bond, a methylene bridge or an ethylene bridge;

or a pharmaceutically acceptable salt thereof.

69. The compound of claim 68 wherein $R^{4d}$ and $R^{4d'}$ taken together form a 5–6 membered lactam ring, where said lactam ring is optionally substituted with one or more substituents and optionally contains an additional heteroatom selected from nitrogen or oxygen;
or a pharmaceutically acceptable salt thereof.

70. The compound of claim 69 wherein
X is a bond or —C($R^{4c}$)($R^{4c'}$)—, where $R^{4c}$ and $R^{4c'}$ are each hydrogen; and
Z is a bond or —C($R^{4e}$)($R^{4e'}$)—, where $R^{4e}$ and $R^{4e'}$ are each hydrogen;
or a pharmaceutically acceptable salt thereof.

71. The compound of claim 67, 68, 69 or 70 wherein $R^{0a}$, $R^{0b}$, $R^{1a}$, and $R^{1b}$ are each independently selected from the group consisting of halo, ($C_1$–$C_4$)alkoxy, ($C_1$–$C_4$)alkyl, halo-substituted ($C_1$–$C_4$)alkyl, and cyano;
or a pharmaceutically acceptable salt thereof.

72. The compound of claim 71 wherein $R^{0a}$, $R^{0b}$, $R^{1a}$, and $R^{1b}$ are each independently selected from the group consisting of chloro, fluoro, ($C_1$–$C_4$)alkoxy, ($C_1$–$C_4$)alkyl, fluoro-substituted ($C_1$–$C_4$)alkyl), and cyano;
n and m are each independently 0 or 1;
or a pharmaceutically acceptable salt thereof.

73. The compound of claim 48 wherein $R^4$ is a group of Formula (IB);

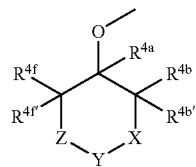

IB where $R^{4a}$ is as defined in claim 43;
$R^{4b}$ is hydrogen, cyano, hydroxy, amino, $H_2$NC(O)—, or a chemical moiety selected from the group consisting of ($C_1$–$C_6$)alkyl, ($C_1$–$C_6$)alkoxy, acyloxy, acyl, ($C_1$–$C_3$)alkyl-O—C(O)—, ($C_1$–$C_4$)alkyl-NH—C(O)—, (($C_1$–$C_4$)alkyl)$_2$N—C(O)—, ($C_1$–$C_6$)alkylamino-, (($C_1$–$C_4$)alkyl)$_2$amino-, ($C_3$–$C_6$)cycloalkylamino-, acylamino-, aryl($C_1$–$C_4$)alkylamino-, heteroaryl($C_1$–$C_4$)alkylamino-, aryl, heteroaryl, a 3–6 membered partially or fully saturated heterocycle, and a partially or fully saturated carbocyclic ring, where said moiety is optionally substituted with one or more substituents,
$R^{4b'}$ is hydrogen, $H_2$NC(O)—, or a chemical moiety selected from the group consisting of ($C_1$–$C_6$)alkyl, acyl, ($C_1$–$C_3$)alkyl-O—C(O)—, ($C_1$–$C_4$)alkyl-NH—C(O)—, (($C_1$–$C_4$)alkyl)$_2$N—C(O)—, aryl, heteroaryl, a 3–6 membered partially or fully saturated heterocycle, and a partially or fully saturated carbocyclic ring, where said moiety is optionally substituted with one or more substituents,
or $R^{4b}$ or $R^{4b'}$ taken together with $R^{4e}$, $R^{4e'}$, $R^{4f}$, or $R^{4f'}$ forms a bond, a methylene bridge, or an ethylene bridge;
X is a bond, —CH$_2$CH$_2$— or —C($R^{4c}$)($R^{4c'}$)—, where $R^{4c}$ is hydrogen, cyano, hydroxy, amino, $H_2$NC(O)—, or a chemical moiety selected from the group consisting of ($C_1$–$C_6$)alkyl, ($C_1$–$C_6$)alkoxy, acyloxy, acyl, ($C_1$–$C_3$)alkyl-O—C(O)—, ($C_1$–$C_4$)alkyl-NH—C(O)—, (($C_1$–$C_4$)alkyl)$_2$N—C(O)—, ($C_1$–$C_6$)alkylamino-, (($C_1$–$C_4$)alkyl)$_2$amino-, ($C_3$–$C_6$)cycloalkylamino-, acylamino-, aryl($C_1$–$C_4$)alkylamino-, heteroaryl($C_1$–$C_4$)alkylamino-, aryl, heteroaryl, a 3–6 membered partially or fully saturated heterocycle, and a partially or fully saturated carbocyclic ring, where said moiety is optionally substituted with one or more substituents,
or $R^{4c}$ taken together with $R^{4e}$, $R^{4e'}$, $R^{4f}$, or $R^{4f'}$ forms a bond, a methylene bridge, or an ethylene bridge, and
$R^{4c'}$ is hydrogen, $H_2$NC(O)—, or a chemical moiety selected from the group consisting of ($C_1$–$C_6$)alkyl, acyl, ($C_1$–$C_3$)alkyl-O—C(O)—, ($C_1$–$C_4$)alkyl-NH—C(O)—, (($C_1$–$C_4$)alkyl)$_2$N—C(O)—, aryl, heteroaryl, a 3–6 membered partially or fully saturated heterocycle, and a partially or fully saturated carbocyclic ring, where said moiety is optionally substituted with one or more substituents,
or $R^{4c'}$ taken together with $R^{4e}$, $R^{4e'}$, $R^{4f}$, or $R^{4f'}$ forms a bond, a methylene bridge, or an ethylene bridge;
Y is oxygen, sulfur, —C(O)—, or —C($R^{4d}$)($R^{4d'}$)—, where $R^{4d}$ is hydrogen, cyano, hydroxy, amino, $H_2$NC(O)—, or a chemical moiety selected from the group consisting of ($C_1$–$C_6$)alkyl, ($C_1$–$C_6$)alkoxy, acyloxy, acyl, ($C_1$–$C_3$)alkyl-O—C(O)—, ($C_1$–$C_4$)alkyl-NH—C(O)—, (($C_1$–$C_4$)alkyl)$_2$N—C(O)—, ($C_1$–$C_6$)alkylamino-, (($C_1$–$C_4$)alkyl)$_2$amino-, ($C_3$–$C_6$)cycloalkylamino-, acylamino-, aryl($C_1$–$C_4$)alkylamino-, heteroaryl($C_1$–$C_4$)alkylamino-, aryl, heteroaryl, a 3–6 membered partially or fully saturated heterocycle, and a partially or fully saturated carbocyclic ring, where said moiety is optionally substituted with one or more substituents, and
$R^{4d'}$ is hydrogen, $H_2$NC(O)—, or a chemical moiety selected from the group consisting of ($C_1$–$C_6$)alkyl, acyl, ($C_1$–$C_3$)alkyl-O—C(O)—, ($C_1$–$C_4$)alkyl-NH—C(O)—, (($C_1$–$C_4$)alkyl)$_2$N—C(O)—, aryl, heteroaryl, a 3–6 membered partially or fully saturated heterocycle, and a partially or fully saturated carbocyclic ring, where said moiety is optionally substituted with one or more substituents,
or $R^{4d}$ and $R^{4d'}$ taken together form a 3–6 membered partially or fully saturated carbocyclic ring, a 3–6 membered partially or fully saturated heterocyclic ring, a 5–6 membered lactone ring, or a 4–6 membered lactam ring, where said carbocyclic ring, said heterocyclic ring, said lactone ring and said lactam ring are optionally substituted with one or more substituents and said lactone ring and said lactam ring optionally contain an additional heteroatom selected from oxygen, nitrogen or sulfur;
Y is —$NR^{4d''}$—, where $R^{4d''}$ is a hydrogen or a chemical moiety selected from the group consisting of ($C_1$–$C_6$)alkyl, ($C_3$–$C_6$)cycloalkyl, ($C_1$–$C_3$)alkylsulfonyl-, ($C_1$–$C_3$)alkylaminosulfonyl-, di($C_1$–$C_3$)alkylaminosulfonyl-, acyl, ($C_1$–$C_6$)alkyl-O—C(O)—, aryl, and heteroaryl, where said moiety is optionally substituted with one or more substituents;
Z is a bond, —CH$_2$CH$_2$—, or —C($R^{4e}$)($R^{4e'}$)—, where $R^{4e}$ is hydrogen, cyano, hydroxy, amino, $H_2$NC(O)—, or a chemical moiety selected from the group consisting of ($C_1$–$C_6$)alkyl, ($C_1$–$C_6$)alkoxy, acyloxy, acyl, ($C_1$–$C_3$)alkyl-O—C(O)—, ($C_1$–$C_4$)alkyl-NH—C(O)—, (($C_1$–$C_4$)alkyl)$_2$N—C(O)—, ($C_1$–$C_6$)alkylamino-, (($C_1$–$C_4$)alkyl)$_2$amino-, ($C_3$–$C_6$)cycloalkylamino-, acylamino-, aryl($C_1$–$C_4$)alkylamino-, heteroaryl($C_1$–$C_4$)alkylamino-, aryl, heteroaryl, a 3–6 membered partially or fully saturated heterocycle, and a partially or fully saturated carbocyclic ring, where said moiety is optionally substituted with one or more substituents, or $R^{4e}$ taken together with $R^{4b}$, $R^{4b'}$, $R^{4c}$ or $R^{4c'}$ forms a bond, a methylene bridge, or an ethylene bridge, and $R^{4e'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a 3–6 membered partially or fully saturated heterocycle, and a partially or fully saturated carbocyclic ring, where said moiety is optionally substituted with one or more substituents, or $R^{4e'}$ taken together with $R^{4b}$, $R^{4b'}$, $R^{4c}$, or $R^{4c'}$ forms a bond, a methylene bridge, or an ethylene bridge;

$R^{4f}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3–6 membered partially or fully saturated heterocycle, and a partially or fully saturated carbocyclic ring, where said moiety is optionally substituted with one or more substituents; and $R^{4f'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a 3–6 membered partially or fully saturated heterocycle, and a partially or fully saturated carbocyclic ring, where said moiety is optionally substituted with one or more substituents, or $R^{4f}$ or $R^{4f'}$ taken together with $R^{4b}$, $R^{4b'}$, $R^{4c}$, or $R^{4c'}$ forms a bond, a methylene bridge, or an ethylene bridge;

or a pharmaceutically acceptable salt thereof.

74. The compound of claim 73 wherein
$R^{4a}$, $R^{4b}$, $R^{4b'}$, $R^{4f}$ and $R^{4f'}$ are each hydrogen;
or a pharmaceutically acceptable salt thereof.

75. The compound of claim 74 wherein
X is a bond, —CH$_2$CH$_2$— or —C(R$^{4c}$)(R$^{4c'}$)—, where $R^{4c}$ and $R^{4c'}$ are each independently hydrogen or $(C_1-C_6)$alkyl;

Y is —NR$^{4d''}$—, where $R^{4d''}$ is hydrogen or a chemical moiety selected from the group consisting of $(C_1-C_6)$alkyl, $(C_3-C_6)$cycloalkyl, $(C_1-C_3)$alkylsulfonyl-, $(C_1-C_3)$alkylaminosulfonyl-, di$(C_1-C_3)$alkylaminosulfonyl-, acyl, $(C_1-C_6)$alkyl-O—C(O)—, aryl, and heteroaryl, where said moiety is optionally substituted with one or more substituents;

Z is a bond, —CH$_2$CH$_2$— or —C(R$^{4c}$)(R$^{4c'}$)—, where $R^{4c}$ and $R^{4c'}$ are each independently hydrogen or $(C_1-C_6)$alkyl;

or a pharmaceutically acceptable salt thereof.

76. The compound of claim 74 or 75 wherein $R^{0a}$, $R^{0b}$, $R^{1a}$ and $R^{1b}$ are each independently selected from the group consisting of halo, $(C_1-C_4)$alkoxy, $(C_1-C_4)$alkyl, halo-substituted $(C_1-C_4)$alkyl, and cyano;
or a pharmaceutically acceptable salt thereof.

77. The compound of claim 76 wherein $R^{0a}$, $R^{0b}$, $R^{1a}$ and $R^{1b}$ are each independently selected from the group consisting of chloro, fluoro, $(C_1-C_4)$alkoxy, $(C_1-C_4)$alkyl, fluoro-substituted $(C_1-C_4)$alkyl, and cyano; and n and m are each independently 0 or 1;
or a pharmaceutically acceptable salt thereof.

78. The compound of claim 48 wherein $R^4$ is a group having Formula (IC)

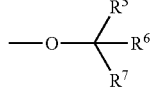

where $R^5$ and $R^6$ are each independently hydrogen or $(C_1-C_4)$alkyl, and $R^7$ is $(C_1-C_4)$alkyl-, halo-substituted $(C_1-C_4)$alkyl-, $(C_1-C_4)$alkoxy$(C_1-C_4)$alkyl-, $(C_1-C_4)$alkylamino$(C_1-C_4)$alkyl-, di$(C_1-C_4)$alkylamino$(C_1-C_4)$alkyl-, or a 4–6 membered partially or fully saturated heterocylic ring containing 1 to 2 heteroatoms independently selected from oxygen, sulfur or nitrogen, or $R^5$ and $R^6$, or $R^5$ and $R^7$ taken together form a 5–6 membered lactone, 4–6 membered lactam, or a 4–6 membered partially or fully saturated heterocycle containing 1 to 2 heteroatoms independently selected from oxygen, sulfur or nitrogen, where said lactone, said lactam and said heterocycle are optionally substituted with one or more substituents, or $R^5$, $R^6$ or $R^7$ taken together with $R^3$ forms a 5- to 6-membered partially saturated heterocyclic ring or a 5- to 6-membered heteroaryl, where said heterocyclic ring and said heteroaryl optionally contain an additional oxygen and are optionally substituted with one or more substituents;

or a pharmaceutically acceptable salt thereof.

79. The compound of claim 78 wherein n and m are each independently 1 or 0;
or a pharmaceutically acceptable salt thereof.

80. The compound of claim 79 wherein $R^5$ and $R^6$ are each independently hydrogen or $(C_1-C_4)$alkyl, and $R^7$ is $(C_1-C_4)$alkyl;
or a pharmaceutically acceptable salt thereof.

81. The compound of claim 79 wherein $R^5$, $R^6$ or $R^7$ taken together with $R^3$ forms a 5- to 6-membered partially saturated heterocyclic ring or a 5- to 6-membered heteroaryl, where said heterocyclic ring and said heteroaryl optionally contain an additional oxygen and are optionally substituted with one or more substituents;
or a pharmaceutically acceptable salt thereof.

82. The compound of claim 79, 80 or 81 wherein $R^{0a}$, $R^{0b}$, $R^{1a}$, and $R^{1b}$ are each independently chloro, fluoro or trifluoromethyl;
or a pharmaceutically acceptable salt thereof.

83. The compound of claim 81 selected from the group consisting of
3-(4-chlorophenyl)-2-(2-chlorophenyl)-7-isopropoxy-5-methylpyrazolo[1,5-a]pyrimidine;
3-(4-chlorophenyl)-2-(2-chlorophenyl)-7-ethoxypyrazolo[1,5-a]pyrimidine;
3-(4-chlorophenyl)-2-(2-chlorophenyl)-7-(2,2,2-trifluoroethoxy)-pyrazolo[1,5-a]pyrimidine; and
7-allyloxy-3-(4-chlorophenyl)-2-(2-chlorophenyl)-pyrazolo[1,5-a]pyrimidine;
or a pharmaceutically acceptable salt thereof.

84. The compound of claim 48 wherein $R^4$ is an amino group having attached thereto at least one chemical moiety selected from the group consisting of $(C_1-C_8)$alkyl, aryl$(C_1-C_4)$alkyl, a 3–8 membered partially or fully saturated carbocyclic ring, hydroxy$(C_1-C_6)$alkyl, $(C_1-C_3)$alkoxy (C₁–C₆)alkyl, heteroaryl(C₁–C₃)alkyl, and a partially or fully saturated heterocycle, where said chemical moiety is optionally substituted with one or more substituents;
or a pharmaceutically acceptable salt thereof.

85. The compound of claim 84 wherein n and m are each independently 1 or 0;
or a pharmaceutically acceptable salt thereof.

86. The compound of claim 84 or 85 wherein $R^{0a}$, $R^{0b}$, $R^{1a}$, and $R^{1b}$ are each independently chloro, fluoro or trifluoromethyl;
or a pharmaceutically acceptable salt thereof.

87. The compound of claim 86 selected from the group consisting of
butyl-[3-(4-chlorophenyl)-2-(2-chlorophenyl)-5-methylpyrazolo[1,5-a]pyrimidin-7-yl]-amine;
[3-(4-chlorophenyl)-2-(2-chlorophenyl)-5-methylpyrazolo[1,5-a]pyrimidin-7-yl]-(2-morpholin-4-yl-ethyl)-amine;
[3-(4-chlorophenyl)-2-(2-chlorophenyl)-5-methylpyrazolo[1,5-a]pyrimidin-7-yl]-(2-methoxyethyl)-amine; and
[3-(4-chlorophenyl)-2-(2-chlorophenyl)-5-methylpyrazolo[1,5-a]pyrimidin-7-yl]-[2-(4-fluorophenyl)-ethyl]-amine;
or a pharmaceutically acceptable salt thereof.

88. The compound of claim 48 wherein $R^4$ is an (C₁–C₆) alkyl group having attached thereto at least one chemical moiety selected from the group consisting of hydroxy, (C₁–C₆)alkoxy, amino, (C₁–C₆)alkylamino, di((C₁–C₆) alkyl)amino (C₁–C₃)alkylsulfonyl, (C₁–C₃)alkylsulfamyl, di((C₁–C₃)alkyl)sulfamyl, acyloxy, a partially or fully saturated heterocycle, and a partially or fully saturated carbocyclic ring, where said chemical moiety is optionally substituted with one or more substituents;
or a pharmaceutically acceptable salt thereof.

89. The compound of claim 88 wherein n and m are each independently 1 or 0;
or a pharmaceutically acceptable salt thereof.

90. The compound of claim 88 or 89 wherein $R^{0a}$, $R^{0b}$, $R^{1a}$, and $R^{1b}$ are each independently chloro, fluoro or trifluoromethyl;
or a pharmaceutically acceptable salt thereof.

91. The compound of claim 48 wherein $R^4$ is an optionally substituted aryl or optionally substituted heteroaryl;
or a pharmaceutically acceptable salt thereof.

92. The compound of claim 91 wherein n and m are each independently 1 or 0;
or a pharmaceutically acceptable salt thereof.

93. The compound of claim 91 or 92 wherein $R^{0a}$, $R^{0b}$, $R^{1a}$, and $R^{1b}$ are each independently chloro, fluoro or trifluoromethyl;
or a pharmaceutically acceptable salt thereof.

94. The compound of claim 91 which is 3,7-bis-(4-chlorophenyl)-2-(2-chlorophenyl)-pyrazolo[1,5-a]pyrimidine.

95. A pharmaceutical composition comprising (1) a compound of claim 1, or a pharmaceutically acceptable salt of said compound; and (2) a pharmaceutically acceptable excipient, diluent, or carrier.

96. The composition of claim 95 further comprising at least one additional pharmaceutical agent.

97. The composition of claim 96 wherein said additional pharmaceutical agent is a nicotine receptor partial agonist, an opioid antagonist, a dopaminergic agent, an attention deficit disorder agent, or an anti-obesity agent.

98. The composition of claim 97 wherein said anti-obesity agent is selected from the group consisting of an apo-B/MTP inhibitor, a 11β-hydroxy steroid dehydrogenase-1 inhibitor, a MCR-4 agonist, a CCK-A agonist, a monoamine reuptake inhibitor, a sympathomimetic agent, a β₃ adrenergic receptor agonist, a dopamine agonist, a melanocyte-stimulating hormone receptor analog, a 5-HT2c receptor agonist, a melanin concentrating hormone antagonist, leptin, a leptin receptor agonist, a galanin antagonist, a lipase inhibitor, a bombesin agonist, a neuropeptide-Y receptor antagonist, a thyromimetic agent, dehydroepiandrosterone, a glucocorticoid receptor antagonist, an orexin receptor antagonist, a glucagon-like peptide-1 receptor agonist, a ciliary neurotrophic factor, a human agouti-related protein antagonist, a ghrelin receptor antagonist, a histamine 3 receptor antagonist or inverse agonist, and a neuromedin U receptor agonist.

99. A method for treating a disease, condition or disorder which is modulated by a cannabinoid receptor antagonist in animals comprising the step of administering to an animal in need of such treatment a therapeutically effective amount of a compound of claim 1;
or a pharmaceutically acceptable salt thereof;
wherein said disease, condition or disorder modulated by a cannabinid receptor antagonist is selected from the group consisting of weight loss, obesity, or bulimia.

100. The method of claim 99 wherein said compound is administered in combination with a nicotine receptor partial agonist, an opioid antagonist, a dopaminergic agent, an attention deficit disorder agent, or an anti-obesity agent.

101. The method of claim 100 wherein said anti-obesity agent is selected from the group consisting of an apo-B/MTP inhibitor, a 11β-hydroxy steroid dehydrogenase-1 inhibitor, a MCR-4 agonist, a CCK-A agonist, a monoamine reuptake inhibitor, a sympathomimetic agent, a β₃ adrenergic receptor agonist, a dopamine agonist, a melanocyte-stimulating hormone receptor analog, a 5-HT2c receptor agonist, a melanin concentrating hormone antagonist, leptin, a leptin receptor agonist, a galanin antagonist, a lipase inhibitor, a bombesin agonist, a neuropeptide-Y receptor antagonist, a thyromimetic agent, dehydroepiandrosterone, a glucocorticoid receptor antagonist, an orexin receptor antagonist, a glucagon-like peptide-1 receptor agonist, a ciliary neurotrophic factor, a human agouti-related protein antagonist, a ghrelin receptor antagonist, a histamine 3 receptor antagonist or inverse agonist, and a neuromedin U receptor agonist.

102. The method of claim 99 wherein said disease, condition or disorder modulated by a cannabinoid receptor antagonist is obesity, or bulimia.

103. A method for treating a disease, condition or disorder modulated by a cannabinoid receptor antagonist comprising the step of administering a pharmaceutical composition of claim 95;
wherein said disease, condition or disorder modulated by a cannabinid receptor antagonist is selected from the group consisting of weight loss, obesity, or bulimia.

104. The method of claim 103 wherein said pharmaceutical composition further comprises an additional pharmaceutical agent.

105. The method of claim 104 wherein said additional pharmaceutical agent is a nicotine partial agonist, an opioid antagonist, a dopaminergic agent, an attention deficit disorder agent, or an anti-obesity agent.

106. The method of claim 105 wherein said anti-obesity agent is selected from the group consisting of an apo-B/MTP inhibitor, a 11β-hydroxy steroid dehydrogenase-1 inhibitor, a MCR-4 agonist, a CCK-A agonist, a monoamine reuptake inhibitor, a sympathomimetic agent, a β₃ adrenergic receptor agonist, a dopamine agonist, a melanocyte-stimulating hormone receptor analog, a 5-HT2c receptor agonist, a melanin concentrating hormone antagonist, leptin, a leptin receptor agonist, a galanin antagonist, a lipase inhibitor, a bombesin agonist, a neuropeptide-Y receptor antagonist, a thyromimetic agent, dehydroepiandrosterone, a glucocorticoid receptor antagonist, an orexin receptor antagonist, a glucagon-like peptide-1 receptor agonist, a ciliary neurotrophic factor, a human agouti-related protein antagonist, a ghrelin receptor antagonist, a histamine 3 receptor antagonist or inverse agonist, and a neuromedin U receptor agonist.

107. The method of claim 103, 104, 105 or 106 wherein said disease, condition or disorder modulated by a cannabinoid receptor antagonist is obesity, or bulimia.

108. A method for treating a disease, condition or disorder which is modulated by a cannabinoid receptor antagonist in animals comprising the step of administering to an animal in need of such treatment a therapeutically effective amount of a compound of claim 48;
or a pharmaceutically acceptable salt thereof;
wherein said disease, condition or disorder modulated by a cannabinid receptor antagonist is selected from the group consisting of weight loss, obesity, or bulimia.

109. The method of claim 108 wherein said compound is administered in combination with a nicotine partial agonist, an opioid antagonist, a dopaminergic agent, an attention deficit disorder agent, or an anti-obesity agent.

110. The method of claim 109 wherein said anti-obesity agent is selected from the group consisting of an apo-B/MTP inhibitor, a 11β-hydroxy steroid dehydrogenase-1 inhibitor, a MCR-4 agonist, a CCK-A agonist, a monoamine reuptake inhibitor, a sympathomimetic agent, a $\beta_3$ adrenergic receptor agonist, a dopamine agonist, a melanocyte-stimulating hormone receptor analog, a 5-HT2c receptor agonist, a melanin concentrating hormone antagonist, leptin, a leptin receptor agonist, a galanin antagonist, a lipase inhibitor, a bombesin agonist, a neuropeptide-Y receptor antagonist, a thyromimetic agent, dehydroepiandrosterone, a glucocorticoid receptor antagonist, an orexin receptor antagonist, a glucagon-like peptide-1 receptor agonist, a ciliary neurotrophic factor, a human agouti-related protein antagonist, a ghrelin receptor antagonist, a histamine 3 receptor antagonist or inverse agonist, and a neuromedin U receptor agonist.

111. The method of claim 108 wherein said disease, condition or disorder modulated by a cannabinoid receptor antagonist is obesity, or bulimia.

112. A method for treating a disease, condition or disorder modulated by a cannabinoid receptor antagonist in animals comprising the step of administering to an animal in need of such treatment two separate pharmaceutical compositions comprising
(i) a first composition comprising a compound of claim 1 or 48 and a pharmaceutically acceptable excipient, diluent, or carrier, and
(ii) a second composition comprising at least one additional pharmaceutical agent and a pharmaceutically acceptable excipient, diluent, or carrier;
wherein said disease, condition or disorder modulated by a cannabinid receptor antagonist is selected from the group consisting of weight loss, obesity, or bulimia.

113. The method of claim 112 wherein said at least one additional pharmaceutical agent is a nicotine partial agonist, an opioid antagonist, a dopaminergic agent, an attention deficit disorder agent, or an anti-obesity agent.

114. The method of claim 113 wherein said anti-obesity agent is selected from the group consisting of an apo-B/MTP inhibitor, a 11β-hydroxy steroid dehydrogenase-1 inhibitor, a MCR-4 agonist, a CCK-A agonist, a monoamine reuptake inhibitor, a sympathomimetic agent, a $\beta_3$ adrenergic receptor agonist, a dopamine agonist, a melanocyte-stimulating hormone receptor analog, a 5-HT2c receptor agonist, a melanin concentrating hormone antagonist, leptin, a leptin receptor agonist, a galanin antagonist, a lipase inhibitor, a bombesin agonist, a neuropeptide-Y receptor antagonist, a thyromimetic agent, dehydroepiandrosterone, a glucocorticoid receptor antagonist, an orexin receptor antagonist, a glucagon-like peptide-1 receptor agonist, a ciliary neurotrophic factor, a human agouti-related protein antagonist, a ghrelin receptor antagonist, a histamine 3 receptor antagonist or inverse agonist, and a neuromedin U receptor agonist.

115. The method of claim 112 wherein said first composition and said second composition are administered simultaneously.

116. The method of claim 112 wherein said first composition and said second composition are administered sequentially and in any order.

117. A compound of Formula (1d)

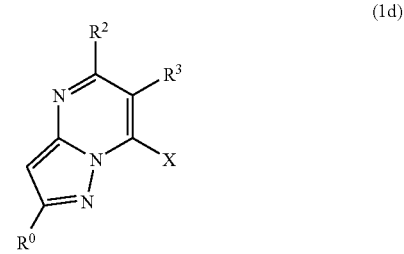

(1d)

wherein
X is chlorine or bromine;
$R^0$ is 2-chlorophenyl, 2-fluorophenyl, 2,4-dichlorophenyl, 2-fluoro-4-chlorophenyl, 2-chloro-4-fluorophenyl, or 2,4-difluorophenyl; and
$R^2$ and $R^3$ are each independently hydrogen, halo, $(C_1-C_4)$alkyl, halo-substituted $(C_1-C_4)$alkyl, or $(C_1-C_4)$alkoxy.

118. A compound of Formula (1e)

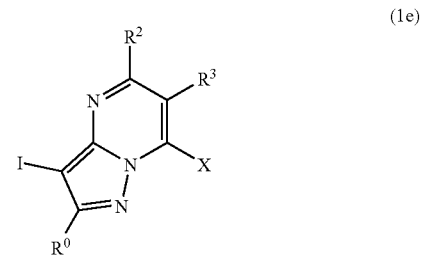

(1e)

wherein
X is chloro or bromo;
$R^0$ is 2-chlorophenyl, 2-fluorophenyl, 2,4-dichlorophenyl, 2-fluoro-4-chlorophenyl, 2-chloro-4-fluorophenyl, or 2,4-difluorophenyl; and
$R^2$ and $R^3$ are each independently hydrogen, halo, $(C_1-C_4)$alkyl, halo-substituted $(C_1-C_4)$alkyl, or $(C_1-C_4)$alkoxy.

119. A compound of Formula (1d)

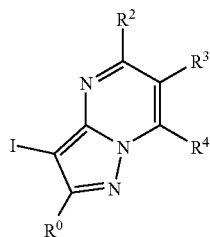

$R^0$ is 2-chlorophenyl, 2-fluorophenyl, 2,4-dichlorophenyl, 2-fluoro-4-chlorophenyl, 2-chloro-4-fluorophenyl, or 2,4-difluorophenyl;

$R^2$ and $R^3$ are each independently hydrogen, halo, $(C_1-C_4)$alkyl, halo-substituted $(C_1-C_4)$alkyl, or $(C_1-C_4)$alkoxy; and $R^4$ is (i) a group having Formula (IA) or Formula (IB)

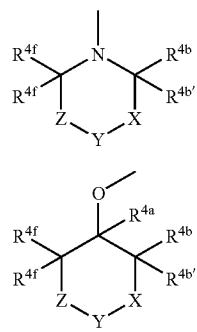

where $R^{4a}$ is hydrogen or $(C_1-C_3)$alkyl;

$R^{4b}$ and $R^{4b'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3–6 membered partially or fully saturated heterocycle, and a partially or fully saturated carbocyclic ring, where said moiety is optionally substituted with one or more substituents, or either $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —$CH_2CH_2$— or —$C(R^{4c})(R^{4c'})$—, where $R^{4c}$ and $R^{4c'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl)$_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a 3–6 membered partially or fully saturated heterocycle, and a 3–6 membered partially or fully saturated carbocyclic ring, where said moiety is optionally substituted with one or more substituents, or either $R^{4c}$ or $R^{4c'}$ taken together with $R^{4e}$, $R^{4e'}$, $R^{4f}$, or $R^{4f'}$ forms a bond, a methylene bridge or an ethylene bridge;

Y is oxygen, sulfur, —C(O)—, or —$C(R^{4d})(R^{4d'})$—, where $R^{4d}$ and $R^{4d'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl)$_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a 3–6 membered partially or fully saturated heterocycle, and a 3–6 membered partially or fully saturated carbocyclic ring, where said moiety is optionally substituted with one or more substituents, or $R^{4d}$ and $R^{4d'}$ taken together form a 3–6 membered partially or fully saturated carbocyclic ring, 3–6 membered partially or fully saturated heterocyclic ring, a 5–6 membered lactone ring, or a 4–6 membered lactam ring, where said carbocyclic ring, said heterocyclic ring, said lactone ring and said lactam ring are optionally substituted with one or more substituents and said lactone ring and said lactam ring optionally contain an additional heteroatom selected from oxygen, nitrogen or sulfur, or Y is —$NR^{4d''}$—, where $R^{4d''}$ is a hydrogen or a chemical moiety selected from the group consisting of $(C_1-C_6)$alkyl, $(C_3-C_6)$cycloalkyl, $(C_1-C_3)$alkylsulfonyl-, $(C_1-C_3)$alkylaminosulfonyl-, di$(C_1-C_3)$alkylaminosulfonyl-, acyl, $(C_1-C_6)$alkyl-O—C(O)—, aryl, and heteroaryl, where said moiety is optionally substituted with one or more substituents;

Z is a bond, —$CH_2CH_2$—, or —$C(R^{4e})(R^{4e'})$—, where $R^{4e}$ and $R^{4e'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl)$_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a 3–6 membered partially or fully saturated heterocycle, and a 3–6 membered partially or fully saturated carbocyclic ring, where said moiety is optionally substituted with one or more substituents, or either $R^{4e}$ or $R^{4e'}$ taken together with $R^{4b}$, $R^{4b'}$, $R^{4c}$, or $R^{4c'}$ forms a bond, a methylene bridge or an ethylene bridge; and $R^{4f}$ and $R^{4f'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl)$_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a 3–6 membered partially or fully saturated heterocycle, and a 3–6 membered partially or fully saturated carbocyclic ring, where said moiety is optionally substituted with one or more substituents, or either $R^{4f}$ or $R^{4f'}$ taken together with $R^{4b}$, $R^{4b'}$, $R^{4c}$, or $R^{4c'}$ forms a bond, a methylene bridge or an ethylene bridge; or (ii) —O—$R^5$, where $R^5$ taken together with $R^3$ forms a 5- to 6-membered partially saturated heterocyclic ring optionally containing an additional oxygen, or a 5-membered heteroaryl, said heterocyclic ring and said heteroaryl being optionally substituted with one or more substituents.

120. A compound of Formula (4d)

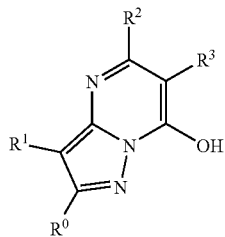

(4d)

wherein
$R^0$ is 2-chlorophenyl, 2-fluorophenyl, 2,4-dichlorophenyl, 2-fluoro-4-chlorophenyl, 2-chloro-4-fluorophenyl, or 2,4-difluorophenyl; and
$R^1$ is an optionally substituted aryl or an optionally substituted heteroaryl; and
$R^2$ and $R^3$ are each independently hydrogen, halo, ($C_1$–$C_4$)alkyl, halo-substituted ($C_1$–$C_4$)alkyl, or ($C_1$–$C_4$)alkoxy.

121. A compound of Formula (4e)

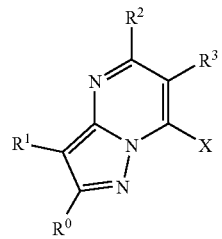

(4e)

wherein
X is chloro or bromo;
$R^0$ is an optionally substituted aryl or an optionally substituted heteroaryl;
$R^1$ is an optionally substituted aryl or an optionally substituted heteroaryl; and
$R^2$ and $R^3$ are each independently hydrogen, halo, ($C_1$–$C_4$)alkyl, halo-substituted ($C_1$–$C_4$)alkyl, or ($C_1$–$C_4$)alkoxy;
provided that $R^0$ is not 4-methylsulfonylphenyl, 4-aminosulfonylphenyl, or a 4-alkyl-substituted phenyl when $R^1$ is a 4-halo-substituted phenyl; and $R^0$ and $R^1$ are not both an unsubstituted phenyl.

* * * * *